(12) United States Patent
Roe et al.

(10) Patent No.: US 11,759,376 B2
(45) Date of Patent: *Sep. 19, 2023

(54) ABSORBENT ARTICLES WITH CHANNELS

(71) Applicant: The Procter & Gamble Company, Cincinnati, OH (US)

(72) Inventors: Donald Carroll Roe, West Chester, OH (US); Aniruddha Chatterjee, Kelkheim (DE); Nelson Edward Greening, II, Cincinnati, OH (US); Sharon Irene Grenberg, Fairfield, OH (US); Carsten Heinrich Kreuzer, Hofheim (DE); Cornelia Beate Martynus, Schwalbach (DE); Marie Brigid O'Reilly, Cincinnati, OH (US); Rodrigo Rosati, Frankfurt am Main (DE); Sandra Sautter, Schwalbach (DE); Beate Simon, Eschborn (DE); Lutz Stelzig, Frankfurt am Main (DE); Rachael Eden Walther, Union, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/852,420

(22) Filed: Jun. 29, 2022

(65) Prior Publication Data

US 2022/0323271 A1 Oct. 13, 2022

Related U.S. Application Data

(63) Continuation of application No. 16/903,664, filed on Jun. 17, 2020, which is a continuation of application
(Continued)

(51) Int. Cl.
*A61F 13/537* (2006.01)
*A61F 13/49* (2006.01)
(Continued)

(52) U.S. Cl.
CPC .. *A61F 13/53717* (2013.01); *A61F 13/49001* (2013.01); *A61F 13/533* (2013.01);
(Continued)

(58) Field of Classification Search
CPC .............. A61F 13/49001; A61F 13/533; A61F 13/53717; A61F 2013/15487;
(Continued)

(56) References Cited

U.S. PATENT DOCUMENTS 1,733,997 A 10/1929 Steven
1,734,499 A 11/1929 Davis
(Continued)

FOREIGN PATENT DOCUMENTS

CA 2001370 4/1990
CA 2291997 6/2000
(Continued)

OTHER PUBLICATIONS

US 8,293,969, Uchimoto et al. (withdrawn)
(Continued)

*Primary Examiner* — Michele Kidwell
(74) *Attorney, Agent, or Firm* — Christian M. Best

(57) ABSTRACT

The present disclosure is directed, in part, to an absorbent article comprising a topsheet, a backsheet and absorbent core positioned at least partially intermediate the topsheet and the backsheet. The absorbent core comprises an absorbent material positioned within a core wrap. The absorbent core defines a first channel therein. A material is positioned
(Continued)

at least partially intermediate the topsheet and the core wrap. The material defines a second channel therein.

20 Claims, 16 Drawing Sheets

Related U.S. Application Data

No. 15/942,607, filed on Apr. 2, 2018, now Pat. No. 10,736,794, which is a continuation of application No. 14/467,095, filed on Aug. 25, 2014, now Pat. No. 9,987,176.

(60) Provisional application No. 61/870,391, filed on Aug. 27, 2013.

(51) Int. Cl.
  *A61F 13/533* (2006.01)
  *A61F 13/15* (2006.01)
  *A61F 13/53* (2006.01)

(52) U.S. Cl.
  CPC ............. *A61F 2013/15487* (2013.01); *A61F 2013/530051* (2013.01); *A61F 2013/530649* (2013.01); *A61F 2013/53734* (2013.01)

(58) Field of Classification Search
  CPC ........ A61F 2013/530051; A61F 2013/530649; A61F 2013/53734
  See application file for complete search history.

(56) References Cited

U.S. PATENT DOCUMENTS

| | | |
|---|---|---|
| 1,989,283 A | 1/1935 | Limacher |
| 2,058,509 A | 10/1936 | David |
| 2,271,676 A | 2/1942 | Elna |
| 2,450,789 A | 10/1948 | Frieman |
| 2,508,811 A | 5/1950 | Best et al. |
| 2,570,796 A | 10/1951 | Rose |
| 2,570,963 A | 10/1951 | Mesmer |
| 2,583,553 A | 1/1952 | Faure |
| 2,705,957 A | 4/1955 | Virginia |
| 2,788,003 A | 4/1957 | Norden |
| 2,788,786 A | 4/1957 | Dexter |
| 2,798,489 A | 7/1957 | Mayes |
| 2,807,263 A | 9/1957 | Mae |
| 2,830,589 A | 4/1958 | Doner |
| 2,890,700 A | 6/1959 | Lonberg-holm |
| 2,890,701 A | 6/1959 | Weinman |
| 2,898,912 A | 8/1959 | Adams |
| 2,931,361 A | 4/1960 | Sostrin |
| 2,977,957 A | 4/1961 | Joseph |
| 3,071,138 A | 1/1963 | Gustavo |
| 3,180,335 A | 4/1965 | Duncan et al. |
| 3,207,158 A | 9/1965 | Kazuko et al. |
| 3,227,160 A | 1/1966 | Younger |
| 3,386,442 A | 6/1968 | Reinhardt |
| 3,561,446 A | 2/1971 | Jones, Sr. |
| 3,572,342 A | 3/1971 | Lindquist |
| 3,572,432 A | 3/1971 | Aulick |
| 3,575,174 A | 4/1971 | Mogor |
| 3,578,155 A | 5/1971 | Small et al. |
| 3,606,887 A | 9/1971 | Roeder |
| 3,610,244 A | 10/1971 | Jones, Sr. |
| 3,618,608 A | 11/1971 | Brink |
| 3,642,001 A | 2/1972 | Sabee |
| 3,653,381 A | 4/1972 | Warnken |
| 3,670,731 A | 6/1972 | Harmon |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand |
| 3,828,784 A | 8/1974 | Zoephel |
| 3,840,418 A | 10/1974 | Sabee |
| 3,847,702 A | 11/1974 | Jones |
| 3,848,594 A | 11/1974 | Buell |
| 3,848,595 A | 11/1974 | Endres |
| 3,848,597 A | 11/1974 | Endres |
| 3,860,003 A | 1/1975 | Buell |
| 3,863,637 A | 2/1975 | Macdonald et al. |
| 3,882,870 A | 5/1975 | Hathaway |
| 3,884,234 A | 5/1975 | Taylor |
| 3,900,032 A | 8/1975 | Heurlen |
| 3,911,173 A | 10/1975 | Sprague, Jr. |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,055,180 A | 10/1977 | Karami |
| 4,074,508 A | 2/1978 | Reid |
| 4,079,739 A | 3/1978 | Whitehead |
| 4,084,592 A | 4/1978 | Tritsch |
| 4,100,922 A | 7/1978 | Hernandez |
| 4,232,674 A | 11/1980 | Melican |
| 4,257,418 A | 3/1981 | Hessner |
| 4,259,220 A | 3/1981 | Bunnelle et al. |
| 4,296,750 A | 10/1981 | Woon et al. |
| 4,315,508 A | 2/1982 | Bolick |
| 4,324,246 A | 4/1982 | Mullane et al. |
| 4,340,706 A | 7/1982 | Obayashi et al. |
| 4,341,216 A | 7/1982 | Obenour |
| 4,342,314 A | 8/1982 | Radel et al. |
| 4,360,021 A | 11/1982 | Stima |
| 4,381,783 A | 5/1983 | Elias |
| 4,388,075 A | 6/1983 | Mesek et al. |
| 4,410,571 A | 10/1983 | Korpman |
| 4,461,621 A | 7/1984 | Karami et al. |
| 4,463,045 A | 7/1984 | Ahr |
| 4,469,710 A | 9/1984 | Rielley et al. |
| 4,475,912 A | 10/1984 | Coates |
| 4,490,148 A | 12/1984 | Beckestroem |
| 4,507,438 A | 3/1985 | Obayashi et al. |
| 4,515,595 A | 5/1985 | Kievit |
| 4,527,990 A | 7/1985 | Sigl |
| 4,541,871 A | 9/1985 | Obayashi et al. |
| 4,551,191 A | 11/1985 | Kock et al. |
| 4,573,986 A | 3/1986 | Minetola |
| 4,578,072 A | 3/1986 | Lancaster |
| 4,578,702 A | 3/1986 | Campbell, III |
| 4,585,448 A | 4/1986 | Enloe |
| 4,585,450 A | 4/1986 | Rosch et al. |
| 4,589,878 A | 5/1986 | Mitrani |
| 4,596,568 A | 6/1986 | Flug |
| 4,601,717 A | 7/1986 | Blevins |
| 4,606,964 A | 8/1986 | Wideman |
| 4,609,518 A | 9/1986 | Curro et al. |
| 4,610,678 A | 9/1986 | Weisman |
| 4,623,342 A | 11/1986 | Ito et al. |
| 4,624,666 A | 11/1986 | Derossett et al. |
| 4,629,643 A | 12/1986 | Curro |
| 4,636,207 A | 1/1987 | Buell |
| 4,641,381 A | 2/1987 | Heran et al. |
| 4,643,727 A | 2/1987 | Rosenbaum |
| 4,646,510 A | 3/1987 | Mcintyre |
| 4,662,875 A | 5/1987 | Hirotsu |
| 4,666,983 A | 5/1987 | Tsubakimoto et al. |
| 4,670,011 A | 6/1987 | Mesek |

(56) References Cited

U.S. PATENT DOCUMENTS

| | | |
|---|---|---|
| 4,670,012 A | 6/1987 | Johnson |
| 4,680,030 A | 7/1987 | Coates et al. |
| 4,681,579 A | 7/1987 | Toussant et al. |
| 4,681,581 A | 7/1987 | Coates |
| 4,681,793 A | 7/1987 | Linman et al. |
| 4,690,680 A | 9/1987 | Higgins |
| 4,695,278 A | 9/1987 | Lawson |
| 4,699,622 A | 10/1987 | Toussant |
| 4,704,115 A | 11/1987 | Buell |
| 4,704,116 A | 11/1987 | Enloe |
| 4,710,189 A | 12/1987 | Lash |
| 4,720,321 A | 1/1988 | Smith |
| 4,731,066 A | 3/1988 | Korpman |
| 4,731,070 A | 3/1988 | Koci |
| 4,741,941 A | 5/1988 | Englebert |
| 4,747,846 A | 5/1988 | Boland et al. |
| 4,753,648 A | 6/1988 | Jackson |
| 4,773,905 A | 9/1988 | Molee et al. |
| 4,784,892 A | 11/1988 | Storey et al. |
| 4,785,996 A | 11/1988 | Ziecker |
| 4,787,896 A | 11/1988 | Houghton et al. |
| 4,795,454 A | 1/1989 | Dragoo |
| 4,800,102 A | 1/1989 | Takada |
| 4,802,884 A | 2/1989 | Froeidh |
| 4,806,408 A | 2/1989 | Pierre et al. |
| 4,806,598 A | 2/1989 | Morman |
| 4,808,176 A | 2/1989 | Kielpikowski |
| 4,808,178 A | 2/1989 | Aziz |
| 4,826,880 A | 5/1989 | Lesniak |
| 4,834,735 A | 5/1989 | Alemany |
| 4,834,740 A | 5/1989 | Suzuki et al. |
| 4,834,742 A | 5/1989 | Wilson et al. |
| 4,838,886 A | 6/1989 | Kent |
| 4,842,666 A | 6/1989 | Werenicz |
| 4,846,815 A | 7/1989 | Scripps |
| 4,846,825 A | 7/1989 | Enloe et al. |
| 4,848,815 A | 7/1989 | Molloy |
| 4,861,652 A | 8/1989 | Lippert et al. |
| 4,869,724 A | 9/1989 | Scripps |
| 4,886,697 A | 12/1989 | Perdelwitz, Jr. et al. |
| 4,888,231 A | 12/1989 | Angstadt |
| 4,892,528 A | 1/1990 | Suzuki |
| 4,892,535 A | 1/1990 | Bjoernberg et al. |
| 4,892,536 A | 1/1990 | Desmarais |
| 4,894,060 A | 1/1990 | Nestegard |
| 4,894,277 A | 1/1990 | Akasaki |
| 4,900,317 A | 2/1990 | Buell |
| 4,904,251 A | 2/1990 | Igaue et al. |
| 4,909,802 A | 3/1990 | Ahr et al. |
| 4,909,803 A | 3/1990 | Aziz |
| 4,936,839 A | 6/1990 | Molee et al. |
| 4,940,463 A | 7/1990 | Leathers et al. |
| 4,940,464 A | 7/1990 | Van Gompel et al. |
| 4,946,527 A | 8/1990 | Battrell |
| 4,950,264 A | 8/1990 | Osborn, III |
| 4,960,477 A | 10/1990 | Mesek |
| 4,963,140 A | 10/1990 | Robertson |
| 4,966,809 A | 10/1990 | Tanaka et al. |
| 4,968,313 A | 11/1990 | Sabee |
| 4,990,147 A | 2/1991 | Freeland |
| 4,994,053 A | 2/1991 | Lang |
| 5,006,394 A | 4/1991 | Baird |
| 5,019,063 A | 5/1991 | Marsan et al. |
| 5,019,072 A | 5/1991 | Polski |
| 5,021,051 A | 6/1991 | Hiuke |
| 5,030,314 A | 7/1991 | Lang |
| 5,032,120 A | 7/1991 | Freeland et al. |
| 5,034,008 A | 7/1991 | Breitkopf |
| 5,037,416 A | 8/1991 | Allen |
| 5,071,414 A | 12/1991 | Elliott |
| 5,072,687 A | 12/1991 | Mitchell et al. |
| 5,085,654 A | 2/1992 | Buell |
| 5,087,255 A | 2/1992 | Sims |
| 5,092,861 A | 3/1992 | Nomura |
| 5,102,597 A | 4/1992 | Berg et al. |
| 5,114,420 A | 5/1992 | Igaue et al. |
| 5,124,188 A | 6/1992 | Roe et al. |
| 5,135,522 A | 8/1992 | Fahrenkrug et al. |
| 5,137,537 A | 8/1992 | Herron |
| D329,697 S | 9/1992 | Fahrenkrug et al. |
| 5,143,679 A | 9/1992 | Weber |
| 5,147,343 A | 9/1992 | Kellenberger |
| 5,147,345 A | 9/1992 | Lavon |
| 5,149,334 A | 9/1992 | Berg et al. |
| 5,149,335 A | 9/1992 | Kellenberger |
| 5,151,091 A | 9/1992 | Glaug et al. |
| 5,151,092 A | 9/1992 | Buell |
| 5,156,793 A | 10/1992 | Buell |
| 5,167,653 A | 12/1992 | Igaue et al. |
| 5,167,897 A | 12/1992 | Weber |
| 5,175,046 A | 12/1992 | Nguyen |
| 5,180,622 A | 1/1993 | Lahrman et al. |
| 5,190,563 A | 3/1993 | Herron et al. |
| 5,190,606 A | 3/1993 | Merkatoris et al. |
| 5,204,997 A | 4/1993 | Suzuki et al. |
| 5,213,817 A | 5/1993 | Pelley |
| 5,221,274 A | 6/1993 | Buell |
| 5,235,515 A | 8/1993 | Ungpiyakul et al. |
| 5,242,436 A | 9/1993 | Weil |
| 5,246,431 A | 9/1993 | Minetola et al. |
| 5,246,432 A | 9/1993 | Suzuki et al. |
| 5,246,433 A | 9/1993 | Hasse |
| 5,248,309 A | 9/1993 | Serbiak |
| 5,260,345 A | 11/1993 | Desmarais |
| 5,269,775 A | 12/1993 | Freeland |
| 5,281,683 A | 1/1994 | Yano et al. |
| 5,300,565 A | 4/1994 | Berg et al. |
| 5,312,386 A | 5/1994 | Correa et al. |
| 5,331,059 A | 7/1994 | Engelhardt et al. |
| 5,336,552 A | 8/1994 | Strack et al. |
| 5,348,547 A | 9/1994 | Payne et al. |
| 5,358,500 A | 10/1994 | Lavon et al. |
| 5,366,451 A | 11/1994 | Levesque |
| 5,366,782 A | 11/1994 | Curro et al. |
| 5,382,610 A | 1/1995 | Harada et al. |
| 5,387,207 A | 2/1995 | Dyer |
| 5,387,208 A | 2/1995 | Ashton |
| 5,387,209 A | 2/1995 | Yamamoto et al. |
| 5,389,095 A | 2/1995 | Suzuki et al. |
| 5,397,316 A | 3/1995 | Young |
| 5,397,317 A | 3/1995 | Thomas |
| 5,399,175 A | 3/1995 | Glaug et al. |
| 5,401,792 A | 3/1995 | Babu et al. |
| 5,409,771 A | 4/1995 | Dahmen et al. |
| 5,411,497 A | 5/1995 | Tanzer |
| 5,415,644 A | 5/1995 | Enloe |
| 5,425,725 A | 6/1995 | Tanzer |
| 5,429,630 A | 7/1995 | Beal et al. |
| 5,433,715 A | 7/1995 | Tanzer |
| 5,451,219 A | 9/1995 | Suzuki et al. |
| 5,451,442 A | 9/1995 | Pieniak et al. |
| 5,460,622 A | 10/1995 | Dragoo et al. |
| 5,460,623 A | 10/1995 | Emenaker et al. |
| 5,462,541 A | 10/1995 | Bruemmer et al. |
| 5,476,458 A | 12/1995 | Glaug et al. |
| 5,486,166 A | 1/1996 | Bishop et al. |
| 5,486,167 A | 1/1996 | Dragoo et al. |
| 5,490,846 A | 2/1996 | Ellis et al. |
| 5,492,962 A | 2/1996 | Lahrman et al. |
| 5,494,622 A | 2/1996 | Heath et al. |
| 5,499,978 A | 3/1996 | Buell |
| 5,507,736 A | 4/1996 | Clear |
| 5,507,895 A | 4/1996 | Suekane |
| 5,509,915 A | 4/1996 | Hanson |
| 5,514,104 A | 5/1996 | Cole et al. |
| 5,518,801 A | 5/1996 | Chappell |
| 5,520,674 A | 5/1996 | Lavon et al. |
| 5,522,810 A | 6/1996 | Allen, Jr. et al. |
| 5,527,300 A | 6/1996 | Sauer |
| 5,531,730 A | 7/1996 | Dreier |
| 5,532,323 A | 7/1996 | Yano et al. |
| 5,542,943 A | 8/1996 | Sageser |
| 5,549,592 A | 8/1996 | Fries et al. |
| 5,549,593 A | 8/1996 | Ygge et al. |

(56) References Cited

U.S. PATENT DOCUMENTS

| | | | |
|---|---|---|---|
| 5,549,791 | A | 8/1996 | Herron et al. |
| 5,554,145 | A | 9/1996 | Roe |
| 5,559,335 | A | 9/1996 | Zeng et al. |
| 5,560,878 | A | 10/1996 | Dragoo et al. |
| 5,562,634 | A | 10/1996 | Flumene et al. |
| 5,562,646 | A | 10/1996 | Goldman |
| 5,562,650 | A | 10/1996 | Everett et al. |
| 5,569,234 | A | 10/1996 | Buell |
| 5,571,096 | A | 11/1996 | Dobrin |
| 5,574,121 | A | 11/1996 | Irie et al. |
| 5,575,783 | A | 11/1996 | Clear |
| 5,580,411 | A | 12/1996 | Nease |
| 5,584,829 | A | 12/1996 | Lavash et al. |
| 5,586,979 | A | 12/1996 | Thomas |
| 5,591,152 | A | 1/1997 | Buell |
| 5,591,155 | A | 1/1997 | Nishikawa |
| 5,593,399 | A | 1/1997 | Tanzer |
| 5,599,335 | A | 2/1997 | Goldman |
| 5,601,542 | A | 2/1997 | Melius |
| 5,607,414 | A | 3/1997 | Richards |
| 5,607,416 | A | 3/1997 | Yamamoto et al. |
| 5,607,537 | A | 3/1997 | Johnson et al. |
| 5,607,760 | A | 3/1997 | Roe |
| 5,609,587 | A | 3/1997 | Roe |
| 5,609,588 | A | 3/1997 | Dipalma et al. |
| 5,611,879 | A | 3/1997 | Morman |
| 5,613,959 | A | 3/1997 | Roessler et al. |
| 5,613,960 | A | 3/1997 | Mizutani |
| 5,614,283 | A | 3/1997 | Potnis et al. |
| 5,622,589 | A | 4/1997 | Johnson et al. |
| 5,624,423 | A | 4/1997 | Anjur et al. |
| 5,624,424 | A | 4/1997 | Saisaka et al. |
| 5,625,222 | A | 4/1997 | Yoneda |
| 5,626,571 | A | 5/1997 | Young et al. |
| 5,628,736 | A | 5/1997 | Thompson |
| 5,628,741 | A | 5/1997 | Buell et al. |
| 5,628,845 | A | 5/1997 | Murray et al. |
| 5,635,191 | A | 6/1997 | Roe |
| 5,635,271 | A | 6/1997 | Zafiroglu |
| 5,637,106 | A | 6/1997 | Mitchell et al. |
| 5,643,238 | A | 7/1997 | Baker |
| 5,643,243 | A | 7/1997 | Klemp |
| 5,643,588 | A | 7/1997 | Roe |
| 5,649,914 | A | 7/1997 | Glaug et al. |
| 5,650,214 | A | 7/1997 | Anderson et al. |
| 5,658,268 | A | 8/1997 | Johns et al. |
| 5,662,634 | A | 9/1997 | Yamamoto et al. |
| 5,662,638 | A | 9/1997 | Johnson et al. |
| 5,662,758 | A | 9/1997 | Hamilton et al. |
| 5,669,894 | A | 9/1997 | Goldman |
| 5,674,215 | A | 10/1997 | Roennberg |
| 5,681,300 | A | 10/1997 | Ahr |
| 5,683,374 | A | 11/1997 | Yamamoto et al. |
| 5,685,874 | A | 11/1997 | Buell et al. |
| 5,690,624 | A | 11/1997 | Sasaki et al. |
| 5,690,627 | A | 11/1997 | Clear et al. |
| 5,691,035 | A | 11/1997 | Chappell et al. |
| 5,691,036 | A | 11/1997 | Lin et al. |
| 5,695,488 | A | 12/1997 | Sosalla |
| 5,700,254 | A | 12/1997 | Mcdowall |
| 5,702,376 | A | 12/1997 | Glaug et al. |
| 5,714,156 | A | 2/1998 | Schmidt et al. |
| 5,723,087 | A | 3/1998 | Chappell et al. |
| 5,733,275 | A | 3/1998 | Davis et al. |
| 5,749,866 | A | 5/1998 | Roe et al. |
| 5,752,947 | A | 5/1998 | Awolin |
| 5,756,039 | A | 5/1998 | Mcfall |
| 5,762,641 | A | 6/1998 | Bewick-sonntag |
| 5,766,388 | A | 6/1998 | Pelley et al. |
| 5,766,389 | A | 6/1998 | Brandon et al. |
| 5,772,825 | A | 6/1998 | Schmitz |
| 5,776,121 | A | 7/1998 | Roe et al. |
| 5,779,831 | A | 7/1998 | Schmitz |
| 5,788,684 | A | 8/1998 | Abuto et al. |
| 5,795,345 | A | 8/1998 | Mizutani et al. |
| 5,797,892 | A | 8/1998 | Glaug |
| 5,797,894 | A | 8/1998 | Cadieux et al. |
| 5,807,365 | A | 9/1998 | Luceri |
| 5,810,796 | A | 9/1998 | Kimura |
| 5,810,800 | A | 9/1998 | Hunter et al. |
| 5,814,035 | A | 9/1998 | Gryskiewicz et al. |
| 5,820,618 | A | 10/1998 | Roberts et al. |
| 5,827,257 | A | 10/1998 | Fujioka et al. |
| 5,830,202 | A | 11/1998 | Bogdanski et al. |
| 5,833,678 | A | 11/1998 | Ashton et al. |
| 5,837,789 | A | 11/1998 | Stockhausen et al. |
| 5,840,404 | A | 11/1998 | Graff |
| 5,843,059 | A | 12/1998 | Niemeyer et al. |
| 5,846,231 | A | 12/1998 | Fujioka et al. |
| 5,846,232 | A | 12/1998 | Serbiak et al. |
| 5,849,816 | A | 12/1998 | Suskind et al. |
| 5,851,204 | A | 12/1998 | Mizutani |
| 5,855,572 | A | 1/1999 | Schmidt |
| 5,858,013 | A | 1/1999 | Kling |
| 5,858,515 | A | 1/1999 | Stokes et al. |
| 5,865,823 | A | 2/1999 | Curro |
| 5,865,824 | A | 2/1999 | Chen et al. |
| 5,873,868 | A | 2/1999 | Nakahata |
| 5,876,391 | A | 3/1999 | Roe et al. |
| 5,879,751 | A | 3/1999 | Bogdanski |
| 5,891,118 | A | 4/1999 | Toyoshima et al. |
| 5,891,544 | A | 4/1999 | Chappell et al. |
| 5,897,545 | A | 4/1999 | Kline |
| 5,904,673 | A | 5/1999 | Roe et al. |
| 5,925,439 | A | 7/1999 | Haubach |
| 5,928,184 | A | 7/1999 | Etheredge et al. |
| 5,931,825 | A | 8/1999 | Kuen et al. |
| 5,938,648 | A | 8/1999 | Beck |
| 5,938,650 | A | 8/1999 | Baer et al. |
| 5,941,862 | A | 8/1999 | Haynes et al. |
| 5,944,706 | A | 8/1999 | Palumbo et al. |
| 5,947,949 | A | 9/1999 | Inoue et al. |
| 5,951,536 | A | 9/1999 | Osborn, III et al. |
| 5,957,908 | A | 9/1999 | Kline |
| 5,968,025 | A | 10/1999 | Roe |
| 5,968,029 | A | 10/1999 | Chappell et al. |
| 5,980,500 | A | 11/1999 | Shimizu et al. |
| 5,981,824 | A | 11/1999 | Luceri |
| 5,989,236 | A | 11/1999 | Roe et al. |
| 6,004,306 | A | 12/1999 | Robles |
| 6,022,430 | A | 2/2000 | Blenke et al. |
| 6,022,431 | A | 2/2000 | Blenke et al. |
| 6,042,673 | A | 3/2000 | Johnson et al. |
| 6,050,984 | A | 4/2000 | Fujioka |
| 6,054,631 | A | 4/2000 | Gent |
| 6,056,732 | A | 5/2000 | Fujioka et al. |
| 6,060,115 | A | 5/2000 | Borowski et al. |
| 6,068,620 | A | 5/2000 | Chmielewski |
| 6,080,909 | A | 6/2000 | Oesterdahl et al. |
| 6,083,210 | A | 7/2000 | Young et al. |
| 6,090,994 | A | 7/2000 | Chen |
| 6,091,336 | A | 7/2000 | Zand et al. |
| 6,093,474 | A | 7/2000 | Sironi |
| 6,099,515 | A | 8/2000 | Sugito |
| 6,102,892 | A | 8/2000 | Putzer et al. |
| 6,103,814 | A | 8/2000 | Vandrongelen et al. |
| 6,107,537 | A | 8/2000 | Elder |
| 6,110,157 | A | 8/2000 | Schmidt |
| 6,117,121 | A | 9/2000 | Faulks et al. |
| 6,117,803 | A | 9/2000 | Morman et al. |
| 6,120,486 | A | 9/2000 | Toyoda et al. |
| 6,120,487 | A | 9/2000 | Ashton |
| 6,120,489 | A | 9/2000 | Johnson |
| 6,120,866 | A | 9/2000 | Arakawa et al. |
| 6,121,509 | A | 9/2000 | Ashraf et al. |
| 6,129,717 | A | 10/2000 | Fujioka et al. |
| 6,129,720 | A | 10/2000 | Blenke et al. |
| 6,132,411 | A | 10/2000 | Huber et al. |
| 6,139,912 | A | 10/2000 | Onuschak et al. |
| 6,143,821 | A | 11/2000 | Houben |
| 6,152,908 | A | 11/2000 | Widlund et al. |
| 6,156,023 | A | 12/2000 | Yoshioka |
| 6,156,424 | A | 12/2000 | Taylor |
| 6,160,197 | A | 12/2000 | Lassen et al. |

(56) References Cited

U.S. PATENT DOCUMENTS

| | | |
|---|---|---|
| 6,165,160 A | 12/2000 | Suzuki |
| 6,174,302 B1 | 1/2001 | Kumasaka |
| 6,177,606 B1 | 1/2001 | Etheredge et al. |
| 6,177,607 B1 | 1/2001 | Blaney et al. |
| 6,186,996 B1 | 2/2001 | Martin |
| 6,210,386 B1 | 4/2001 | Inoue |
| 6,210,390 B1 | 4/2001 | Karlsson |
| 6,221,460 B1 | 4/2001 | Weber et al. |
| 6,231,556 B1 | 5/2001 | Osborn, III |
| 6,231,566 B1 | 5/2001 | Lai |
| 6,238,380 B1 | 5/2001 | Sasaki |
| 6,241,714 B1 | 6/2001 | Raidel et al. |
| 6,241,716 B1 | 6/2001 | Roennberg |
| 6,254,294 B1 | 7/2001 | Muhar |
| 6,258,996 B1 | 7/2001 | Goldman |
| 6,265,488 B1 | 7/2001 | Nagasuna et al. |
| 6,290,686 B1 | 9/2001 | Tanzer |
| 6,293,933 B1 | 9/2001 | Ahlstrand |
| 6,306,122 B1 | 10/2001 | Narawa et al. |
| 6,315,765 B1 | 11/2001 | Datta et al. |
| 6,319,239 B1 | 11/2001 | Daniels |
| 6,322,552 B1 | 11/2001 | Blenke et al. |
| 6,325,787 B1 | 12/2001 | Roe et al. |
| 6,326,525 B1 | 12/2001 | Hamajima et al. |
| 6,330,735 B1 | 12/2001 | Hahn et al. |
| 6,334,858 B1 | 1/2002 | Ronnberg et al. |
| 6,336,922 B1 | 1/2002 | Vangompel et al. |
| 6,340,611 B1 | 1/2002 | Shimizu et al. |
| 6,342,715 B1 | 1/2002 | Shimizu et al. |
| 6,350,332 B1 | 2/2002 | Thomas et al. |
| 6,368,687 B1 | 4/2002 | Joseph et al. |
| 6,371,948 B1 | 4/2002 | Mizutani |
| 6,372,952 B1 | 4/2002 | Lash et al. |
| 6,375,644 B2 | 4/2002 | Mizutani |
| 6,376,034 B1 | 4/2002 | Brander |
| 6,383,431 B1 | 5/2002 | Dobrin |
| 6,383,960 B1 | 5/2002 | Everett et al. |
| 6,394,989 B2 | 5/2002 | Mizutani |
| 6,402,729 B1 | 6/2002 | Boberg et al. |
| 6,402,731 B1 | 6/2002 | Suprise et al. |
| 6,403,857 B1 | 6/2002 | Gross et al. |
| 6,406,467 B1 | 6/2002 | Dilnik et al. |
| 6,409,883 B1 | 6/2002 | Makolin |
| 6,410,820 B1 | 6/2002 | Mcfall et al. |
| 6,410,822 B1 | 6/2002 | Mizutani |
| 6,413,248 B1 | 7/2002 | Mizutani |
| 6,413,249 B1 | 7/2002 | Turi et al. |
| 6,414,214 B1 | 7/2002 | Engelhardt et al. |
| 6,416,502 B1 | 7/2002 | Connelly et al. |
| 6,416,697 B1 | 7/2002 | Venturino et al. |
| 6,419,667 B1 | 7/2002 | Avalon et al. |
| 6,420,622 B1 | 7/2002 | Johnston et al. |
| 6,423,046 B1 | 7/2002 | Fujioka et al. |
| 6,423,048 B1 | 7/2002 | Suzuki et al. |
| 6,423,884 B1 | 7/2002 | Oehmen |
| 6,429,350 B1 | 8/2002 | Tanzer et al. |
| 6,432,094 B1 | 8/2002 | Fujioka et al. |
| 6,432,098 B1 | 8/2002 | Kline |
| 6,432,099 B2 | 8/2002 | Roennberg |
| 6,437,214 B1 | 8/2002 | Everett et al. |
| 6,441,268 B1 | 8/2002 | Edwardsson |
| 6,443,933 B1 | 9/2002 | Suzuki et al. |
| 6,444,064 B1 | 9/2002 | Henry |
| 6,447,496 B1 | 9/2002 | Mizutani |
| 6,458,111 B1 | 10/2002 | Onishi et al. |
| 6,458,877 B1 | 10/2002 | Ahmed et al. |
| 6,459,016 B1 | 10/2002 | Rosenfeld et al. |
| 6,461,034 B1 | 10/2002 | Cleveland |
| 6,461,342 B2 | 10/2002 | Tanji et al. |
| 6,461,343 B1 | 10/2002 | Schaefer et al. |
| 6,472,478 B1 | 10/2002 | Funk |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,500,159 B1 | 12/2002 | Carvalho |
| 6,503,233 B1 | 1/2003 | Chen |
| 6,503,979 B1 | 1/2003 | Funk et al. |
| 6,506,186 B1 | 1/2003 | Roessler et al. |
| 6,506,961 B1 | 1/2003 | Levy |
| 6,515,195 B1 | 2/2003 | Lariviere et al. |
| 6,517,525 B1 | 2/2003 | Berthou et al. |
| 6,518,479 B1 | 2/2003 | Graef et al. |
| 6,520,947 B1 | 2/2003 | Tilly et al. |
| 6,521,811 B1 | 2/2003 | Lassen et al. |
| 6,521,812 B1 | 2/2003 | Graef et al. |
| 6,524,294 B1 | 2/2003 | Hilston et al. |
| 6,525,240 B1 | 2/2003 | Graef et al. |
| 6,528,698 B2 | 3/2003 | Mizutani et al. |
| 6,529,860 B1 | 3/2003 | Strumolo et al. |
| 6,531,025 B1 | 3/2003 | Lender et al. |
| 6,531,027 B1 | 3/2003 | Lender et al. |
| 6,534,149 B1 | 3/2003 | Daley et al. |
| 6,559,081 B1 | 5/2003 | Erspamer et al. |
| 6,559,239 B1 | 5/2003 | Riegel et al. |
| 6,562,168 B1 | 5/2003 | Schmitt et al. |
| 6,562,192 B1 | 5/2003 | Hamilton |
| 6,569,137 B2 | 5/2003 | Suzuki et al. |
| 6,573,422 B1 | 6/2003 | Rosenfeld et al. |
| 6,585,713 B1 | 7/2003 | Lemahieu et al. |
| 6,585,858 B1 | 7/2003 | Otto et al. |
| 6,602,234 B2 | 8/2003 | Klemp et al. |
| 6,605,070 B2 | 8/2003 | Ludwig et al. |
| 6,605,172 B1 | 8/2003 | Anderson et al. |
| 6,605,752 B2 | 8/2003 | Magnusson et al. |
| 6,610,900 B1 | 8/2003 | Tanzer |
| 6,613,955 B1 | 9/2003 | Lindsay et al. |
| 6,630,054 B1 | 10/2003 | Graef et al. |
| 6,632,209 B1 | 10/2003 | Chmielewski |
| 6,632,504 B1 | 10/2003 | Gillespie |
| 6,645,569 B2 | 11/2003 | Cramer |
| 6,646,180 B1 | 11/2003 | Chmielewski |
| 6,648,869 B1 | 11/2003 | Gillies et al. |
| 6,648,870 B2 | 11/2003 | Itoh et al. |
| 6,648,871 B2 | 11/2003 | Kusibojoska et al. |
| 6,649,807 B2 | 11/2003 | Mizutani |
| 6,649,810 B1 | 11/2003 | Minato et al. |
| 6,657,015 B1 | 12/2003 | Riegel et al. |
| 6,657,102 B2 | 12/2003 | Furuya et al. |
| 6,667,424 B1 | 12/2003 | Hamilton |
| 6,670,522 B1 | 12/2003 | Graef et al. |
| 6,673,982 B1 | 1/2004 | Chen |
| 6,673,983 B1 | 1/2004 | Graef et al. |
| 6,673,985 B2 | 1/2004 | Mizutani et al. |
| 6,682,515 B1 | 1/2004 | Mizutani et al. |
| 6,682,516 B2 | 1/2004 | Johnston et al. |
| 6,689,115 B1 | 2/2004 | Coenen et al. |
| 6,689,934 B2 | 2/2004 | Dodge, II et al. |
| 6,695,827 B2 | 2/2004 | Chen |
| 6,700,034 B1 | 3/2004 | Lindsay et al. |
| 6,700,036 B2 | 3/2004 | Thomas et al. |
| 6,703,538 B2 | 3/2004 | Lassen et al. |
| 6,705,465 B2 | 3/2004 | Ling et al. |
| 6,706,129 B2 | 3/2004 | Ando et al. |
| 6,706,943 B2 | 3/2004 | Onishi et al. |
| 6,710,224 B2 | 3/2004 | Chmielewski et al. |
| 6,710,225 B1 | 3/2004 | Everett et al. |
| 6,716,205 B2 | 4/2004 | Coenen et al. |
| 6,716,441 B1 | 4/2004 | Osborne et al. |
| 6,717,029 B2 | 4/2004 | Baker |
| 6,726,668 B2 | 4/2004 | Underhill et al. |
| 6,726,792 B1 | 4/2004 | Johnson et al. |
| 6,730,387 B2 | 5/2004 | Rezai et al. |
| 6,734,335 B1 | 5/2004 | Graef et al. |
| 6,746,976 B1 | 6/2004 | Urankar et al. |
| 6,790,798 B1 | 9/2004 | Suzuki |
| 6,802,834 B2 | 10/2004 | Melius et al. |
| 6,809,158 B2 | 10/2004 | Ikeuchi et al. |
| 6,811,642 B2 | 11/2004 | Ochi |
| 6,818,083 B2 | 11/2004 | Mcamish et al. |
| 6,818,166 B2 | 11/2004 | Edwardson et al. |
| 6,830,800 B2 | 12/2004 | Curro et al. |
| 6,832,905 B2 | 12/2004 | Delzer et al. |
| 6,840,929 B2 | 1/2005 | Kurata |
| 6,846,374 B2 | 1/2005 | Coenen et al. |

(56) References Cited

U.S. PATENT DOCUMENTS

| | | |
|---|---|---|
| 6,858,771 B2 | 2/2005 | Yoshimasa et al. |
| 6,863,933 B2 | 3/2005 | Cramer |
| 6,863,960 B2 | 3/2005 | Curro et al. |
| 6,867,345 B2 | 3/2005 | Shimoe et al. |
| 6,867,346 B1 | 3/2005 | Dopps et al. |
| 6,878,433 B2 | 4/2005 | Curro |
| 6,878,647 B1 | 4/2005 | Rezai |
| 6,880,211 B2 | 4/2005 | Jackson et al. |
| 6,891,080 B2 | 5/2005 | Minato et al. |
| 6,903,243 B1 | 6/2005 | Burton |
| 6,904,865 B2 | 6/2005 | Klofta et al. |
| 6,911,574 B1 | 6/2005 | Mizutani |
| 6,923,797 B2 | 8/2005 | Shinohara et al. |
| 6,923,926 B2 | 8/2005 | Walter et al. |
| 6,926,703 B2 | 8/2005 | Sugito et al. |
| 6,929,629 B2 | 8/2005 | Drevik et al. |
| 6,939,914 B2 | 9/2005 | Qin et al. |
| 6,946,585 B2 | 9/2005 | London |
| 6,953,451 B2 | 10/2005 | Berba et al. |
| 6,955,667 B1 | 10/2005 | Tanaka et al. |
| 6,955,733 B2 | 10/2005 | Miller |
| 6,962,578 B1 | 11/2005 | Lavon |
| 6,962,645 B2 | 11/2005 | Graef et al. |
| 6,965,058 B1 | 11/2005 | Raidel |
| 6,969,781 B2 | 11/2005 | Graef et al. |
| 6,972,010 B2 | 12/2005 | Pesce et al. |
| 6,972,011 B2 | 12/2005 | Mori |
| 6,974,892 B2 | 12/2005 | Decarvalho et al. |
| 6,979,564 B2 | 12/2005 | Glucksmann et al. |
| 6,982,052 B2 | 1/2006 | Daniels et al. |
| 7,001,167 B2 | 2/2006 | Venturino et al. |
| 7,014,632 B2 | 3/2006 | Takino et al. |
| 7,015,370 B2 | 3/2006 | Watanabe et al. |
| 7,037,299 B2 | 5/2006 | Turi et al. |
| 7,037,571 B2 | 5/2006 | Fish et al. |
| 7,048,726 B2 | 5/2006 | Kusagawa et al. |
| 7,056,311 B2 | 6/2006 | Kinoshita et al. |
| 7,067,711 B2 | 6/2006 | Kuroda et al. |
| 7,073,373 B2 | 7/2006 | La Fortune |
| 7,078,583 B2 | 7/2006 | Kudo et al. |
| 7,090,665 B2 | 8/2006 | Ohashi et al. |
| 7,108,759 B2 | 9/2006 | You et al. |
| 7,108,916 B2 | 9/2006 | Ehrnsperger |
| 7,112,621 B2 | 9/2006 | Rohrbaugh |
| 7,122,713 B2 | 10/2006 | Komatsu et al. |
| 7,125,470 B2 | 10/2006 | Graef et al. |
| 7,132,585 B2 | 11/2006 | Kudo et al. |
| 7,147,628 B2 | 12/2006 | Drevik |
| 7,150,729 B2 | 12/2006 | Shimada et al. |
| 7,154,019 B2 | 12/2006 | Mishima et al. |
| 7,160,281 B2 | 1/2007 | Leminh et al. |
| 7,163,528 B2 | 1/2007 | Christon |
| 7,166,190 B2 | 1/2007 | Graef et al. |
| 7,169,136 B2 | 1/2007 | Otsubo et al. |
| 7,183,360 B2 | 2/2007 | Daniel et al. |
| 7,189,888 B2 | 3/2007 | Wang et al. |
| 7,196,241 B2 | 3/2007 | Kinoshita et al. |
| 7,199,211 B2 | 4/2007 | Popp et al. |
| 7,204,830 B2 | 4/2007 | Mishima et al. |
| 7,207,978 B2 | 4/2007 | Takino et al. |
| 7,219,403 B2 | 5/2007 | Miyamoto et al. |
| 7,220,251 B2 | 5/2007 | Otsubo et al. |
| 7,241,280 B2 | 7/2007 | Christon et al. |
| 7,250,481 B2 | 7/2007 | Jaworek et al. |
| 7,252,657 B2 | 8/2007 | Mishima et al. |
| 7,265,258 B2 | 9/2007 | Hamilton |
| 7,270,651 B2 | 9/2007 | Adams |
| 7,285,178 B2 | 10/2007 | Mischler |
| 7,306,582 B2 | 12/2007 | Adams |
| 7,311,696 B2 | 12/2007 | Christon et al. |
| 7,311,968 B2 | 12/2007 | Ehrnsperger et al. |
| 7,312,372 B2 | 12/2007 | Miyama et al. |
| 7,318,820 B2 | 1/2008 | Lavon et al. |
| 7,329,244 B2 | 2/2008 | Otsubo et al. |
| 7,329,246 B2 | 2/2008 | Kinoshita et al. |
| 7,335,810 B2 | 2/2008 | Yoshimasa et al. |
| 7,377,914 B2 | 5/2008 | Lavon |
| 7,429,689 B2 | 9/2008 | Chen |
| 7,435,244 B2 | 10/2008 | Schroer, Jr. et al. |
| 7,465,373 B2 | 12/2008 | Graef et al. |
| 7,500,969 B2 | 3/2009 | Mishima et al. |
| 7,504,552 B2 | 3/2009 | Tamura et al. |
| 7,504,553 B2 | 3/2009 | Nagahara et al. |
| 7,521,109 B2 | 4/2009 | Suzuki et al. |
| 7,521,587 B2 | 4/2009 | Busam et al. |
| 7,537,832 B2 | 5/2009 | Carlucci et al. |
| 7,547,815 B2 | 6/2009 | Ohashi et al. |
| 7,550,646 B2 | 6/2009 | Tamura et al. |
| 7,563,257 B2 | 7/2009 | Nakajima et al. |
| 7,588,561 B2 | 9/2009 | Kenmochi et al. |
| 7,594,904 B2 | 9/2009 | Rosenfeld et al. |
| 7,598,428 B2 | 10/2009 | Gustavsson et al. |
| 7,625,363 B2 | 12/2009 | Yoshimasa et al. |
| 7,641,642 B2 | 1/2010 | Murai et al. |
| 7,648,490 B2 | 1/2010 | Kuroda et al. |
| 7,652,111 B2 | 1/2010 | Hermeling et al. |
| 7,666,173 B2 | 2/2010 | Mishima et al. |
| 7,666,174 B2 | 2/2010 | Onishi et al. |
| 7,686,790 B2 | 3/2010 | Rasmussen et al. |
| 7,687,596 B2 | 3/2010 | Hermeling et al. |
| 7,695,461 B2 | 4/2010 | Rosenfeld et al. |
| 7,696,402 B2 | 4/2010 | Nishikawa et al. |
| 7,708,725 B2 | 5/2010 | Tamagawa et al. |
| 7,717,150 B2 | 5/2010 | Manabe et al. |
| 7,718,249 B2 | 5/2010 | Russell et al. |
| 7,718,844 B2 | 5/2010 | Olson |
| 7,722,587 B2 | 5/2010 | Suzuki et al. |
| 7,722,590 B2 | 5/2010 | Tsuji et al. |
| 7,727,217 B2 | 6/2010 | Hancock-cooke |
| 7,736,351 B2 | 6/2010 | Nigam et al. |
| 7,737,324 B2 | 6/2010 | Lavon et al. |
| 7,744,576 B2 | 6/2010 | Busam |
| 7,744,578 B2 | 6/2010 | Tanio et al. |
| 7,750,203 B2 | 7/2010 | Becker et al. |
| 7,754,822 B2 | 7/2010 | Daniel et al. |
| 7,754,940 B2 | 7/2010 | Brisebois et al. |
| 7,759,540 B2 | 7/2010 | Litvay et al. |
| 7,763,004 B2 | 7/2010 | Lavon |
| 7,767,875 B2 | 8/2010 | Olson et al. |
| 7,767,876 B2 | 8/2010 | Davis et al. |
| 7,767,878 B2 | 8/2010 | Suzuki |
| 7,772,420 B2 | 8/2010 | Hermeling et al. |
| 7,786,341 B2 | 8/2010 | Schneider et al. |
| 7,795,492 B2 | 9/2010 | Vartiainen |
| 7,803,145 B2 | 9/2010 | Rosenfeld et al. |
| 7,825,291 B2 | 11/2010 | Elfsberg et al. |
| 7,838,722 B2 | 11/2010 | Blessing et al. |
| 7,850,672 B2 | 12/2010 | Guidotti et al. |
| 7,851,667 B2 | 12/2010 | Becker et al. |
| 7,855,314 B2 | 12/2010 | Hanao et al. |
| 7,857,797 B2 | 12/2010 | Kudo et al. |
| 7,858,842 B2 | 12/2010 | Komatsu et al. |
| 7,884,259 B2 | 2/2011 | Hanao et al. |
| 7,888,549 B2 | 2/2011 | Jansson et al. |
| 7,910,797 B2 | 3/2011 | Nandrea et al. |
| 7,931,636 B2 | 4/2011 | Lavon et al. |
| 7,935,207 B2 | 5/2011 | Zhao et al. |
| 7,935,861 B2 | 5/2011 | Suzuki |
| 7,938,813 B2 | 5/2011 | Wang et al. |
| 7,942,858 B2 | 5/2011 | Francoeur et al. |
| 7,951,126 B2 | 5/2011 | Nanjyo et al. |
| 7,959,620 B2 | 6/2011 | Miura et al. |
| 7,982,091 B2 | 7/2011 | Konawa |
| 7,993,319 B2 | 8/2011 | Sperl |
| 8,017,827 B2 | 9/2011 | Hundorf et al. |
| 8,029,486 B2 | 10/2011 | Nakajima et al. |
| 8,030,536 B2 | 10/2011 | Ponomarenko et al. |
| 8,034,991 B2 | 10/2011 | Bruzadin et al. |
| 8,039,684 B2 | 10/2011 | Guidotti et al. |
| 8,052,454 B2 | 11/2011 | Polnyi |
| 8,057,620 B2 | 11/2011 | Perego et al. |
| 8,109,915 B2 | 2/2012 | Shimoe et al. |
| 8,124,828 B2 | 2/2012 | Kline et al. |
| 8,133,212 B2 | 3/2012 | Takada |

(56) References Cited

U.S. PATENT DOCUMENTS

| | | | |
|---|---|---|---|
| 8,148,598 B2 | 4/2012 | Tsang et al. |
| 8,163,124 B2 | 4/2012 | Moriura et al. |
| 8,167,862 B2 | 5/2012 | Digiacomantonio et al. |
| 8,173,858 B2 | 5/2012 | Kuroda et al. |
| 8,178,747 B2 | 5/2012 | Venturino et al. |
| 8,183,430 B2 | 5/2012 | Haakansson et al. |
| 8,186,296 B2 | 5/2012 | Brown |
| 8,187,239 B2 | 5/2012 | Lavon |
| 8,187,240 B2 | 5/2012 | Busam et al. |
| 8,198,506 B2 | 6/2012 | Venturino et al. |
| 8,211,815 B2 | 7/2012 | Baker et al. |
| 8,236,715 B2 | 8/2012 | Schmidt et al. |
| 8,237,012 B2 | 8/2012 | Miyama et al. |
| 8,246,594 B2 | 8/2012 | Sperl et al. |
| 8,258,367 B2 | 9/2012 | Lawson et al. |
| 8,268,424 B1 | 9/2012 | Suzuki et al. |
| 8,273,943 B2 | 9/2012 | Noda et al. |
| 8,282,617 B2 | 10/2012 | Kaneda |
| 8,283,516 B2 | 10/2012 | Litvay |
| 8,317,766 B2 | 11/2012 | Naoto et al. |
| 8,317,768 B2 | 11/2012 | Larsson |
| 8,319,005 B2 | 11/2012 | Becker et al. |
| 8,343,123 B2 | 1/2013 | Noda et al. |
| 8,343,296 B2 | 1/2013 | Blessing et al. |
| 8,360,977 B2 | 1/2013 | Marttila et al. |
| 8,361,047 B2 | 1/2013 | Mukai et al. |
| 8,377,025 B2 | 2/2013 | Nakajima et al. |
| 8,450,555 B2 | 5/2013 | Nhan et al. |
| 8,496,637 B2 | 7/2013 | Hundorf et al. |
| 8,519,213 B2 | 8/2013 | Venturino et al. |
| 8,524,355 B2 | 9/2013 | Nakaoka |
| 8,552,252 B2 | 10/2013 | Hundorf et al. |
| 8,568,380 B2 | 10/2013 | Brownlee |
| 8,568,566 B2 | 10/2013 | Jackels et al. |
| 8,569,571 B2 | 10/2013 | Kline et al. |
| 8,581,019 B2 | 11/2013 | Carlucci et al. |
| 8,603,058 B2 | 12/2013 | Sperl et al. |
| 8,604,270 B2 | 12/2013 | Venturino et al. |
| 8,633,347 B2 | 1/2014 | Bianco et al. |
| 8,664,468 B2 | 3/2014 | Lawson et al. |
| 8,674,170 B2 | 3/2014 | Busam et al. |
| 8,734,417 B2 | 5/2014 | Lavon et al. |
| 8,766,031 B2 | 7/2014 | Becker et al. |
| 8,772,570 B2 | 7/2014 | Kawakami et al. |
| 8,784,594 B2 | 7/2014 | Blessing et al. |
| 8,785,715 B2 | 7/2014 | Wright et al. |
| 8,791,318 B2 | 7/2014 | Becker et al. |
| 8,936,584 B2 | 1/2015 | Zander et al. |
| 8,979,815 B2 | 3/2015 | Roe et al. |
| 9,056,034 B2 | 6/2015 | Akiyama |
| 9,066,831 B2 | 6/2015 | Moriya et al. |
| 9,066,837 B2 | 6/2015 | Kim et al. |
| 9,326,896 B2 | 5/2016 | Schäfer et al. |
| 9,789,011 B2 | 10/2017 | Roe et al. |
| 9,987,176 B2 | 6/2018 | Roe et al. |
| 10,335,324 B2 | 7/2019 | Roe et al. |
| 10,736,794 B2 * | 8/2020 | Roe .................. A61F 13/53717 |
| 11,406,544 B2 * | 8/2022 | Roe .................. A61F 13/49001 |
| 2001/0007065 A1 | 7/2001 | Blanchard et al. |
| 2001/0008964 A1 | 7/2001 | Kurata et al. |
| 2001/0016548 A1 | 8/2001 | Kugler et al. |
| 2001/0020157 A1 | 9/2001 | Mizutani et al. |
| 2001/0037101 A1 | 11/2001 | Allan et al. |
| 2001/0044610 A1 | 11/2001 | Kim et al. |
| 2002/0007167 A1 | 1/2002 | Dan et al. |
| 2002/0007169 A1 | 1/2002 | Graef |
| 2002/0016122 A1 | 2/2002 | Curro |
| 2002/0016579 A1 | 2/2002 | Stenberg |
| 2002/0045881 A1 | 4/2002 | Kusibojoska et al. |
| 2002/0056516 A1 | 5/2002 | Ochi |
| 2002/0058919 A1 | 5/2002 | Hamilton et al. |
| 2002/0062112 A1 | 5/2002 | Mizutani |
| 2002/0062115 A1 | 5/2002 | Wada et al. |
| 2002/0062116 A1 | 5/2002 | Mizutani et al. |
| 2002/0065498 A1 | 5/2002 | Ohashi et al. |
| 2002/0072471 A1 | 6/2002 | Ikeuchi et al. |
| 2002/0082575 A1 | 6/2002 | Dan et al. |
| 2002/0087139 A1 | 7/2002 | Coenen et al. |
| 2002/0095127 A1 | 7/2002 | Fish et al. |
| 2002/0102392 A1 | 8/2002 | Fish et al. |
| 2002/0115969 A1 | 8/2002 | Mori et al. |
| 2002/0123728 A1 | 9/2002 | Graef et al. |
| 2002/0123848 A1 | 9/2002 | Schneiderman et al. |
| 2002/0151634 A1 | 10/2002 | Rohrbaugh et al. |
| 2002/0151861 A1 | 10/2002 | Klemp et al. |
| 2002/0173767 A1 | 11/2002 | Coenen |
| 2002/0192366 A1 | 12/2002 | Cramer et al. |
| 2002/0197695 A1 | 12/2002 | Glucksmann et al. |
| 2003/0036741 A1 | 2/2003 | Abba et al. |
| 2003/0078553 A1 | 4/2003 | Wada |
| 2003/0084983 A1 | 5/2003 | Rangachari et al. |
| 2003/0088223 A1 | 5/2003 | Vogt et al. |
| 2003/0088229 A1 | 5/2003 | Baker et al. |
| 2003/0105190 A1 | 6/2003 | Diehl |
| 2003/0109839 A1 | 6/2003 | Costea |
| 2003/0114811 A1 | 6/2003 | Christon |
| 2003/0114816 A1 | 6/2003 | Underhill et al. |
| 2003/0114818 A1 | 6/2003 | Benecke |
| 2003/0115969 A1 | 6/2003 | Koyano |
| 2003/0120235 A1 | 6/2003 | Boulanger |
| 2003/0120249 A1 | 6/2003 | Wulz et al. |
| 2003/0135176 A1 | 7/2003 | Delzer et al. |
| 2003/0135181 A1 | 7/2003 | Chen |
| 2003/0135182 A1 | 7/2003 | Woon |
| 2003/0139712 A1 | 7/2003 | Dodge et al. |
| 2003/0139715 A1 | 7/2003 | Dodge et al. |
| 2003/0139718 A1 | 7/2003 | Graef et al. |
| 2003/0144642 A1 | 7/2003 | Dopps et al. |
| 2003/0144644 A1 | 7/2003 | Murai |
| 2003/0148684 A1 | 8/2003 | Cramer et al. |
| 2003/0148694 A1 | 8/2003 | Ghiam |
| 2003/0158530 A1 | 8/2003 | Diehl et al. |
| 2003/0158531 A1 | 8/2003 | Chmielewski |
| 2003/0158532 A1 | 8/2003 | Magee |
| 2003/0167045 A1 | 9/2003 | Graef et al. |
| 2003/0171727 A1 | 9/2003 | Graef et al. |
| 2003/0208175 A1 | 11/2003 | Gross et al. |
| 2003/0225385 A1 | 12/2003 | Glaug et al. |
| 2003/0233082 A1 | 12/2003 | Kline |
| 2003/0236512 A1 | 12/2003 | Baker |
| 2004/0019338 A1 | 1/2004 | Litvay et al. |
| 2004/0022998 A1 | 2/2004 | Miyamoto et al. |
| 2004/0033750 A1 | 2/2004 | Everett et al. |
| 2004/0063367 A1 | 4/2004 | Dodge et al. |
| 2004/0064113 A1 | 4/2004 | Erdman |
| 2004/0064115 A1 | 4/2004 | Arora et al. |
| 2004/0064116 A1 | 4/2004 | Arora et al. |
| 2004/0064125 A1 | 4/2004 | Justmann et al. |
| 2004/0065420 A1 | 4/2004 | Graef et al. |
| 2004/0082928 A1 | 4/2004 | Pesce et al. |
| 2004/0097895 A1 | 5/2004 | Busam |
| 2004/0122411 A1 | 6/2004 | Hancock-cooke |
| 2004/0127131 A1 | 7/2004 | Potnis |
| 2004/0127871 A1 | 7/2004 | Odorzynski et al. |
| 2004/0127872 A1 | 7/2004 | Petryk |
| 2004/0134596 A1 | 7/2004 | Rosati et al. |
| 2004/0138633 A1 | 7/2004 | Mishima et al. |
| 2004/0147890 A1 | 7/2004 | Nakahata et al. |
| 2004/0158212 A1 | 8/2004 | Ponomarenko |
| 2004/0162536 A1 | 8/2004 | Becker |
| 2004/0167486 A1 | 8/2004 | Busam |
| 2004/0167489 A1 | 8/2004 | Kellenberger et al. |
| 2004/0170813 A1 | 9/2004 | Digiacomantonio |
| 2004/0193127 A1 | 9/2004 | Hansson et al. |
| 2004/0215160 A1 | 10/2004 | Chmielewski et al. |
| 2004/0220541 A1 | 11/2004 | Suzuki et al. |
| 2004/0225271 A1 | 11/2004 | Datta et al. |
| 2004/0231065 A1 | 11/2004 | Daniel et al. |
| 2004/0236299 A1 | 11/2004 | Tsang et al. |
| 2004/0236455 A1 | 11/2004 | Woltman et al. |
| 2004/0243078 A1 | 12/2004 | Guidotti et al. |
| 2004/0249355 A1 | 12/2004 | Tanio |
| 2004/0260259 A1 | 12/2004 | Baker |
| 2005/0001929 A1 | 1/2005 | Ochial et al. |

(56) References Cited

U.S. PATENT DOCUMENTS

| | | |
|---|---|---|
| 2005/0004543 A1 | 1/2005 | Schroer et al. |
| 2005/0004548 A1 | 1/2005 | Otsubo et al. |
| 2005/0008839 A1 | 1/2005 | Cramer |
| 2005/0018258 A1 | 1/2005 | Miyagi et al. |
| 2005/0038401 A1 | 2/2005 | Suzuki et al. |
| 2005/0070867 A1 | 3/2005 | Beruda et al. |
| 2005/0085783 A1 | 4/2005 | Komatsu et al. |
| 2005/0085784 A1 | 4/2005 | Leminh et al. |
| 2005/0090789 A1 | 4/2005 | Graef et al. |
| 2005/0101929 A1 | 5/2005 | Waksmundzki et al. |
| 2005/0137543 A1 | 6/2005 | Underhill et al. |
| 2005/0148258 A1 | 7/2005 | Chakravarty et al. |
| 2005/0148961 A1 | 7/2005 | Sosalla |
| 2005/0148990 A1 | 7/2005 | Shimoe et al. |
| 2005/0154363 A1 | 7/2005 | Minato et al. |
| 2005/0159720 A1 | 7/2005 | Gentilcore |
| 2005/0165208 A1 | 7/2005 | Popp et al. |
| 2005/0171499 A1 | 8/2005 | Nigam et al. |
| 2005/0176910 A1 | 8/2005 | Jaworek et al. |
| 2005/0203475 A1 | 9/2005 | Lavon et al. |
| 2005/0215752 A1 | 9/2005 | Popp et al. |
| 2005/0217791 A1 | 10/2005 | Costello |
| 2005/0229543 A1 | 10/2005 | Tippey |
| 2005/0234414 A1 | 10/2005 | Liu |
| 2005/0245684 A1 | 11/2005 | Daniel et al. |
| 2005/0288645 A1 | 12/2005 | Lavon |
| 2005/0288646 A1 | 12/2005 | Lavon |
| 2006/0004334 A1 | 1/2006 | Schlinz et al. |
| 2006/0021695 A1 | 2/2006 | Blessing |
| 2006/0024433 A1 | 2/2006 | Blessing |
| 2006/0069367 A1 | 3/2006 | Waksmundzki et al. |
| 2006/0069371 A1 | 3/2006 | Ohashi |
| 2006/0073969 A1 | 4/2006 | Torii et al. |
| 2006/0081348 A1 | 4/2006 | Graef et al. |
| 2006/0129114 A1 | 6/2006 | Mason et al. |
| 2006/0142724 A1 | 6/2006 | Watanabe et al. |
| 2006/0155057 A1 | 7/2006 | Hermeling et al. |
| 2006/0155254 A1 | 7/2006 | Sanz et al. |
| 2006/0167215 A1 | 7/2006 | Hermeling et al. |
| 2006/0177647 A1 | 8/2006 | Schmidt |
| 2006/0178071 A1 | 8/2006 | Schmidt et al. |
| 2006/0184146 A1 | 8/2006 | Suzuki |
| 2006/0184149 A1 | 8/2006 | Kasai et al. |
| 2006/0189954 A1 | 8/2006 | Kudo |
| 2006/0202380 A1 | 9/2006 | Bentley et al. |
| 2006/0206091 A1 | 9/2006 | Cole et al. |
| 2006/0211828 A1 | 9/2006 | Daniel et al. |
| 2006/0240229 A1 | 10/2006 | Ehrnsperger et al. |
| 2006/0264860 A1 | 11/2006 | Lavon |
| 2006/0264861 A1 | 11/2006 | Lavon et al. |
| 2006/0271010 A1 | 11/2006 | Lavon |
| 2007/0027436 A1 | 2/2007 | Nakagawa et al. |
| 2007/0032770 A1 | 2/2007 | Lavon et al. |
| 2007/0043191 A1 | 2/2007 | Hermeling et al. |
| 2007/0043330 A1 | 2/2007 | Lankhof |
| 2007/0044903 A1 | 3/2007 | Wisneski et al. |
| 2007/0049892 A1 | 3/2007 | Lord et al. |
| 2007/0049897 A1 | 3/2007 | Lavon et al. |
| 2007/0073253 A1 | 3/2007 | Miyama et al. |
| 2007/0078422 A1 | 4/2007 | Glaug et al. |
| 2007/0083175 A1 | 4/2007 | Van Himbergen et al. |
| 2007/0088308 A1 | 4/2007 | Ehrnsperger et al. |
| 2007/0093164 A1 | 4/2007 | Nakaoka |
| 2007/0093767 A1 | 4/2007 | Carlucci et al. |
| 2007/0100307 A1 | 5/2007 | Nomoto et al. |
| 2007/0118087 A1 | 5/2007 | Flohr |
| 2007/0123834 A1 | 5/2007 | Mcdowall et al. |
| 2007/0156108 A1 | 7/2007 | Becker et al. |
| 2007/0156110 A1 | 7/2007 | Thyfault |
| 2007/0167928 A1 | 7/2007 | Becker et al. |
| 2007/0179464 A1 | 8/2007 | Becker et al. |
| 2007/0179469 A1 | 8/2007 | Takahashi et al. |
| 2007/0191798 A1 | 8/2007 | Glaug et al. |
| 2007/0219521 A1 | 9/2007 | Hird |
| 2007/0219523 A1 | 9/2007 | Bruun et al. |
| 2007/0239125 A9 | 10/2007 | Erdman et al. |
| 2007/0244455 A1 | 10/2007 | Hansson et al. |
| 2007/0246147 A1 | 10/2007 | Venturino et al. |
| 2007/0255245 A1 | 11/2007 | Asp et al. |
| 2007/0282288 A1 | 12/2007 | Noda et al. |
| 2007/0282290 A1 | 12/2007 | Cole et al. |
| 2007/0282291 A1 | 12/2007 | Cole et al. |
| 2008/0027402 A1 | 1/2008 | Schmidt et al. |
| 2008/0032035 A1 | 2/2008 | Schmidt et al. |
| 2008/0091159 A1 | 4/2008 | Carlucci et al. |
| 2008/0119810 A1 | 5/2008 | Kuroda et al. |
| 2008/0125735 A1 | 5/2008 | Busam |
| 2008/0132864 A1 | 6/2008 | Lawson et al. |
| 2008/0208154 A1 | 8/2008 | Oetjen |
| 2008/0221538 A1 | 9/2008 | Zhao |
| 2008/0221539 A1 | 9/2008 | Zhao |
| 2008/0228158 A1 | 9/2008 | Sue et al. |
| 2008/0262459 A1 | 10/2008 | Kamoto et al. |
| 2008/0268194 A1 | 10/2008 | Kim et al. |
| 2008/0274227 A1 | 11/2008 | Boatman et al. |
| 2008/0281287 A1 | 11/2008 | Marcelo et al. |
| 2008/0294140 A1 | 11/2008 | Ecker et al. |
| 2008/0312617 A1 | 12/2008 | Hundorf |
| 2008/0312618 A1 | 12/2008 | Hundorf et al. |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf |
| 2008/0312623 A1 | 12/2008 | Hundorf et al. |
| 2008/0312624 A1 | 12/2008 | Hundorf |
| 2008/0312625 A1 | 12/2008 | Hundorf et al. |
| 2008/0312627 A1 | 12/2008 | Takeuchi et al. |
| 2008/0312628 A1 | 12/2008 | Hundorf et al. |
| 2009/0023848 A1 | 1/2009 | Ahmed et al. |
| 2009/0056867 A1 | 3/2009 | Moriura et al. |
| 2009/0058994 A1 | 3/2009 | Kao et al. |
| 2009/0062760 A1 | 3/2009 | Wright et al. |
| 2009/0112173 A1 | 4/2009 | Bissah et al. |
| 2009/0112175 A1 | 4/2009 | Bissah et al. |
| 2009/0157022 A1 | 6/2009 | Macdonald et al. |
| 2009/0192035 A1 | 7/2009 | Stueven et al. |
| 2009/0240220 A1 | 9/2009 | Macdonald et al. |
| 2009/0247977 A1 | 10/2009 | Takeuchi |
| 2009/0258994 A1 | 10/2009 | Stueven et al. |
| 2009/0270825 A1 | 10/2009 | Wciorka et al. |
| 2009/0298963 A1 | 12/2009 | Matsumoto et al. |
| 2009/0299312 A1 | 12/2009 | Macdonald et al. |
| 2009/0306618 A1 | 12/2009 | Kudo et al. |
| 2009/0318884 A1 | 12/2009 | Meyer et al. |
| 2009/0326494 A1 | 12/2009 | Uchida et al. |
| 2010/0051166 A1 | 3/2010 | Hundorf |
| 2010/0062165 A1 | 3/2010 | Suzuki et al. |
| 2010/0062934 A1 | 3/2010 | Suzuki et al. |
| 2010/0063470 A1 | 3/2010 | Suzuki et al. |
| 2010/0068520 A1 | 3/2010 | Stueven |
| 2010/0100065 A1 | 4/2010 | De Angelis et al. |
| 2010/0115237 A1 | 5/2010 | Brewer et al. |
| 2010/0121296 A1 | 5/2010 | Noda et al. |
| 2010/0137773 A1 | 6/2010 | Gross et al. |
| 2010/0137823 A1 | 6/2010 | Corneliusson et al. |
| 2010/0198179 A1 | 8/2010 | Noda et al. |
| 2010/0228210 A1 | 9/2010 | Busam |
| 2010/0228215 A1 | 9/2010 | Ponomarenko et al. |
| 2010/0241096 A1 | 9/2010 | Lavon et al. |
| 2010/0241097 A1 | 9/2010 | Nigam et al. |
| 2010/0262099 A1 | 10/2010 | Klofta |
| 2010/0262104 A1 | 10/2010 | Carlucci et al. |
| 2010/0274208 A1 | 10/2010 | Gabrielii et al. |
| 2010/0274210 A1 | 10/2010 | Noda et al. |
| 2010/0305337 A1 | 12/2010 | Mueller et al. |
| 2010/0305537 A1 | 12/2010 | Ashton |
| 2010/0312208 A1 | 12/2010 | Bond et al. |
| 2010/0324521 A1 | 12/2010 | Mukai et al. |
| 2010/0324523 A1 | 12/2010 | Mukai et al. |
| 2011/0041999 A1 | 2/2011 | Hundorf et al. |
| 2011/0046591 A1 | 2/2011 | Warner |
| 2011/0060301 A1 | 3/2011 | Nishikawa et al. |
| 2011/0060303 A1 | 3/2011 | Bissah et al. |
| 2011/0066127 A1 | 3/2011 | Kuwano et al. |

(56) References Cited

U.S. PATENT DOCUMENTS

| | | |
|---|---|---|
| 2011/0071486 A1 | 3/2011 | Harada et al. |
| 2011/0092944 A1 | 4/2011 | Sagisaka et al. |
| 2011/0112498 A1 | 5/2011 | Nhan et al. |
| 2011/0125120 A1 | 5/2011 | Nishitani et al. |
| 2011/0130732 A1 | 6/2011 | Jackels et al. |
| 2011/0130737 A1 | 6/2011 | Sagisaka et al. |
| 2011/0137276 A1 | 6/2011 | Yoshikawa |
| 2011/0144602 A1 | 6/2011 | Long |
| 2011/0144604 A1 | 6/2011 | Noda et al. |
| 2011/0144606 A1 | 6/2011 | Nandrea et al. |
| 2011/0152813 A1 | 6/2011 | Ellingson |
| 2011/0166540 A1 | 7/2011 | Yang |
| 2011/0172630 A1 | 7/2011 | Nomoto et al. |
| 2011/0174430 A1 | 7/2011 | Zhao et al. |
| 2011/0196330 A1 | 8/2011 | Hammons |
| 2011/0208147 A1 | 8/2011 | Kawakami et al. |
| 2011/0250413 A1 | 10/2011 | Lu |
| 2011/0268932 A1 | 11/2011 | Catalan |
| 2011/0274834 A1 | 11/2011 | Brown et al. |
| 2011/0288513 A1 | 11/2011 | Hundorf et al. |
| 2011/0288514 A1 | 11/2011 | Kuroda et al. |
| 2011/0295222 A1 | 12/2011 | Becker et al. |
| 2011/0319846 A1 | 12/2011 | Rinnert et al. |
| 2011/0319848 A1 | 12/2011 | Mckiernan |
| 2011/0319851 A1 | 12/2011 | Kudo et al. |
| 2012/0004633 A1 | 1/2012 | R. Marcelo |
| 2012/0016326 A1 | 1/2012 | Brennan et al. |
| 2012/0022479 A1 | 1/2012 | Cotton |
| 2012/0035566 A1 | 2/2012 | Sagisaka et al. |
| 2012/0035572 A1 | 2/2012 | Ichikawa et al. |
| 2012/0035576 A1 | 2/2012 | Ichikawa et al. |
| 2012/0041405 A1 | 2/2012 | Alkmin et al. |
| 2012/0064792 A1 | 3/2012 | Bauduin |
| 2012/0071848 A1 | 3/2012 | Zhang et al. |
| 2012/0136329 A1 | 5/2012 | Carney |
| 2012/0165771 A1 | 6/2012 | Ruman et al. |
| 2012/0165776 A1 | 6/2012 | Mcgregor |
| 2012/0170779 A1 | 7/2012 | Hildebrandt |
| 2012/0175056 A1 | 7/2012 | Tsang et al. |
| 2012/0184934 A1 | 7/2012 | Venturino et al. |
| 2012/0220972 A1 | 8/2012 | Kawamura et al. |
| 2012/0232514 A1 | 9/2012 | Baker et al. |
| 2012/0238977 A1 | 9/2012 | Oku et al. |
| 2012/0253306 A1 | 10/2012 | Otsubo et al. |
| 2012/0256750 A1 | 10/2012 | Novak |
| 2012/0271262 A1 | 10/2012 | Venturino et al. |
| 2012/0312491 A1 | 12/2012 | Jackels |
| 2012/0316046 A1 | 12/2012 | Jackels et al. |
| 2012/0316523 A1 | 12/2012 | Hippe |
| 2012/0316526 A1 | 12/2012 | Rosati et al. |
| 2012/0316527 A1 | 12/2012 | Rosati et al. |
| 2012/0316528 A1 | 12/2012 | Kreuzer et al. |
| 2012/0316529 A1 | 12/2012 | Kreuzer et al. |
| 2012/0323195 A1 | 12/2012 | Ehrnsperger et al. |
| 2012/0323201 A1 | 12/2012 | Bissah et al. |
| 2012/0323202 A1 | 12/2012 | Bissah et al. |
| 2013/0035656 A1 | 2/2013 | Moriya et al. |
| 2013/0041334 A1 | 2/2013 | Prioleau et al. |
| 2013/0178811 A1 | 7/2013 | Kikuchi et al. |
| 2013/0211354 A1 | 8/2013 | Tsuji et al. |
| 2013/0211358 A1 | 8/2013 | Kikkawa et al. |
| 2013/0218115 A1 | 8/2013 | Katsuragawa et al. |
| 2013/0226119 A1 | 8/2013 | Katsuragawa et al. |
| 2013/0226120 A1 | 8/2013 | Van De Maele |
| 2013/0245589 A1 | 9/2013 | Toda et al. |
| 2013/0310784 A1 | 11/2013 | Bryant |
| 2013/0331806 A1 | 12/2013 | Rosati et al. |
| 2014/0005622 A1 | 1/2014 | Wirtz |
| 2014/0005623 A1 | 1/2014 | Wirtz et al. |
| 2014/0005625 A1 | 1/2014 | Wirtz et al. |
| 2014/0027066 A1 | 1/2014 | Jackels et al. |
| 2014/0039437 A1 | 2/2014 | Van De Maele |
| 2014/0045683 A1 | 2/2014 | Loick et al. |
| 2014/0102183 A1 | 4/2014 | Agami et al. |
| 2014/0121623 A1 | 5/2014 | Kirby |
| 2014/0135726 A1 | 5/2014 | Busam et al. |
| 2014/0142531 A1 | 5/2014 | Sasayama et al. |
| 2014/0163500 A1 | 6/2014 | Roe et al. |
| 2014/0163501 A1 | 6/2014 | Ehrnsperger et al. |
| 2014/0163502 A1 | 6/2014 | Arizti |
| 2014/0163503 A1 | 6/2014 | Arizti |
| 2014/0163506 A1 | 6/2014 | Roe |
| 2014/0163511 A1 | 6/2014 | Roe et al. |
| 2014/0171893 A1 | 6/2014 | Lawson et al. |
| 2014/0318694 A1 | 10/2014 | Blessing et al. |
| 2014/0324007 A1 | 10/2014 | Hundorf et al. |
| 2014/0324008 A1 | 10/2014 | Hundorf et al. |
| 2015/0065973 A1 | 3/2015 | Roe et al. |
| 2015/0065975 A1 | 3/2015 | Roe |
| 2015/0065976 A1 | 3/2015 | Roe et al. |
| 2015/0065981 A1 | 3/2015 | Roe |
| 2015/0065986 A1 | 3/2015 | Blessing et al. |
| 2015/0080837 A1 | 3/2015 | Rosati et al. |
| 2015/0080839 A1 | 3/2015 | Trapp et al. |
| 2015/0173967 A1 | 6/2015 | Kreuzer |
| 2015/0173968 A1 | 6/2015 | Joseph |
| 2015/0250662 A1 | 9/2015 | Isele et al. |
| 2015/0250663 A1 | 9/2015 | Wagner et al. |
| 2015/0282999 A1 | 10/2015 | Arizti |
| 2018/0008482 A1 | 1/2018 | Roe et al. |
| 2018/0161217 A1 | 6/2018 | Roe et al. |
| 2018/0221221 A1 | 8/2018 | Roe et al. |
| 2019/0231611 A1 | 8/2019 | Roe et al. |
| 2020/0306109 A1 | 10/2020 | Roe et al. |
| 2020/0330290 A1 | 10/2020 | Roe et al. |

FOREIGN PATENT DOCUMENTS

| | | |
|---|---|---|
| CA | 2308961 | 11/2000 |
| CA | 2487027 | 12/2003 |
| CA | 2561521 | 3/2007 |
| CA | 2630713 | 11/2008 |
| CA | 2636673 | 1/2009 |
| CA | 2702001 | 10/2010 |
| CA | 2712563 A1 | 3/2011 |
| CN | 1206341 A | 1/1999 |
| CN | 1238171 A | 12/1999 |
| CN | 2362468 Y | 2/2000 |
| CN | 1328439 A | 12/2001 |
| CN | 1371671 A | 10/2002 |
| CN | 2527254 Y | 12/2002 |
| CN | 2535020 Y | 2/2003 |
| CN | 2548609 Y | 5/2003 |
| CN | 1539391 A | 10/2004 |
| CN | 1939242 | 4/2007 |
| CN | 1942154 A | 4/2007 |
| CN | 101184459 A | 5/2008 |
| CN | 101292930 | 10/2008 |
| CN | 201263750 Y | 7/2009 |
| CN | 201591689 U | 9/2010 |
| CN | 201855366 U | 6/2011 |
| DE | 3205931 C2 | 8/1985 |
| DE | 3608114 | 9/1987 |
| DE | 19732499 | 2/1999 |
| DE | 10204937 | 8/2003 |
| EP | 0083022 | 7/1983 |
| EP | 149880 A2 | 7/1985 |
| EP | 0149880 A2 | 7/1985 |
| EP | 0203289 A2 | 12/1986 |
| EP | 0206208 A1 | 12/1986 |
| EP | 209561 | 1/1987 |
| EP | 297411 | 1/1989 |
| EP | 374542 | 6/1990 |
| EP | 0403832 A1 | 12/1990 |
| EP | 481322 | 4/1992 |
| EP | 530438 A1 | 3/1993 |
| EP | 547847 | 6/1993 |
| EP | 555346 | 8/1993 |
| EP | 559476 A1 | 9/1993 |
| EP | 304957 B2 | 4/1994 |
| EP | 591647 | 4/1994 |
| EP | 597273 | 5/1994 |
| EP | 601610 | 6/1994 |
| EP | 632068 A1 | 1/1995 |

(56) References Cited

FOREIGN PATENT DOCUMENTS

| | | |
|---|---|---|
| EP | 0668066 | 9/1995 |
| EP | 685214 | 12/1995 |
| EP | 687453 | 12/1995 |
| EP | 0689817 A2 | 1/1996 |
| EP | 0691133 | 1/1996 |
| EP | 0700673 A1 | 3/1996 |
| EP | 0394274 | 7/1996 |
| EP | 394274 B2 | 7/1996 |
| EP | 0724418 A1 | 8/1996 |
| EP | 0725613 A1 | 8/1996 |
| EP | 725615 | 8/1996 |
| EP | 0725616 A1 | 8/1996 |
| EP | 0737055 A1 | 10/1996 |
| EP | 758543 | 2/1997 |
| EP | 0761194 | 3/1997 |
| EP | 769284 | 4/1997 |
| EP | 0778762 A1 | 6/1997 |
| EP | 0781537 A1 | 7/1997 |
| EP | 783877 | 7/1997 |
| EP | 787472 | 8/1997 |
| EP | 788874 | 8/1997 |
| EP | 0790839 A1 | 8/1997 |
| EP | 0796068 A2 | 9/1997 |
| EP | 799004 | 10/1997 |
| EP | 822794 | 2/1998 |
| EP | 826351 | 3/1998 |
| EP | 844861 | 6/1998 |
| EP | 863733 | 9/1998 |
| EP | 971751 | 9/1998 |
| EP | 875224 | 11/1998 |
| EP | 0875224 A1 | 11/1998 |
| EP | 880955 | 12/1998 |
| EP | 891758 | 1/1999 |
| EP | 0893115 | 1/1999 |
| EP | 724418 B1 | 3/1999 |
| EP | 725613 B1 | 3/1999 |
| EP | 725616 B1 | 3/1999 |
| EP | 904755 | 3/1999 |
| EP | 0916327 A1 | 5/1999 |
| EP | 925769 | 6/1999 |
| EP | 933074 | 8/1999 |
| EP | 937736 A2 | 8/1999 |
| EP | 941157 | 9/1999 |
| EP | 947549 | 10/1999 |
| EP | 951887 | 10/1999 |
| EP | 0951890 | 10/1999 |
| EP | 2295493 | 10/1999 |
| EP | 2305749 | 10/1999 |
| EP | 2330152 | 10/1999 |
| EP | 953326 | 11/1999 |
| EP | 0978263 A1 | 2/2000 |
| EP | 985397 | 3/2000 |
| EP | 1005847 B1 | 6/2000 |
| EP | 1008333 A3 | 6/2000 |
| EP | 1018999 | 7/2000 |
| EP | 1022008 | 7/2000 |
| EP | 1023884 | 8/2000 |
| EP | 1053729 | 11/2000 |
| EP | 1059072 A2 | 12/2000 |
| EP | 1063954 | 1/2001 |
| EP | 1071388 | 1/2001 |
| EP | 1078618 | 2/2001 |
| EP | 1088537 A2 | 4/2001 |
| EP | 796068 B1 | 5/2001 |
| EP | 752892 B1 | 7/2001 |
| EP | 1116479 A2 | 7/2001 |
| EP | 1132069 | 9/2001 |
| EP | 1173128 | 1/2002 |
| EP | 1184018 | 3/2002 |
| EP | 1199059 | 4/2002 |
| EP | 1199327 A2 | 4/2002 |
| EP | 1208824 | 5/2002 |
| EP | 0793469 | 6/2002 |
| EP | 1210925 | 6/2002 |
| EP | 1224922 | 7/2002 |
| EP | 1225857 | 7/2002 |
| EP | 1253231 | 10/2002 |
| EP | 1262531 A1 | 12/2002 |
| EP | 0737056 | 1/2003 |
| EP | 1275358 | 1/2003 |
| EP | 1275361 | 1/2003 |
| EP | 1293187 | 3/2003 |
| EP | 1339368 | 9/2003 |
| EP | 1374817 | 1/2004 |
| EP | 1388334 | 2/2004 |
| EP | 1402863 | 3/2004 |
| EP | 962208 | 8/2004 |
| EP | 1447066 A1 | 8/2004 |
| EP | 1447067 A1 | 8/2004 |
| EP | 1460987 | 9/2004 |
| EP | 963749 | 11/2004 |
| EP | 1263374 B1 | 11/2004 |
| EP | 1495739 | 1/2005 |
| EP | 1524955 | 4/2005 |
| EP | 1920743 | 4/2005 |
| EP | 1541103 | 6/2005 |
| EP | 1551344 | 7/2005 |
| EP | 1586289 | 10/2005 |
| EP | 1588723 | 10/2005 |
| EP | 1605882 | 12/2005 |
| EP | 1609448 | 12/2005 |
| EP | 1019003 B1 | 1/2006 |
| EP | 1621166 | 2/2006 |
| EP | 1621167 A2 | 2/2006 |
| EP | 1632206 | 3/2006 |
| EP | 1642556 | 4/2006 |
| EP | 1403419 | 5/2006 |
| EP | 1656162 | 5/2006 |
| EP | 1669046 | 6/2006 |
| EP | 1019002 B1 | 8/2006 |
| EP | 1688114 | 8/2006 |
| EP | 2314265 | 8/2006 |
| EP | 1723939 | 11/2006 |
| EP | 1192312 B1 | 12/2006 |
| EP | 1013252 B1 | 1/2007 |
| EP | 1738727 | 1/2007 |
| EP | 1754461 | 2/2007 |
| EP | 1787611 | 5/2007 |
| EP | 1175194 B1 | 6/2007 |
| EP | 1813238 | 8/2007 |
| EP | 1304986 B1 | 11/2007 |
| EP | 1332742 B1 | 6/2008 |
| EP | 2008626 | 12/2008 |
| EP | 2055279 A1 | 5/2009 |
| EP | 2093049 | 8/2009 |
| EP | 2130522 | 12/2009 |
| EP | 1621165 | 4/2010 |
| EP | 1196122 B2 | 11/2011 |
| EP | 2444046 A1 | 4/2012 |
| EP | 2486905 | 8/2012 |
| EP | 2532328 | 12/2012 |
| EP | 2532329 A1 | 12/2012 |
| EP | 2532332 A1 | 12/2012 |
| EP | 2656826 | 10/2013 |
| EP | 2679210 A1 | 1/2014 |
| EP | 2740449 | 6/2014 |
| EP | 2740450 A1 | 6/2014 |
| EP | 2740452 A1 | 6/2014 |
| EP | 2786731 | 10/2014 |
| ES | 2213491 | 8/2004 |
| FR | 2566631 | 1/1986 |
| FR | 2583377 | 12/1986 |
| FR | 2612770 | 9/1988 |
| FR | 2699813 | 7/1994 |
| FR | 2810234 | 12/2001 |
| GB | 1307441 A | 2/1973 |
| GB | 1333081 A | 10/1973 |
| GB | 1513055 A | 6/1978 |
| GB | 2101468 | 1/1983 |
| GB | 2170108 A | 7/1986 |
| GB | 2262873 | 7/1993 |
| GB | 2288540 A | 10/1995 |
| GB | 2354449 A1 | 3/2001 |
| GB | 2452260 A | 3/2009 |

(56) References Cited

FOREIGN PATENT DOCUMENTS

| | | | |
|---|---|---|---|
| GR | 851769 B | 11/1985 |
| IN | 0984KOL1999 | 10/2005 |
| IN | 212479 | 3/2007 |
| IN | 208543 | 8/2007 |
| IN | 0980MUM2009 | 6/2009 |
| JP | 5572928 | 5/1980 |
| JP | 598322 | 1/1984 |
| JP | 63148323 U | 9/1988 |
| JP | 2107250 | 4/1990 |
| JP | 03224481 | 10/1991 |
| JP | 04122256 | 4/1992 |
| JP | 04341368 | 11/1992 |
| JP | 06191505 | 7/1994 |
| JP | 06269475 A | 9/1994 |
| JP | 07124193 | 5/1995 |
| JP | H08504637 A | 5/1996 |
| JP | 08215629 | 8/1996 |
| JP | H10295728 A | 11/1998 |
| JP | 10328232 | 12/1998 |
| JP | 11033056 | 2/1999 |
| JP | 11318980 | 11/1999 |
| JP | 11320742 | 11/1999 |
| JP | 2000232985 A | 8/2000 |
| JP | 2000238161 A | 9/2000 |
| JP | 2001037810 A | 2/2001 |
| JP | 2001046435 A | 2/2001 |
| JP | 2001120597 A | 5/2001 |
| JP | 2001158074 A | 6/2001 |
| JP | 2001178768 A | 7/2001 |
| JP | 2001198157 A | 7/2001 |
| JP | 2001224626 A | 8/2001 |
| JP | 2001277394 A | 10/2001 |
| JP | 03420481 | 11/2001 |
| JP | 2001321397 A | 11/2001 |
| JP | 2001353174 A | 12/2001 |
| JP | 2002052042 A | 2/2002 |
| JP | 2002065718 A | 3/2002 |
| JP | 2002113800 A | 4/2002 |
| JP | 2002165832 A | 6/2002 |
| JP | 2002165836 A | 6/2002 |
| JP | 2002178429 A | 6/2002 |
| JP | 2002272769 A | 9/2002 |
| JP | 2002320641 A | 11/2002 |
| JP | 2002325792 A | 11/2002 |
| JP | 2002325799 A | 11/2002 |
| JP | 2002369841 A | 12/2002 |
| JP | 2003126140 A | 5/2003 |
| JP | 2003153955 A | 5/2003 |
| JP | 2003265523 A | 9/2003 |
| JP | 2003265524 A | 9/2003 |
| JP | 2003275237 A | 9/2003 |
| JP | 2003325563 A | 11/2003 |
| JP | 2004089269 A | 3/2004 |
| JP | 03566012 | 6/2004 |
| JP | 03568146 | 6/2004 |
| JP | 03616077 | 11/2004 |
| JP | 2004337314 A | 12/2004 |
| JP | 2004337385 A | 12/2004 |
| JP | 2004350864 A | 12/2004 |
| JP | 03640475 | 1/2005 |
| JP | 2005000312 A | 1/2005 |
| JP | 03660816 | 3/2005 |
| JP | 03676219 | 5/2005 |
| JP | 2005118339 A | 5/2005 |
| JP | 03688403 | 6/2005 |
| JP | 03705943 | 8/2005 |
| JP | 03719819 | 9/2005 |
| JP | 03724963 | 9/2005 |
| JP | 03725008 | 9/2005 |
| JP | 03737376 | 11/2005 |
| JP | 2006014792 A | 1/2006 |
| JP | 03781617 | 3/2006 |
| JP | 2006110329 A | 4/2006 |
| JP | 2006513824 A | 4/2006 |
| JP | 03801449 | 5/2006 |
| JP | 2006116036 A | 5/2006 |
| JP | 03850102 | 9/2006 |
| JP | 03850207 | 9/2006 |
| JP | 03856941 | 9/2006 |
| JP | 03868628 | 10/2006 |
| JP | 03874499 | 11/2006 |
| JP | 03877702 | 11/2006 |
| JP | 2006325639 A | 12/2006 |
| JP | 2006346021 A | 12/2006 |
| JP | 03904356 | 1/2007 |
| JP | 2007007455 A | 1/2007 |
| JP | 2007007456 A | 1/2007 |
| JP | 2007500048 A | 1/2007 |
| JP | 03926042 | 3/2007 |
| JP | 03934855 | 3/2007 |
| JP | 2007089906 A | 4/2007 |
| JP | 2007105198 A | 4/2007 |
| JP | 2007130504 A | 5/2007 |
| JP | 2007152033 A | 6/2007 |
| JP | 2007159632 A | 6/2007 |
| JP | 03986210 | 7/2007 |
| JP | 03986222 | 7/2007 |
| JP | 2007167453 A | 7/2007 |
| JP | 2007175515 A | 7/2007 |
| JP | 2007195665 A | 8/2007 |
| JP | 2007267763 A | 10/2007 |
| JP | 2007275491 A | 10/2007 |
| JP | 04035341 | 11/2007 |
| JP | 04058281 | 12/2007 |
| JP | 04061086 | 12/2007 |
| JP | 04092319 | 3/2008 |
| JP | 2008080150 A | 4/2008 |
| JP | 2008093289 A | 4/2008 |
| JP | 04124322 | 5/2008 |
| JP | 2008119081 A | 5/2008 |
| JP | 2008136739 A | 6/2008 |
| JP | 2008136877 A | 6/2008 |
| JP | 04148594 | 7/2008 |
| JP | 04148620 | 7/2008 |
| JP | 2008154606 A | 7/2008 |
| JP | 04162609 | 8/2008 |
| JP | 04162637 | 8/2008 |
| JP | 04166923 | 8/2008 |
| JP | 04167406 | 8/2008 |
| JP | 04173723 | 8/2008 |
| JP | 4177770 B2 | 8/2008 |
| JP | 04190675 | 9/2008 |
| JP | 04190693 | 9/2008 |
| JP | 04208338 | 10/2008 |
| JP | 2008246089 A | 10/2008 |
| JP | 04230971 | 12/2008 |
| JP | 2008295475 A | 12/2008 |
| JP | 2008295713 A | 12/2008 |
| JP | 04261593 | 2/2009 |
| JP | 2009028186 A | 2/2009 |
| JP | 2009100846 A | 5/2009 |
| JP | 2009112590 A | 5/2009 |
| JP | 2009136601 A | 6/2009 |
| JP | 2009142401 A | 7/2009 |
| JP | 04322228 | 8/2009 |
| JP | 2009201878 A | 9/2009 |
| JP | 04392936 | 10/2009 |
| JP | 2009232987 A | 10/2009 |
| JP | 2009261777 A | 11/2009 |
| JP | 2009291473 A | 12/2009 |
| JP | 2009297048 A | 12/2009 |
| JP | 2010017342 A | 1/2010 |
| JP | 04458702 | 2/2010 |
| JP | 04459013 | 2/2010 |
| JP | 2010022560 A | 2/2010 |
| JP | 04481325 | 3/2010 |
| JP | 2010046155 A | 3/2010 |
| JP | 2010051654 A | 3/2010 |
| JP | 2010063814 A | 3/2010 |
| JP | 2010063944 A | 3/2010 |
| JP | 04492957 | 4/2010 |
| JP | 2010068954 A | 4/2010 |
| JP | 2010075462 A | 4/2010 |
| JP | 2010082059 A | 4/2010 |

(56) References Cited

FOREIGN PATENT DOCUMENTS

| | | |
|---|---|---|
| JP | 2010099531 A | 5/2010 |
| JP | 2010104545 A | 5/2010 |
| JP | 2010104547 A | 5/2010 |
| JP | 2010110535 A | 5/2010 |
| JP | 2010119454 A | 6/2010 |
| JP | 2010119605 A | 6/2010 |
| JP | 2010119743 A | 6/2010 |
| JP | 2010131131 A | 6/2010 |
| JP | 2010131132 A | 6/2010 |
| JP | 2010131206 A | 6/2010 |
| JP | 2010131297 A | 6/2010 |
| JP | 2010136917 A | 6/2010 |
| JP | 2010136973 A | 6/2010 |
| JP | 04540563 | 7/2010 |
| JP | 4577766 B2 | 9/2010 |
| JP | 04587947 | 9/2010 |
| JP | 2010194124 A | 9/2010 |
| JP | 2010194218 A | 9/2010 |
| JP | 2010201093 A | 9/2010 |
| JP | 2010221067 A | 10/2010 |
| JP | 04620299 | 11/2010 |
| JP | 04627472 | 11/2010 |
| JP | 04627473 | 11/2010 |
| JP | 04638087 | 12/2010 |
| JP | 04652626 | 12/2010 |
| JP | 2010273842 A | 12/2010 |
| JP | 2010284418 A | 12/2010 |
| JP | 2011000480 A | 1/2011 |
| JP | 2012010951 A | 1/2011 |
| JP | 2011030700 A | 2/2011 |
| JP | 04693574 | 3/2011 |
| JP | 2011067484 A | 4/2011 |
| JP | 2011072451 A | 4/2011 |
| JP | 2011072720 A | 4/2011 |
| JP | 2011104014 A | 6/2011 |
| JP | 2011104122 A | 6/2011 |
| JP | 2011120661 A | 6/2011 |
| JP | 2011125360 A | 6/2011 |
| JP | 2011125537 A | 6/2011 |
| JP | 04776516 | 7/2011 |
| JP | 2011130797 A | 7/2011 |
| JP | 2011130799 A | 7/2011 |
| JP | 2011156031 | 8/2011 |
| JP | 2011156032 A | 8/2011 |
| JP | 2011156070 A | 8/2011 |
| JP | 2011156254 A | 8/2011 |
| JP | 04824882 | 9/2011 |
| JP | 4850272 B2 | 10/2011 |
| JP | 04855533 | 11/2011 |
| JP | 2011235115 A | 11/2011 |
| JP | 2011239858 A | 12/2011 |
| JP | 2011240050 A | 12/2011 |
| JP | 04931572 | 2/2012 |
| JP | 04953618 | 3/2012 |
| JP | 04969437 | 4/2012 |
| JP | 04969640 | 4/2012 |
| JP | 4971491 B2 | 4/2012 |
| JP | 04974524 | 4/2012 |
| JP | 04979780 | 4/2012 |
| JP | 04937225 | 5/2012 |
| JP | 05016020 | 6/2012 |
| JP | 05027364 | 6/2012 |
| JP | 5715806 B2 | 6/2012 |
| JP | 2012115378 A | 6/2012 |
| JP | 05031082 | 7/2012 |
| JP | 05042351 | 7/2012 |
| JP | 05043569 | 7/2012 |
| JP | 05043591 | 7/2012 |
| JP | 05046488 | 7/2012 |
| JP | 2012125452 A | 7/2012 |
| JP | 2012125625 A | 7/2012 |
| JP | 2012130736 A | 7/2012 |
| JP | 05053765 | 8/2012 |
| JP | 05070275 | 8/2012 |
| JP | 2012152482 A | 8/2012 |
| JP | 05079931 B1 | 9/2012 |
| JP | 05080189 | 9/2012 |
| JP | 05084442 | 9/2012 |
| JP | 05084476 | 9/2012 |
| JP | 5085770 B2 | 9/2012 |
| JP | 05089269 | 9/2012 |
| JP | 2012179286 A | 9/2012 |
| JP | 05113146 | 10/2012 |
| JP | 2012205924 A | 10/2012 |
| JP | 05129536 | 11/2012 |
| JP | 2012223230 A | 11/2012 |
| JP | 2012223231 A | 11/2012 |
| JP | 05105884 | 12/2012 |
| JP | 2013111127 A | 6/2013 |
| KR | 20010005620 A | 1/2001 |
| KR | 20020035634 A | 5/2002 |
| KR | 20080028771 A | 4/2008 |
| RU | 2261079 C2 | 9/2005 |
| RU | 2302849 C2 | 7/2007 |
| SE | 9400916 | 3/1994 |
| SE | 9704893 | 12/1994 |
| WO | 9015830 A1 | 12/1990 |
| WO | 9219198 A1 | 11/1992 |
| WO | 9321237 A1 | 10/1993 |
| WO | 9321879 A1 | 11/1993 |
| WO | 9510996 A1 | 4/1995 |
| WO | 9511652 A1 | 5/1995 |
| WO | 9514453 | 6/1995 |
| WO | 9515139 A1 | 6/1995 |
| WO | 9516424 A1 | 6/1995 |
| WO | 9516746 A1 | 6/1995 |
| WO | 9519753 A1 | 7/1995 |
| WO | 9521596 A1 | 8/1995 |
| WO | 9524173 A2 | 9/1995 |
| WO | 9526209 A1 | 10/1995 |
| WO | 9529657 A1 | 11/1995 |
| WO | 9532698 A1 | 12/1995 |
| WO | 9534329 A1 | 12/1995 |
| WO | 9616624 | 6/1996 |
| WO | 9619173 A1 | 6/1996 |
| WO | 9629967 A1 | 10/1996 |
| WO | 9711659 A1 | 4/1997 |
| WO | 9717922 A1 | 5/1997 |
| WO | 9724096 A1 | 7/1997 |
| WO | 9816179 A1 | 4/1998 |
| WO | 9816180 A1 | 4/1998 |
| WO | 9843684 A1 | 10/1998 |
| WO | 9913813 A1 | 3/1999 |
| WO | 9934841 A1 | 7/1999 |
| WO | 9951178 A1 | 10/1999 |
| WO | 0032147 A1 | 6/2000 |
| WO | 2000059430 A1 | 10/2000 |
| WO | 2001015647 | 3/2001 |
| WO | 2002032962 A2 | 4/2002 |
| WO | 2002064877 | 8/2002 |
| WO | 2002067809 A2 | 9/2002 |
| WO | 2003009794 | 2/2003 |
| WO | 2003039402 | 5/2003 |
| WO | 2003053297 | 7/2003 |
| WO | 2003079946 | 10/2003 |
| WO | 2003101622 | 12/2003 |
| WO | 2003105738 | 12/2003 |
| WO | 2004021946 A1 | 3/2004 |
| WO | 2004049995 A1 | 6/2004 |
| WO | 2004071539 A3 | 8/2004 |
| WO | 2004084784 A1 | 10/2004 |
| WO | 2004105664 A1 | 12/2004 |
| WO | 2005018694 A1 | 3/2005 |
| WO | 2005087164 A1 | 9/2005 |
| WO | 2006059922 A1 | 6/2006 |
| WO | 2006062258 A2 | 6/2006 |
| WO | 2006066029 A1 | 6/2006 |
| WO | 2006076281 A1 | 7/2006 |
| WO | 2006083584 | 8/2006 |
| WO | 2006104024 A1 | 10/2006 |
| WO | 2006134904 A1 | 12/2006 |
| WO | 2006134906 A1 | 12/2006 |
| WO | 2007000315 A1 | 1/2007 |
| WO | 2007046052 A1 | 4/2007 |

(56) References Cited

FOREIGN PATENT DOCUMENTS

| | | |
|---|---|---|
| WO | 2007047598 A1 | 4/2007 |
| WO | 2007049725 A1 | 5/2007 |
| WO | 2007061035 A1 | 5/2007 |
| WO | 2007141744 A1 | 12/2007 |
| WO | 2007142145 A1 | 12/2007 |
| WO | 2007148502 A1 | 12/2007 |
| WO | 2008018922 A1 | 2/2008 |
| WO | 2008065945 A1 | 6/2008 |
| WO | 2008146749 A1 | 12/2008 |
| WO | 2008155699 A1 | 12/2008 |
| WO | 2009004941 A1 | 1/2009 |
| WO | 2009005431 A1 | 1/2009 |
| WO | 2009041223 A1 | 4/2009 |
| WO | 2009096108 A1 | 8/2009 |
| WO | 2009107435 A1 | 9/2009 |
| WO | 2009122830 A1 | 10/2009 |
| WO | 2009139248 A1 | 11/2009 |
| WO | 2009139255 A1 | 11/2009 |
| WO | 2009152018 A1 | 12/2009 |
| WO | 2009155264 | 12/2009 |
| WO | 2009155265 | 12/2009 |
| WO | 2010071508 A1 | 6/2010 |
| WO | 2010074319 A1 | 7/2010 |
| WO | 2010107096 A1 | 9/2010 |
| WO | 2010114052 A1 | 10/2010 |
| WO | 2010117015 A1 | 10/2010 |
| WO | 2010118272 A1 | 10/2010 |
| WO | 2011118725 A1 | 9/2011 |
| WO | 2011118842 A1 | 9/2011 |
| WO | 2011053044 A3 | 10/2011 |
| WO | 2011145653 A1 | 11/2011 |
| WO | 2011150955 A1 | 12/2011 |
| WO | 2011163582 A1 | 12/2011 |
| WO | 2012002252 A1 | 1/2012 |
| WO | 2012014436 A1 | 2/2012 |
| WO | 2012042908 A1 | 4/2012 |
| WO | 2012043077 A1 | 4/2012 |
| WO | 2012043078 A1 | 4/2012 |
| WO | 2012043082 A1 | 4/2012 |
| WO | 2012052172 A1 | 4/2012 |
| WO | 2012067216 A1 | 5/2012 |
| WO | 2012073499 A1 | 6/2012 |
| WO | 2012074466 A1 | 6/2012 |
| WO | 2012090508 A1 | 7/2012 |
| WO | 2012091016 A1 | 7/2012 |
| WO | 2012101934 A1 | 8/2012 |
| WO | 2012102034 A1 | 8/2012 |
| WO | 2012117764 A1 | 9/2012 |
| WO | 2012117824 A1 | 9/2012 |
| WO | 2012132460 A1 | 10/2012 |
| WO | 2012165327 A1 | 12/2012 |
| WO | 2012170778 A1 | 12/2012 |
| WO | 2012170779 A1 | 12/2012 |
| WO | 2012170781 A1 | 12/2012 |
| WO | 2012170808 A1 | 12/2012 |
| WO | 2012174026 A1 | 12/2012 |
| WO | 2012177400 A1 | 12/2012 |
| WO | 2013001788 A1 | 1/2013 |
| WO | 2013046701 A1 | 4/2013 |
| WO | 2013047268 A1 | 4/2013 |
| WO | 2013060733 A1 | 5/2013 |
| WO | 2013061867 A1 | 5/2013 |
| WO | 2013077074 A1 | 5/2013 |
| WO | 2014023751 A1 | 2/2014 |
| WO | 2014073636 A1 | 5/2014 |
| WO | 2014078247 A2 | 5/2014 |
| WO | 2015005502 | 1/2015 |
| WO | 2015095514 A3 | 9/2015 |

OTHER PUBLICATIONS

All Office Actions, U.S. Appl. No. 14/467,092, filed Aug. 25, 2014.
All Office Actions, U.S. Appl. No. 14/467,095, filed Aug. 25, 2014.
All Office Actions, U.S. Appl. No. 14/467,099, filed Aug. 25, 2014.
All Office Actions, U.S. Appl. No. 14/467,102, filed Aug. 25, 2014.
All Office Actions, U.S. Appl. No. 15/702,778, filed Sep. 13, 2017.
All Office Actions, U.S. Appl. No. 15/894,149, filed Feb. 12, 2018.
All Office Actions, U.S. Appl. No. 15/942,607, filed Apr. 2, 2018.
All Office Actions, U.S. Appl. No. 16/378,640, filed Apr. 9, 2019.
All Office Actions, U.S. Appl. No. 16/903,664, filed Jun. 17, 2020.
All Office Actions, U.S. Appl. No. 16/922,405, filed Jul. 7, 2020.
International Search Report and Written Opinion; Application Ser. No. PCTUS2014/052496; dated Nov. 21, 2014, 19 pages.
Third Party Opposition filed for European Patent Application Ser. No. 14761510.8, Dated May 13, 2019; 12 pages.

* cited by examiner

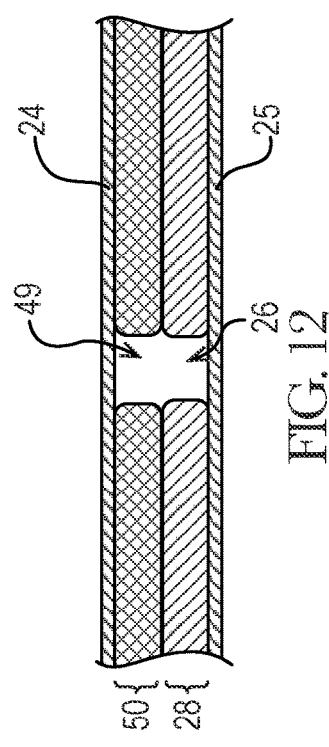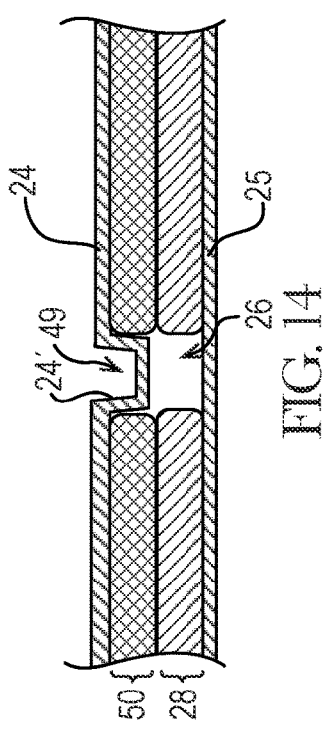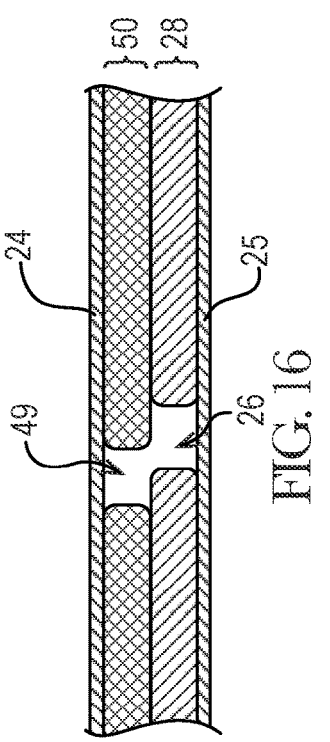
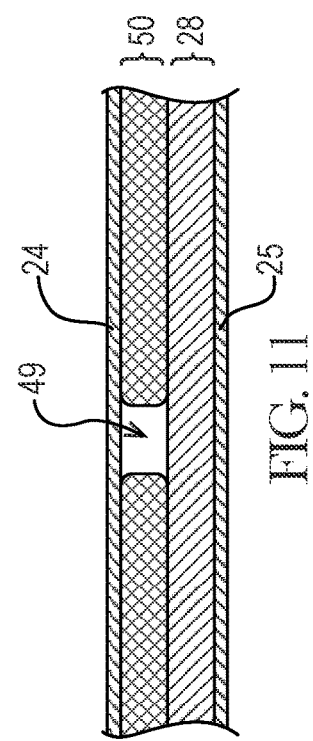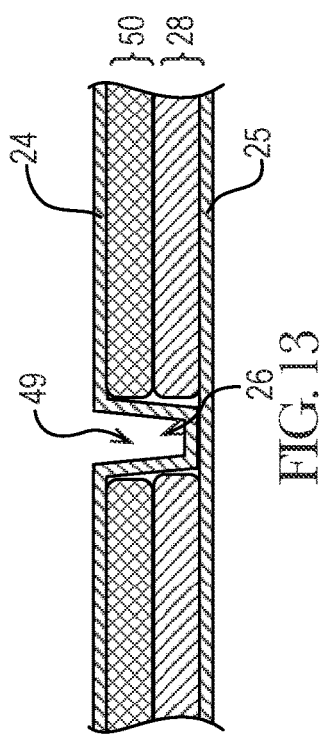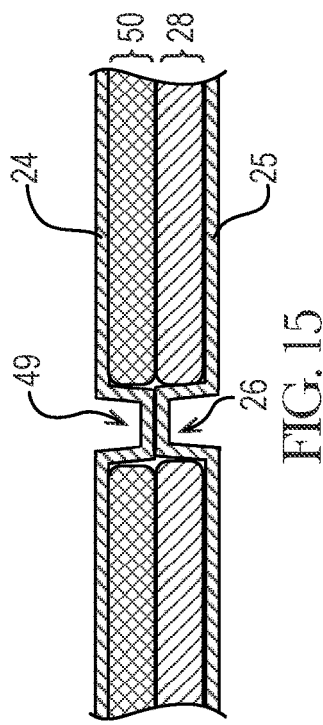

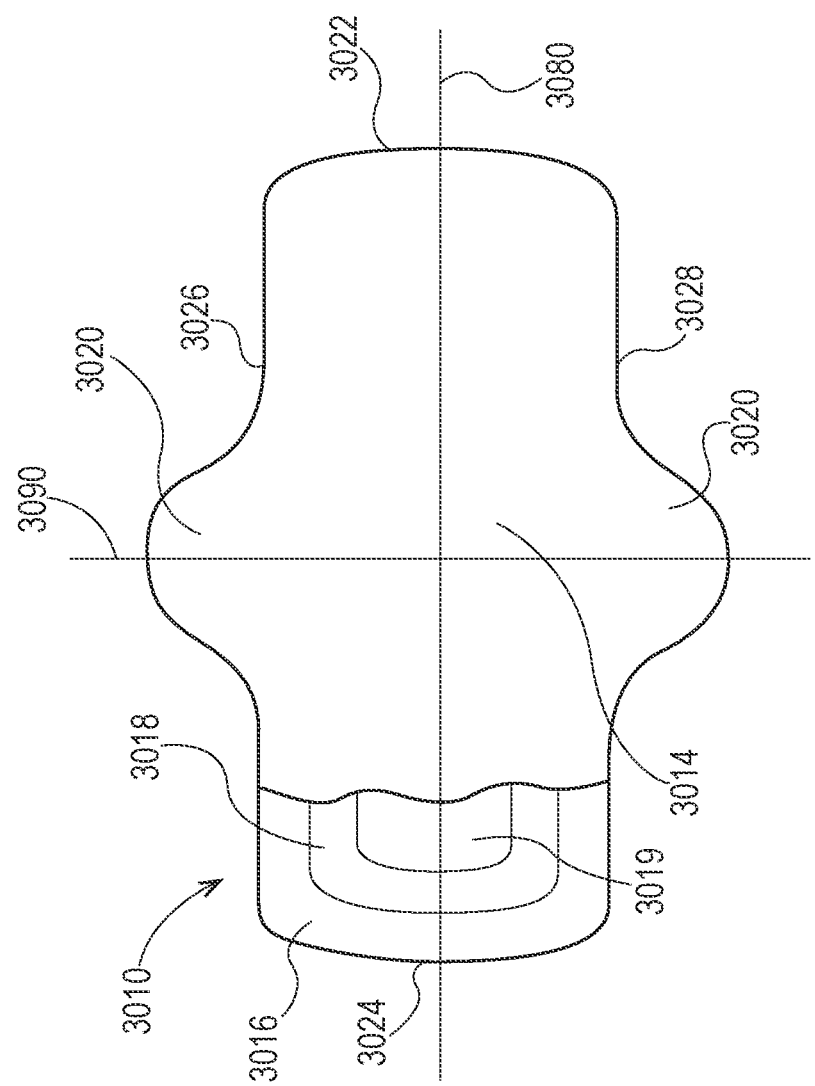

ABSORBENT ARTICLES WITH CHANNELS

CROSS REFERENCE TO RELATED APPLICATIONS

This application is a continuation of, and claims priority under 35 U.S.C. § 120 to, U.S. patent application Ser. No. 16/903,664, filed on Jun. 17, 2020, which is a continuation of, and claims priority under 35 U.S.C. § 120 to, U.S. patent application Ser. No. 15/942,607, filed on Apr. 2, 2018, now U.S. Pat. No. 10,736,794, which is a continuation of, and claims priority under 35 U.S.C. § 120 to, U.S. patent application Ser. No. 14/467,095, filed on Aug. 25, 2014, now U.S. Pat. No. 9,987,176, which claims the benefit, under 35 U.S.C. § 119(e), of U.S. Provisional Patent Application Ser. No. 61/870,391, filed on Aug. 27, 2013, the entire disclosures of which are fully incorporated by reference herein.

FIELD

The present disclosure is generally directed to absorbent articles for personal hygiene. The absorbent articles may each comprise channels.

BACKGROUND

Absorbent articles for personal hygiene are designed to absorb and contain body exudates. These absorbent articles may comprise several layers providing different functions, for example, a topsheet, a backsheet, and an absorbent core disposed between the topsheet and the backsheet, among other layers.

The function of the absorbent core is to absorb and retain the bodily exudates for a prolonged amount of time, for example, overnight for a diaper, minimize re-wet to keep the wearer dry, and avoid soiling of clothes or bed sheets. Some currently marketed absorbent articles comprise an absorbent material which is a blend of comminuted wood pulp (i.e., airfelt) with superabsorbent polymers (SAP) in particulate form, also called absorbent gelling materials (AGM). Absorbent articles having a core consisting essentially of SAP as the absorbent material (so called "airfelt-free" cores) have also been proposed but are less common than traditional mixed cores.

Absorbent articles may also comprise an acquisition layer or system. One function of such a layer or system is to quickly acquire liquids or other bodily exudates and distribute them to the absorbent core in an efficient manner. The acquisition layer or system may comprise one or more layers which may form a unitary layer or may remain as discrete layers. The layers may be attached to each other and may be disposed between the absorbent core and the topsheet. Some absorbent articles may typically comprise leg cuffs which provide improved containment of liquids and other body exudates. Leg cuffs may also be referred to as leg bands, side flaps, barrier cuffs, or elastic cuffs. Usually, each leg cuff comprises one or more elastic strands or elements comprised in the chassis of the diaper, for example, between the topsheet and backsheet in the area of the leg openings to provide an effective seal while the absorbent article is in use. These elasticized elements which may be substantially planar with the chassis of the absorbent article will be referred to herein as gasketing cuffs. It is also usual for the leg cuffs to comprise raised elasticized flaps, herein referred to as barrier leg cuffs, which improve the containment of fluid in the leg-torso joint regions.

Absorbent articles generally have a high absorbent capacity and the absorbent core may expand several times its weight and volume. These increases may cause the absorbent articles to sag in the crotch region as they become saturated with liquid, which may cause the barrier leg cuffs to partially lose contact with the wearer's skin. This may lead to a loss of functionality of the barrier leg cuffs, with the increased possibly of leakage. As the absorbent core expands with other bodily exudates, the acquisition layer or system may undesirably detach or otherwise separate from the absorbent core. Additionally, some absorbent articles are not designed to effectively handle both urine and feces in a single product. Accordingly, performance of the absorbent articles can be undesirable and wearing such absorbent articles can be uncomfortable.

Although various solutions to this problem have been proposed, the field can benefit from additional channel and/or pocket configurations that improve urine and feces management and leakage prevention in absorbent articles and improved comfort for the wearer.

SUMMARY

The present disclosure is directed, in part, to an absorbent article that comprises a liquid permeable material and a liquid impermeable material. The absorbent article comprises an absorbent core disposed at least partially intermediate the liquid permeable material and the liquid impermeable material and comprising an absorbent material. The absorbent material comprises at least 85% of superabsorbent polymers by weight of the absorbent material. The absorbent core defines a first channel substantially free of the superabsorbent polymers and the first channel extends substantially through the thickness of the absorbent material. The absorbent article comprises a liquid management system positioned at least partially intermediate the liquid permeable material and the absorbent core. The liquid management system is substantially free of any superabsorbent polymers defines a second channel. The second channel extends substantially though the thickness of the liquid management system.

The present disclosure is directed, in part, to an absorbent article comprising a liquid permeable material and a liquid impermeable material. The absorbent article comprises an absorbent core disposed at least partially intermediate the liquid permeable material and the liquid impermeable material and comprising an absorbent material. The absorbent material comprises at least 85% of superabsorbent polymers by weight of the absorbent material. The absorbent core defines a first channel substantially free of the superabsorbent polymers and the first channel extends substantially through the thickness of the absorbent material. The absorbent article comprises a liquid management system comprising a first layer and a second layer. The first layer is positioned at least partially intermediate the liquid permeable material and the second layer and the second layer is positioned at least partially intermediate the first layer and the absorbent core. The first layer or the second layer defines a second channel. The liquid management system is substantially free of any superabsorbent polymers.

The present disclosure is directed, in part, to an absorbent article comprising a liquid permeable material, a liquid impermeable material and an absorbent core disposed at least partially intermediate the liquid permeable material and the liquid impermeable material and comprising an absorbent material. The absorbent material comprises superabsorbent polymers. The absorbent article comprises a liquid management system positioned at least partially intermediate the liquid permeable material and the absorbent core. The liquid management system is substantially free of any superabsorbent polymers and comprises cross-linked cellulosic fibers. The liquid management system defines a channel.

The present disclosure is directed, in part, to an absorbent article comprising a liquid permeable material and a liquid impermeable material. The absorbent article comprises an absorbent core disposed at least partially intermediate the liquid permeable material and the liquid impermeable material and comprising an absorbent material. The absorbent material comprises at least 85% of superabsorbent polymers by weight of the absorbent material and the absorbent core defines a first channel substantially free of the superabsorbent polymers. The absorbent article comprises a liquid management system positioned at least partially intermediate the liquid permeable material and the absorbent core. The liquid management system is free of any superabsorbent polymer. The liquid management system defines a second channel defined therein and a portion of the liquid permeable material is recessed into the second channel.

The present disclosure is directed, in part, to an absorbent article comprising a liquid permeable material and a liquid impermeable material. The absorbent article comprises an absorbent core disposed at least partially intermediate the liquid permeable material and the liquid impermeable material and comprising an absorbent material. The absorbent material comprises at least 85% of superabsorbent polymers by weight of the absorbent material and the absorbent core defines a first channel substantially free of the superabsorbent polymers. The absorbent article comprises a first material positioned at least partially intermediate the liquid permeable material and the absorbent core. The first material is substantially free of superabsorbent polymers. The absorbent article comprises a second material positioned intermediate the first material and the absorbent core. The second material is substantially free of any superabsorbent polymers defines a second channel. A portion of the first material is recessed into the second channel.

The present disclosure is directed, in part, to an absorbent article comprising a liquid permeable material and a liquid impermeable material. The absorbent article comprises an absorbent core disposed at least partially intermediate the liquid permeable material and the liquid impermeable material and comprising an absorbent material. The absorbent article comprises a substantially laterally-extending separation element at least partially defining a visual front portion and a visual back portion of the absorbent article. The absorbent article comprises a liquid management system positioned at least partially intermediate the liquid permeable material and the absorbent core. The liquid management system defines a channel formed therein having a physical property. The channel has a first physical property value in the visual front portion and a second physical property value in the visual back portion. The first physical property value of a front portion of the channel is different than the second physical property value of a back portion of the channel.

The present disclosure is directed, in part, to an absorbent article comprising a liquid permeable material and a liquid impermeable material. The absorbent article comprises an absorbent core disposed at least partially intermediate the liquid permeable material and the liquid impermeable material and comprising an absorbent material and a substantially laterally-extending separation element at least partially visually defining a front portion and a back portion of the absorbent article. The absorbent article comprises a liquid management system positioned at least partially intermediate the liquid permeable material and the absorbent core, wherein the liquid management system defines a channel. The channel is positioned in the front portion or the back portion.

The present disclosure is directed, in part, to an absorbent article comprising a liquid permeable material and a liquid impermeable material. The absorbent article comprises an absorbent core disposed at least partially intermediate the liquid permeable material and the liquid impermeable material and comprising an absorbent material. The absorbent core defines a first channel substantially free of the absorbent material and the first channel extends substantially through the thickness of the absorbent material. The absorbent article comprises a substantially laterally-extending separation element at least partially defining a visual front portion and a visual back portion of the absorbent article. The absorbent article comprises a liquid management system positioned at least partially intermediate the liquid permeable material and the absorbent core. The liquid management system comprises a second channel formed therein and overlaps at least a portion of the first channel.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein:

FIGS. 11-26 are partial cross-sectional views of absorbent articles comprising channels in a liquid management system in accordance with various non-limiting embodiments of the present disclosure;

FIG. 41 is a top view of an absorbent article that is a sanitary napkin with some of the layers cut away in accordance with a non-limiting embodiment of the present disclosure.

DETAILED DESCRIPTION

Figure 1:
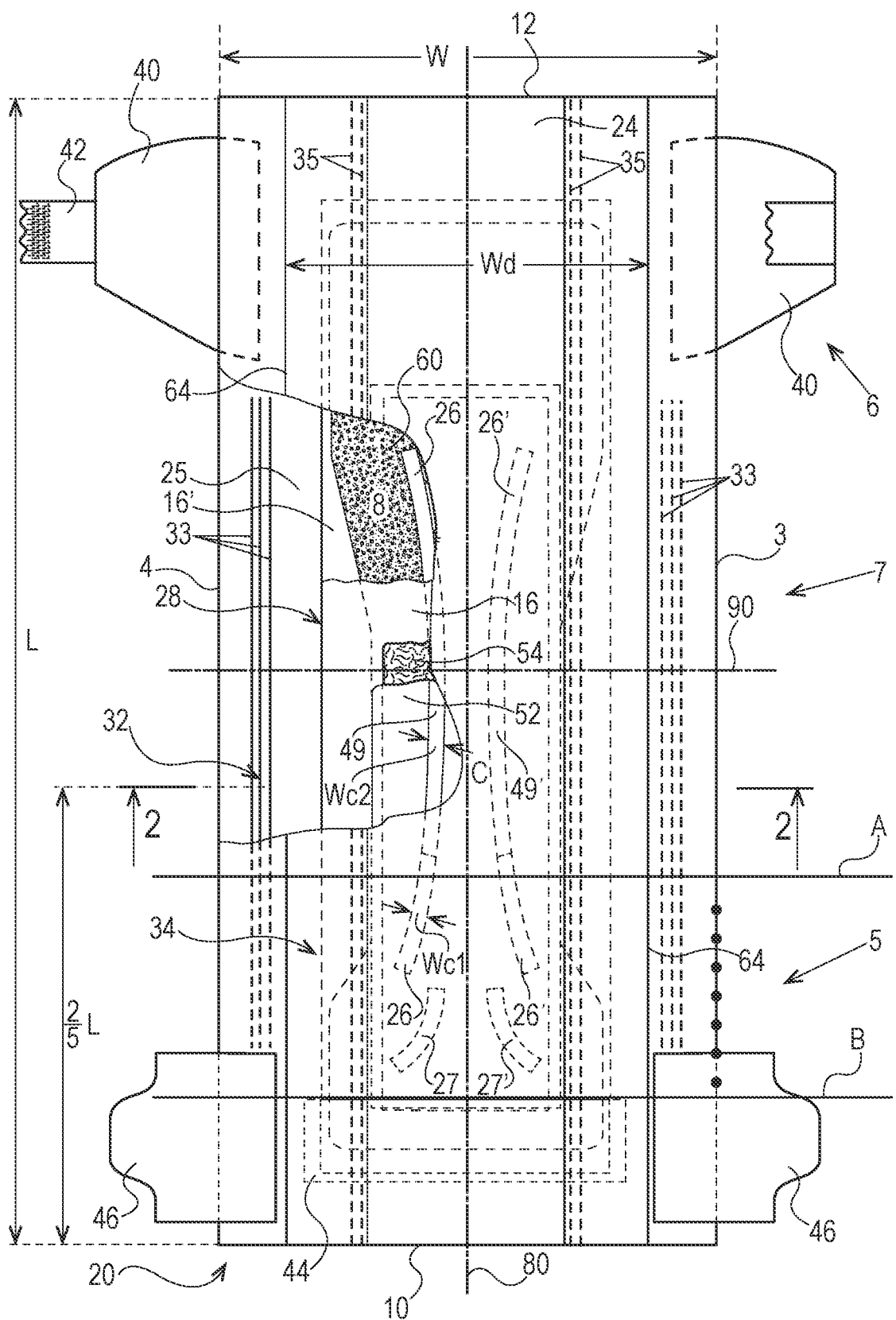
FIG. 1 is a top view of an absorbent article with some layers partially removed in accordance with a non-limiting embodiment of the present disclosure.

Various non-limiting embodiments of the present disclosure will now be described to provide an overall understanding of the principles of the structure, function, manufacture, and use of the absorbent articles with channels and methods for making the same disclosed herein. One or more examples of these non-limiting embodiments are illustrated in the accompanying drawings. Those of ordinary skill in the art will understand that the absorbent articles with channels and methods for making the same described herein and illustrated in the accompanying drawings are non-limiting example embodiments and that the scope of the various non-limiting embodiments of the present disclosure are defined solely by the claims. The features illustrated or described in connection with one non-limiting embodiment may be combined with the features of other non-limiting embodiments. Such modifications and variations are intended to be included within the scope of the present disclosure.

Introduction

The term "absorbent article, as used herein, refers to disposable devices such as infant, child, or adult diapers, pant-style diapers, training pants, sanitary napkins, diaper inserts, and the like which are placed against or in proximity to the body of the wearer to absorb and contain the various exudates discharged from the body. Typically, these articles comprise a topsheet, backsheet, an absorbent core, an acquisition system (which may be referred to as a liquid management system and may be comprised of one or several layers) and typically other components, with the absorbent core normally placed at least partially between the backsheet and the acquisition system or between the topsheet and the backsheet. The absorbent articles of the present disclosure will be further illustrated in the below description and in the Figures in the form of a taped diaper. Nothing in this description should be, however, considered limiting the scope of the claims. As such the present disclosure applies to any suitable form of absorbent articles (e.g., training pants, adult incontinence products, sanitary napkins).

The term "nonwoven web", as used herein, means a manufactured sheet, web, or batt of directionally or randomly orientated fibers, bonded by friction, and/or cohesion, and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers may have diameters ranging from less than about 0.001 mm to more than about 0.2 mm and may come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding, and airlaying. The basis weight of nonwoven webs is usually expressed in grams per square meter ($g/m^2$ or gsm).

The term "joined" or "bonded" or "attached", as used herein, encompasses configurations whereby an element is directly secured to another element by affixing the element directly to the other element, and configurations whereby an element is indirectly secured to another element by affixing the element to intermediate member(s) which in turn are affixed to the other element.

The term "channel", as used herein, is a region or zone in a material layer that has a substantially lower basis weight (e.g., less than 50%, less than 70%, less than 90%) than the surrounding material in the material layer. The channel may be a region in a material layer that is substantially material-free (e.g., 90% material-free, 95% material-free, or 99% material-free, or completely material-free). A channel may extend through one or more material layers. The channels generally have a lower bending modulus than the surrounding regions of the material layer, enabling the material layer to bend more easily and/or contain more bodily exudates within the channels than in the surrounding areas of the material layer. Thus, a channel is not merely an indentation in the material layer that does not create a reduced basis weight in the material layer in the area of the channel.

General Description of the Absorbent Article

Figure 2:
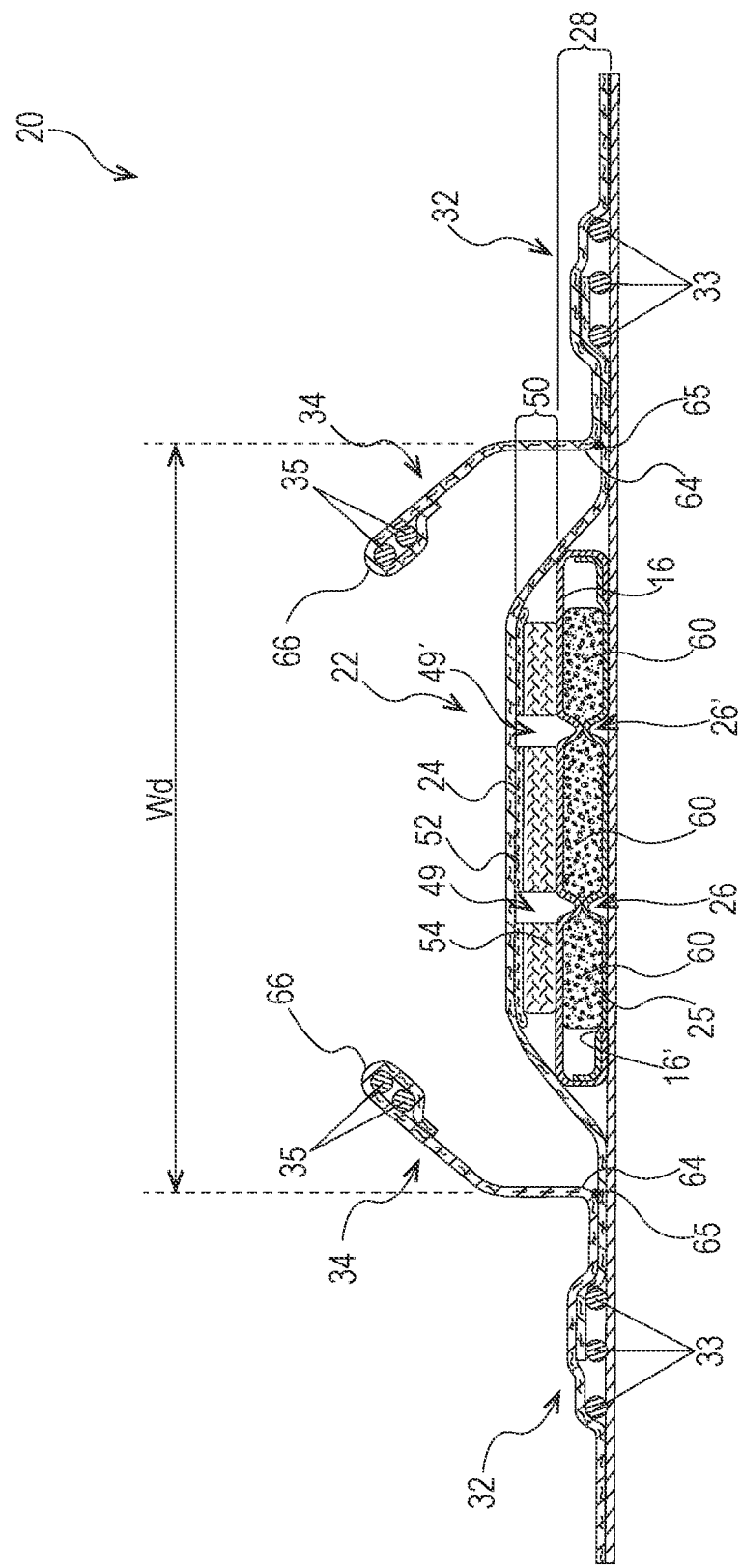
FIG. 2 is a cross-sectional view of the absorbent article taken about line 2-2 of FIG. 1 in accordance with a non-limiting embodiment of the present disclosure.
Figure 3:
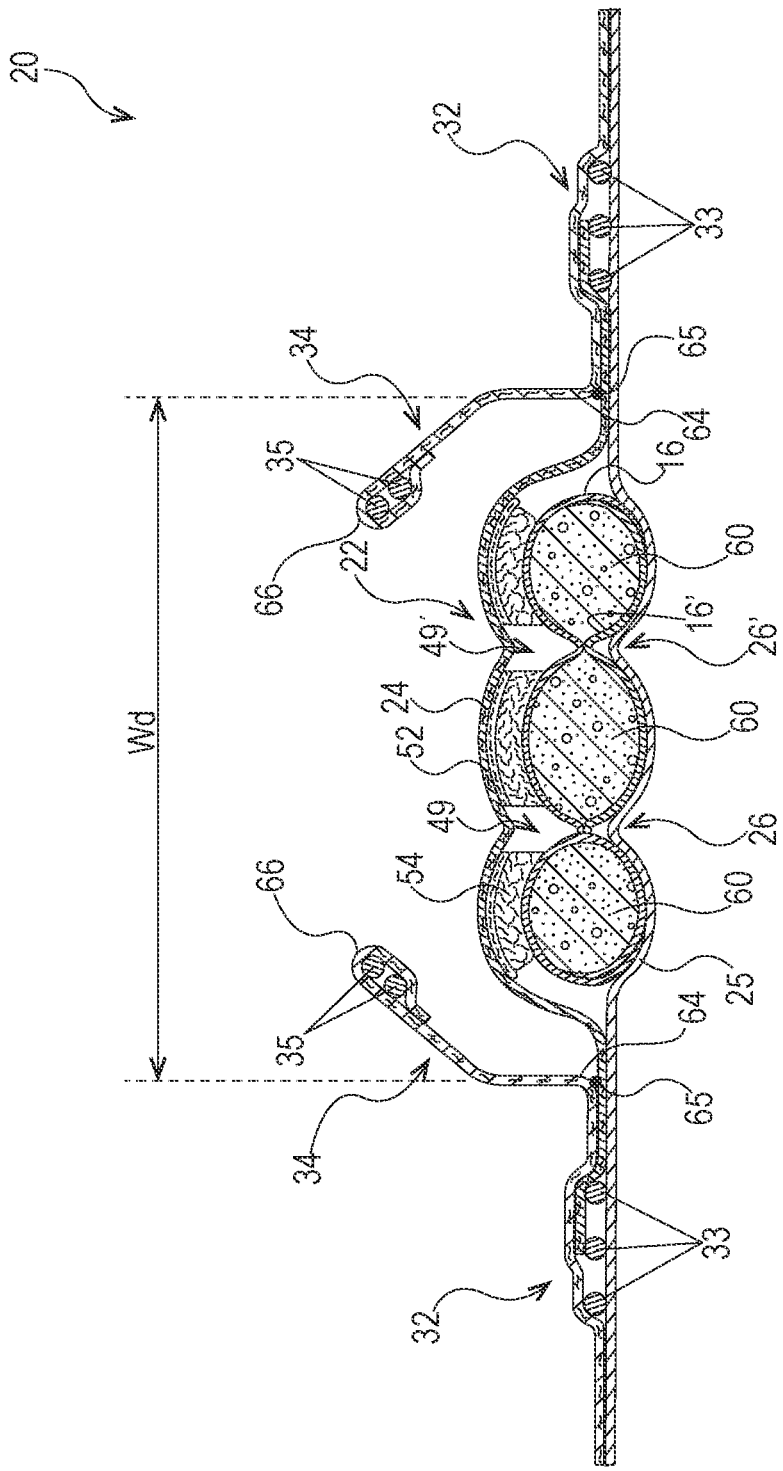
FIG. 3 is a view of the absorbent article of FIG. 2 where the absorbent article has been loaded with fluid in accordance with a non-limiting embodiment of the present disclosure.

An example absorbent article 20 according to the present disclosure, shown in the form of an infant diaper, is represented in FIGS. 1-3. FIG. 1 is a plan view of the example diaper, in a flat-out state, with portions of the structure being cut-away to more clearly show the construction of the diaper. This diaper is shown for illustration purpose only as the present disclosure may be used for making a wide variety of diapers or other absorbent articles.

The absorbent article may comprise a liquid permeable topsheet 24, a liquid impermeable backsheet 25, an absorbent core 28 positioned at least partially intermediate to topsheet 24 and the backsheet 25, and barrier leg cuffs 34. The absorbent article may also comprise a liquid management system ("LMS") 50 (shown in FIG. 2), which in the example represented comprises a distribution layer 54 and an acquisition layer 52, which will be further detailed below. In various embodiments, the acquisition layer 52 may instead distribute bodily exudates and the distribution layer 54 may instead acquire bodily exudates or both layers may distribute and/or acquire bodily exudates. The LMS 50 may also be provided as a single layer or two or more layers. The absorbent article may also comprise elasticized gasketing cuffs 32 joined to the chassis of the absorbent article, typically via the topsheet and/or backsheet, and substantially planar with the chassis of the diaper.

The Figures also show typical taped diaper components such as a fastening system comprising adhesive tabs 42 or other mechanical fasteners attached towards the rear edge of the absorbent article 20 and cooperating with a landing zone 44 on the front of the absorbent article 20. The absorbent article may also comprise other typical elements, which are not represented, such as a rear elastic waist feature, a front elastic waist feature, transverse barrier cuff(s), and/or a lotion application, for example.

The absorbent article 20 may comprise a front waist edge 10, a rear waist edge 12 longitudinally opposing the front waist edge 10, a first side edge 3, and a second side edge 4 laterally opposing the first side edge 3. The front waist edge 10 is the edge of the absorbent article 20 which is intended to be placed towards the front of the user when worn, and the rear waist edge 12 is the opposite edge. The absorbent article may have a longitudinal axis 80 extending from the lateral midpoint of the front waist edge 10 to a lateral midpoint of the rear waist edge 12 of the absorbent article 20 and dividing the absorbent article 20 in two substantially symmetrical halves relative to the longitudinal axis 80, with article placed flat and viewed from above as in FIG. 1. The absorbent article may also have a lateral axis 90 extending from the longitudinal midpoint of the first side edge 3 to the longitudinal midpoint of the second side edge 4. The length L of the absorbent article 20 may be measured along the longitudinal axis 80 from the front waist edge 10 to the rear waist edge 12. The crotch width of the absorbent article 20 may be measured along the lateral axis 90 from the first side edge 3 to the second side edge 4. The absorbent article 20 may comprise a crotch point C defined herein as the point placed on the longitudinal axis at a distance of two fifth (⅖) of L starting from the front edge 10 of the absorbent article 20. The absorbent article 20 may comprise a front waist region 5, a rear waist region 6, and a crotch region 7. The front waist region, the rear waist region, and the crotch region each define ⅓ of the longitudinal length of the absorbent article.

The topsheet 24, the backsheet 25, the absorbent core 28, and the other article components may be assembled in a variety of configurations, in particular by gluing or heat embossing, for example. Example diaper configurations are described generally in U.S. Pat. Nos. 3,860,003, 5,221,274, 5,554,145, 5,569,234, 5,580,411, and 6,004,306. The absorbent article may be thin. The caliper at the crotch point C or in the crotch region 7 of the absorbent article 20 may be, for example, from 4.0 mm to 12.0 mm or alternatively from 6.0 mm to 10.0 mm.

The absorbent core 28 may comprise an absorbent material comprising 75% to 100%, at least 80%, at least 85%, at least 90%, at least 95%, or at least 99% all by weight of the absorbent material, specifically reciting all 0.1% increments within the above-specified ranges and all ranges formed therein or thereby, and a core wrap enclosing the absorbent material. The core wrap may typically comprise two materials, substrates, or nonwoven materials 16 and 16' for the top side and bottom side of the core.

The core may comprises one or more channels, represented in FIG. 1 as the four channels 26, 26' and 27, 27'. Additionally or alternative, the LMS 50 may comprises one or more channels, represented in FIGS. 1-3 as channels 49, 49'. In some embodiments, the channels of the LMS 50 may be positioned within the absorbent article 20 such they aligned with, substantially aligned with, overlap, or at least partially overlap, the channels of the absorbent core 28. These and other components of the absorbent articles will now be discussed in more details.

Topsheet

The topsheet 24 is the part of the absorbent article that is directly in contact with the wearer's skin. The topsheet 24 may be joined to the backsheet 25, the core 28 and/or any other layers as is known to those of skill in the art. Usually, the topsheet 24 and the backsheet 25 are joined directly to each other in some locations (e.g., on or close to the periphery of the article) and are indirectly joined together in other locations by directly joining them to one or more other elements of the absorbent article 20.

The topsheet 24 may be compliant, soft-feeling, and non-irritating to the wearer's skin. Further, at least a portion of the topsheet 24 may be liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet 24 includes fibers, the fibers may be spunbond, carded, wet-laid, melt-blown, hydroentangled, or otherwise processed as is known in the art, in particular spunbond PP nonwoven. Example topsheets comprising a web of staple-length polypropylene fibers are manufactured by Veratec, Inc., a Division of International Paper Company, of Walpole, MA under the designations P-8, P-9, P-10, or P-11. Other example topsheet are manufactured by Polymer Group Inc. under material trade names W5030NG, W5030TP, and W5030TO.

Any portion of the topsheet 24 may be coated with a skin care composition, antibacterial agent, or other beneficial agents as is generally known in the art. Further, the topsheet 24, the backsheet 25 or any portion of the topsheet or backsheet may be embossed and/or matte finished to provide a more cloth like appearance.

The topsheet 24 may comprise one or more apertures to ease penetration of exudates therethrough, such as urine and/or feces (solid, semi-solid, or liquid). Typical absorbent article topsheets have a basis weight of from about 5 gsm to about 30 gsm, from about 10 to about 21 gsm or from about 12 to about 18 gsm, but other basis weights are within the scope of the present disclosure.

Backsheet

The backsheet 25 is generally that portion of the absorbent article 20 positioned adjacent the garment-facing surface of the absorbent core 28 and which prevents, or at least inhibits, the exudates absorbed and contained therein from soiling articles such as bedsheets and undergarments. The backsheet 25 is typically impermeable, or at least substantially impermeable, to liquids (e.g., urine). The backsheet may, for example, be or comprise a thin plastic film such as a thermoplastic film having a thickness of about 0.012 mm to about 0.051 mm. Example backsheet films include those manufactured by Tredegar Corporation, based in Richmond, VA, and sold under the trade name CPC2 film. Other suitable backsheet materials may include breathable materials which permit vapors to escape from the absorbent article 20 while still preventing, or at least inhibiting, exudates from passing through the backsheet 25. Example breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, VA, and sold under the designation EXAIRE, and monolithic films such as manufactured by Clopay Corporation, Cincinnati, OH under the name HYTREL blend P18-3097.

The backsheet 25 may be joined to the topsheet 24, the absorbent core 28, and/or any other element of the absorbent article 20 by any attachment methods known to those of skill in the art. Suitable attachment methods are described above with respect to methods for joining the topsheet 24 to other elements of the absorbent article 20. For example, the attachment methods may include using a uniform continuous layer of adhesive, a patterned layer of adhesive, or an array of separate lines, spirals, or spots of adhesive. Suitable attachment methods comprising an open pattern network of filaments of adhesive is disclosed in U.S. Pat. No. 4,573,986. Other suitable attachment methods include using several lines of adhesive filaments which are swirled into a spiral pattern, as is illustrated by the apparatus and methods shown in U.S. Pat. Nos. 3,911,173, 4,785,996, and 4,842,666. Adhesives which have been found to be satisfactory are manufactured by H. B. Fuller Company of St. Paul, Minnesota and marketed as HL-1620 and HL 1358-XZP. Alternatively, the attachment methods may comprise using heat bonds, pressure bonds, ultrasonic bonds, dynamic mechanical bonds, or any other suitable attachment methods or combinations of these attachment methods as are known to those of skill in the art.

Absorbent Core

As used herein, the term "absorbent core" refers to the individual component of the absorbent article having the most absorbent capacity and may comprise an absorbent material. In some embodiments, the absorbent core comprises a core wrap enclosing the absorbent material. The term "absorbent core" does not include the liquid management system or any other component of the absorbent article which is not either integral part of the core wrap or placed within the core wrap. The absorbent core may comprise, consist essentially of, or consist of, a core wrap, absorbent material as defined below, and glue enclosed within the core wrap. The absorbent core periphery, which may be the periphery of the core wrap, may define any suitable shape, such as a "T," "Y," "hour-glass," or "dog-bone" shape, for example. An absorbent core periphery having a generally "dog bone" or "hour-glass" shape may taper along its width towards the middle or "crotch" region of the core. In this way, the absorbent core may have a relatively narrow width in an area of the absorbent core intended to be placed in the crotch region of an absorbent article.

The absorbent core 28 of the present disclosure may comprise an absorbent material with a high amount of superabsorbent polymers (herein abbreviated as "SAP") enclosed within a core wrap. The SAP content may represent 70% to 100% or at least 70%, 75%, 80%, 85%, 90%, 95%, 99%, or 100% by weight of the absorbent material contained in the core wrap. The core wrap is not considered as absorbent material for the purpose of assessing the percentage of SAP in the absorbent core.

"Absorbent material" means a material which has some absorbency property or liquid retaining properties, such as SAP, cellulosic fibers as well as synthetic fibers. Typically, glues used in making absorbent cores have no absorbency properties and are not considered as absorbent material. The SAP content may be higher than 80%, for example at least 85%, at least 90%, at least 95%, at least 99%, and even up to and including 100% of the weight of the absorbent material contained within the core wrap, as stated above. This provides a relatively thin core compared to conventional cores typically comprising between 40-60% SAP, for example, and high content of cellulose fibers. The absorbent material may comprise less than 15% or less than 10% weight percent of natural or synthetic fibers, less than 5% weight percent, less than 3% weight percent, less than 2% weight percent, less than 1% weight percent, or may even be substantially free of, or free of, natural and/or synthetic fibers, specifically reciting all 0.1% increments within the specified ranges and all ranges formed therein or thereby. The absorbent material may advantageously comprise little or no airfelt (cellulose) fibers, in particular the absorbent core may comprise less than 15%, 10%, 5%, 3%, 2%, 1% airfelt (cellulose) fibers by weight, or may even be substantially free of, or free of, cellulose fibers, specifically reciting all 0.1% increments within the specified ranges and all ranges formed therein or thereby.

Figure 4:
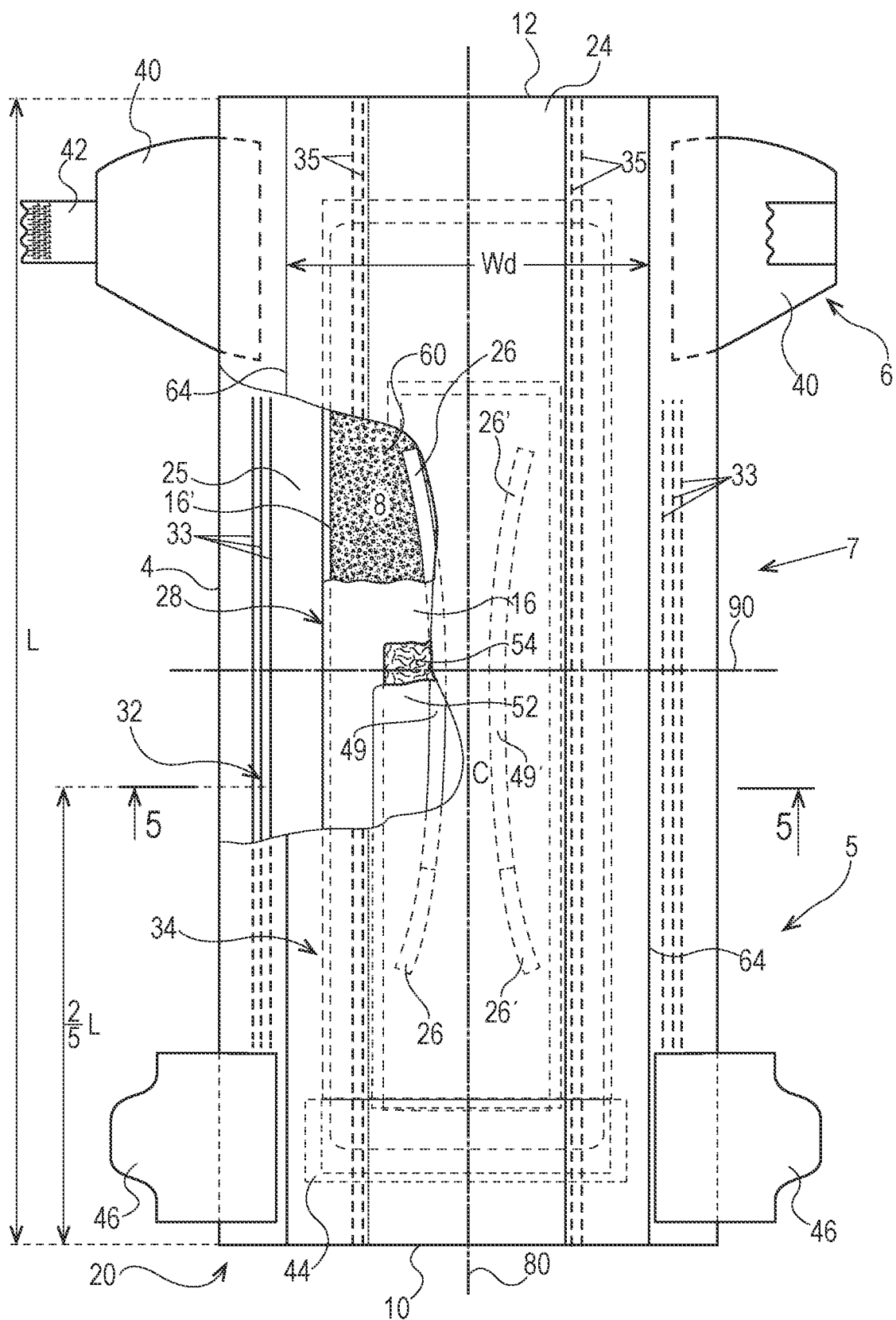
FIG. 4 is a top view of another absorbent article with some layers partially removed in accordance with a non-limiting embodiment of the present disclosure.
Figure 5:
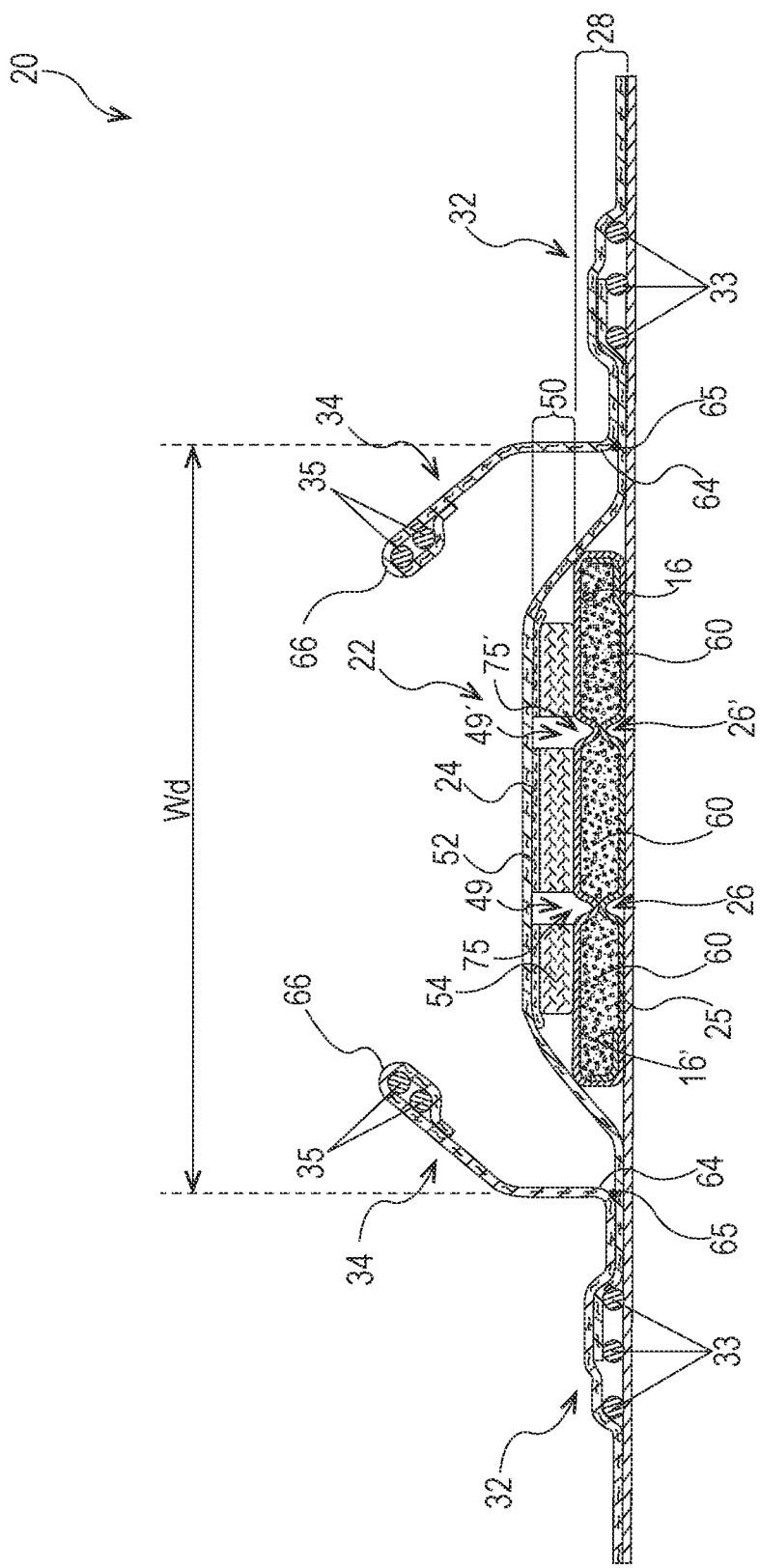
FIG. 5 is a cross-sectional view of the absorbent article taken about line 5-5 of FIG. 4 in accordance with a non-limiting embodiment of the present disclosure.
Figure 6:
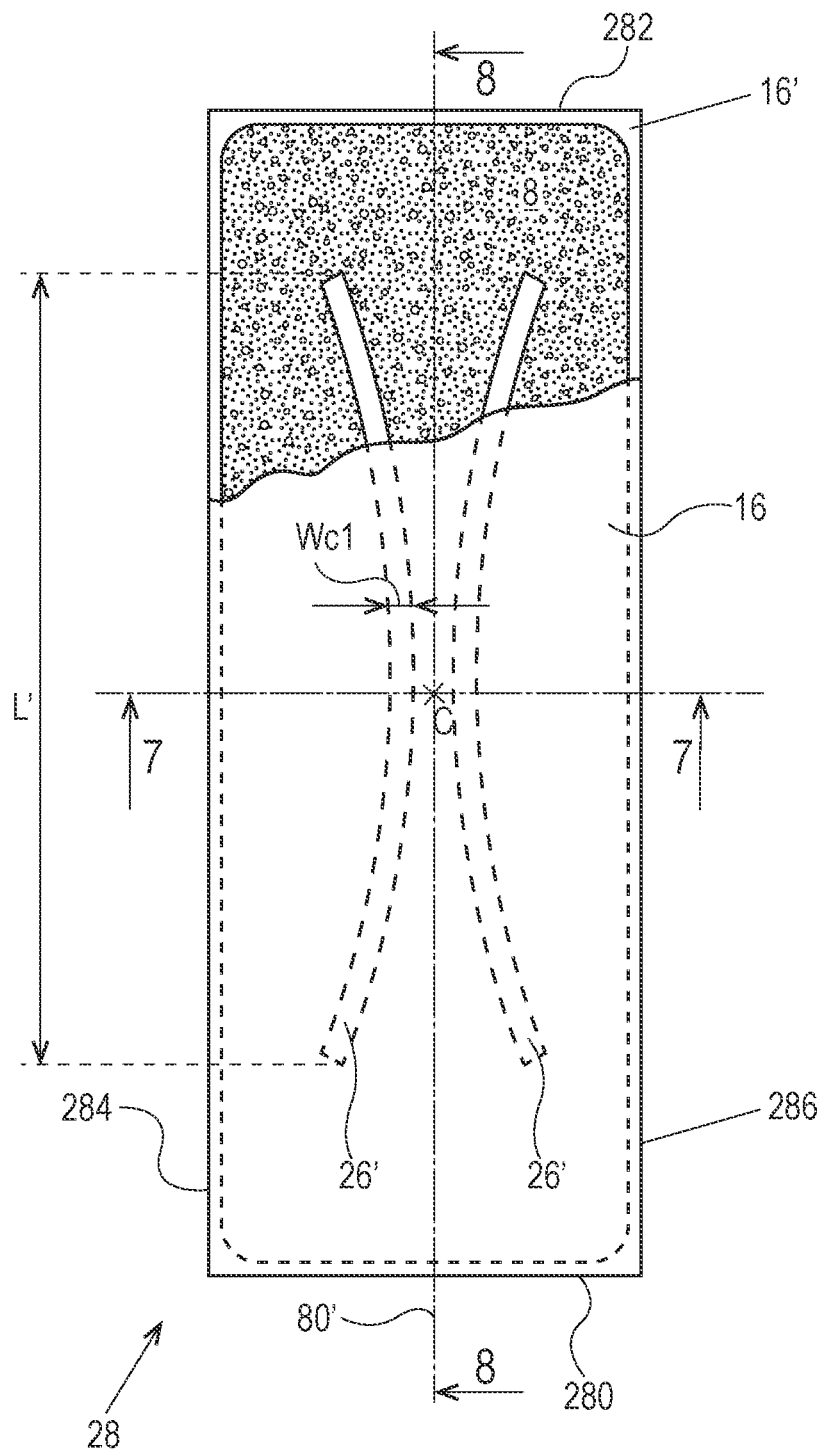
FIG. 6 is a top view of an absorbent core of the absorbent article of FIG. 4 with some layers partially removed in accordance with a non-limiting embodiment of the present disclosure.
Figure 7:
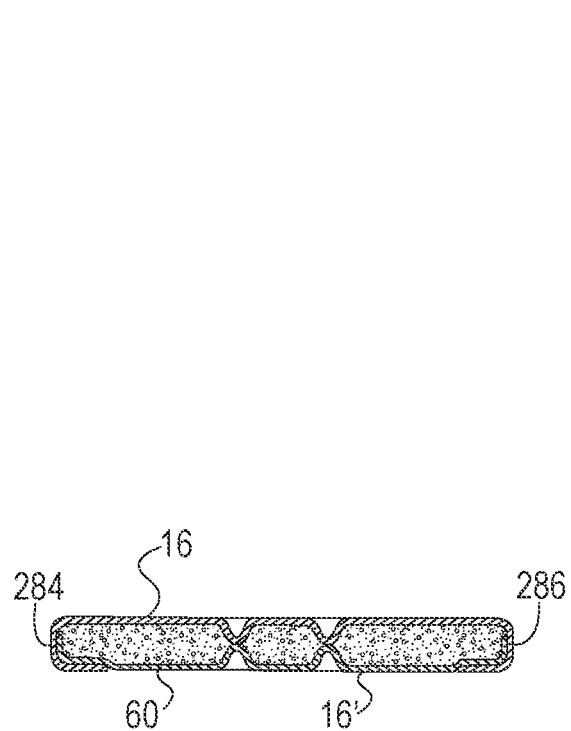
FIG. 7 is a cross-sectional view of the absorbent core taken about line 7-7 of FIG. 6 in accordance with a non-limiting embodiment of the present disclosure.
Figure 8:
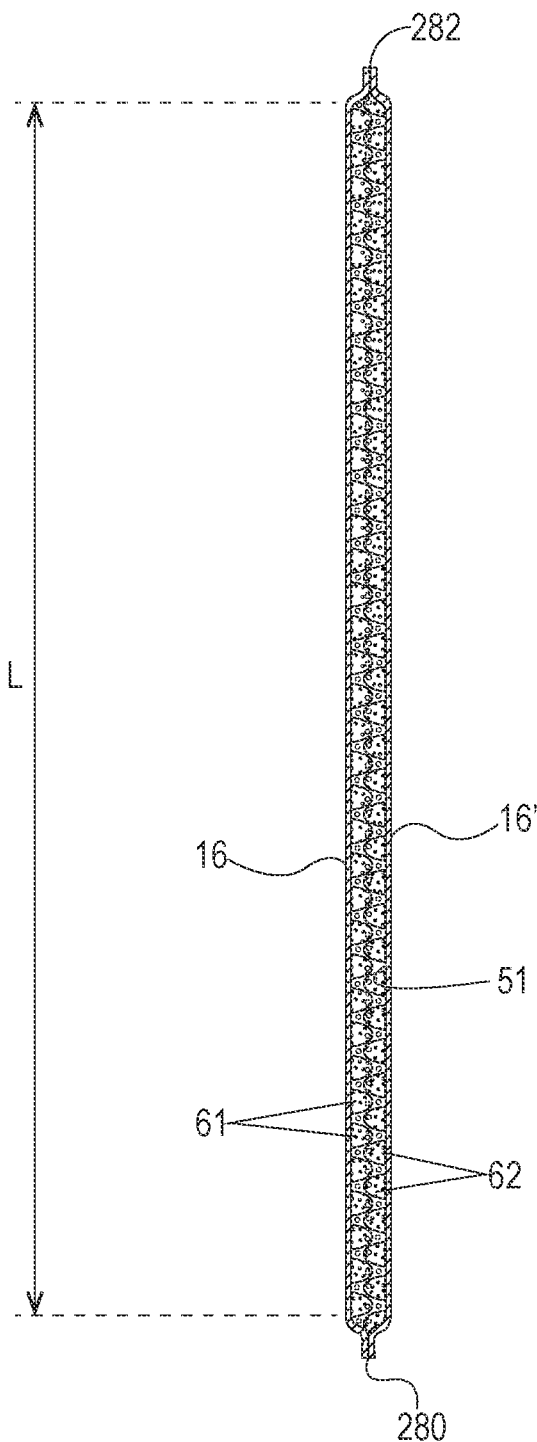
FIG. 8 is a cross-sectional view of the absorbent core taken about line 8-8 of FIG. 6 in accordance with a non-limiting embodiment of the present disclosure.

The example absorbent core 28 of the absorbent article of FIGS. 4 and 5 is shown in isolation in FIGS. 6-8. The absorbent core 28 may comprises a front side 280, a rear side 282, and two longitudinal sides 284, 286 joining the front side 280 and the rear side 282. The absorbent core may also comprise a generally planar top side and a generally planar bottom side. The front side 280 of the core 28 is the side of the core 28 intended to be placed towards the front waist edge 10 of the absorbent article. The core 28 may have a longitudinal axis 80' corresponding substantially to the longitudinal axis 80 of the absorbent article, as seen from the top in a planar view as in FIG. 1. In an embodiment, the absorbent material may be distributed in higher amount towards the front side than towards the rear side as more absorbency may be required at the front in particular articles. In another embodiment, the absorbent material may have a non-uniform basis weight or a uniform basis weight across any portion of the core. In an embodiment, the front and rear sides of the core may be shorter than the longitudinal sides of the core. The core wrap may be formed by two nonwoven materials, substrates, laminates, or other materials, 16, 16' which may be at least partially sealed along the sides of the absorbent core. The core wrap may be at least partially sealed along its front side 280, rear side 282, and two longitudinal sides 284, 286 so that substantially no absorbent material leaks out of the absorbent core wrap. The first material, substrate, or nonwoven 16 may at least partially surround the second material, substrate, or nonwoven 16' to form the core wrap, as illustrated in FIG. 7. The first material 16 may surround a portion of the second material 16' proximate to the first and second side edges 284 and 286.

The absorbent core of the present disclosure may comprise adhesive, for example, to help immobilizing the SAP within the core wrap and/or to ensure integrity of the core wrap, in particular when the core wrap is made of two or more substrates. The core wrap may extend to a larger area than strictly needed for containing the absorbent material within.

Cores comprising relatively high amount of SAP with various core designs are disclosed in U.S. Pat. No. 5,599,335 (Goldman), EP 1,447,066 (Busam), WO 95/11652 (Tanzer), U.S. Pat. Publ. No. 2008/0312622A1 (Hundorf), and WO 2012/052172 (Van Malderen).

The absorbent material may be one or more continuous layers present within the core wrap. In other embodiments, the absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two or more absorbent layers having discontinuous absorbent material application pattern, wherein the resulting layer is substantially continuously distributed across the absorbent particulate polymer material area, as disclosed in U.S. Pat. Appl. Publ. No. 2008/0312622A1 (Hundorf), for example. The absorbent core 28 may comprise a first absorbent layer and a second absorbent layer. The first absorbent layer may comprise the first material 16 and a first layer 61 of absorbent material, which may be 100% or less of SAP. The second absorbent layer may comprise the second material 16' and a second layer 62 of absorbent material, which may also be 100% or less of SAP. The absorbent core 28 may also comprise a fibrous thermoplastic adhesive material 51 at least partially bonding each layer of absorbent material 61, 62 to its respective material 16 or 16'. This is illustrated in FIGS. 7-8, as an example, where the first and second SAP layers have been applied as transversal stripes or "land areas" having the same width as the desired absorbent material deposition area on their respective substrate before being combined. The stripes may comprise different amount of absorbent material (SAP) to provide a profiled basis weight along the longitudinal axis of the core 80. The first material 16 and the second material 16' may form the core wrap.

The fibrous thermoplastic adhesive material 51 may be at least partially in contact with the absorbent material 61, 62 in the land areas and at least partially in contact with the materials 16 and 16' in the junction areas. This imparts an essentially three-dimensional structure to the fibrous layer of thermoplastic adhesive material 51, which in itself is essentially a two-dimensional structure of relatively small thickness, as compared to the dimension in length and width directions. Thereby, the fibrous thermoplastic adhesive material may provide cavities to cover the absorbent material in the land area, and thereby immobilizes this absorbent material, which may be 100% or less of SAP.

The thermoplastic adhesive material 51 may comprise, in its entirety, a single thermoplastic polymer or a blend of thermoplastic polymers, having a softening point, as determined by the ASTM Method D-36-95 "Ring and Ball", in the range between 50° C. and 300° C., and/or the thermoplastic adhesive material may be a hotmelt adhesive comprising at least one thermoplastic polymer in combination with other thermoplastic diluents such as tackifying resins, plasticizers and additives such as antioxidants.

The thermoplastic adhesive used for the fibrous layer may have elastomeric properties, such that the web formed by the fibers on the SAP layer is able to be stretched as the SAP swell. Elastomeric, hot-melt adhesives of these types are described in more detail in U.S. Pat. No. 4,731,066 issued to Korpman on Mar. 15, 1988. The thermoplastic adhesive material may be applied as fibers.

Superabsorbent Polymer (SAP)

"Superabsorbent polymers" ("SAP"), as used herein, refer to absorbent materials which are cross-linked polymeric materials that can absorb at least 10 times their weight of an aqueous 0.9% saline solution as measured using the Centrifuge Retention Capacity (CRC) test (EDANA method WSP 241.2-05E). The SAP used may have a CRC value of more than 20 g/g, more than 24 g/g, from 20 to 50 g/g, from 20 to 40 g/g, or from 24 to 30 g/g, specifically reciting all 0.1 g/g increments within the above-specified ranges and any ranges created therein or thereby. The SAP useful with the present disclosure may include a variety of water-insoluble, but water-swellable polymers capable of absorbing large quantities of fluids.

The superabsorbent polymer may be in particulate form so as to be flowable in the dry state. Particulate absorbent polymer materials may be made of poly(meth)acrylic acid polymers. However, starch-based particulate absorbent polymer material may also be used, as well polyacrylamide copolymer, ethylene maleic anhydride copolymer, crosslinked carboxymethylcellulose, polyvinyl alcohol copolymers, cross-linked polyethylene oxide, and starch grafted copolymer of polyacrylonitrile. The superabsorbent polymer may be polyacrylates and polyacrylic acid polymers that are internally and/or surface cross-linked. Suitable materials are described in the PCT Patent Application Nos. WO 07/047598, WO 07/046052, WO2009/155265, and WO2009/155264, for example. In some embodiments, suitable superabsorbent polymer particles may be obtained by generally known production processes as described in WO 2006/083584, for example.

The SAP useful for the present disclosure may be of numerous shapes. The term "particles" refers to granules, fibers, flakes, spheres, powders, platelets and other shapes and forms known to persons skilled in the art of superabsorbent polymer particles. In some embodiments, the SAP particles may be in the shape of fibers, i.e., elongated, acicular superabsorbent polymer particles. In those embodiments, the superabsorbent polymer particles fibers may have a minor dimension (i.e., diameter of the fiber) of less than about 1 mm, usually less than about 500 µm, or less than 250 µm down to 50 µm, specifically reciting all 1 µm increments within the above-specified ranges and any ranges formed therein or thereby. The length of the fibers may be about 3 mm to about 100 mm, specifically reciting all 1 mm increments within the above-specified range and any ranges formed therein or thereby. The fibers may also be in the form of a long filament that may be woven.

SAP may be spherical-like particles. In contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle. The superabsorbent polymer particles may have a particle size of less than 850 µm, from 50 to 850 µm, from 100 to 710 µm, or from 150 to 650 µm, specifically reciting all 1 µm increments within the above-specified ranges and any ranges formed therein or thereby, as measured according to EDANA method WSP 220.2-05. SAP having a relatively low particle size may help to increase the surface area of the absorbent material which is in contact with liquid exudates and therefore supports fast absorption of liquid exudates.

The SAP may have a particle size in the range from 45 µm to 4000 µm, more specifically a particle size distribution within the range of from 45 µm to about 2000 µm, or from about 100 µm to about 1000, 850 or 600 µm, specifically reciting all 1 µm increments within the above-specified ranges and any ranges formed therein or thereby. The particle size distribution of a material in particulate form can be determined, for example, by means of dry sieve analysis (EDANA 420.02 "Particle Size distribution). The surface of the SAP may be coated, for example, with a cationic polymer. Certain cationic polymers may include polyamine or polyimine materials. The absorbent core may comprise one or more types of SAP.

For most absorbent articles, liquid discharges from a wearer occur predominately in the front half of the absorbent article, in particular for a diaper. The front half of the absorbent article (as defined by the region between the front edge and the lateral axis 90) may therefore comprise most of the absorbent capacity of the core). Thus, at least 60% of the SAP, or at least 65%, 70%, 75%, 80%, or 85% of the SAP may be present in the front half of the absorbent article, the remaining SAP being disposed in the rear half of the absorbent article. In other embodiments, the SAP distribution may be uniform through the core or may have other suitable distributions.

The total amount of SAP present in the absorbent core may also vary according to expected user. Diapers for newborns may require less SAP than infant, child, or adult incontinence diapers. The amount of SAP in the core may be about 5 to 60 g or from 5 to 50 g, specifically reciting all 0.1 increments within the specified ranges and any ranged formed therein or thereby. The average SAP basis weight within the (or "at least one", if several are present) deposition area 8 of the SAP may be at least 50, 100, 200, 300, 400, 500 or more g/m². The areas of the channels (e.g., 27, 27') present in the absorbent material deposition area 8 are deduced from the absorbent material deposition area to calculate this average basis weight.

Core Wrap

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, as illustrated, for example, in FIGS. 2 and 7, the longitudinal and/or transversal edges of one of the substrates are folded over the other substrate to form flaps. These flaps are then bonded to the external surface of the other substrate, typically by gluing. Other techniques may be used to form a core wrap. For example, the longitudinal and/or transversal edges of the substrates may be bonded together and then folded underneath the absorbent core 28 and bonded in that position.

The core wrap may be formed by any materials suitable for receiving and containing the absorbent material. Typical substrate materials used in the production of conventional cores may be used, in particular paper, tissues, films, wovens or nonwovens, or laminates or composites of any of these. The core wrap may be formed by a nonwoven web, such as a carded nonwoven, spunbond nonwoven ("S") or meltblown nonwoven ("M"), and laminates of any of these. For example, spunmelt polypropylene nonwovens may be suitable, in particular those having a laminate web SMS, or SMMS, or SSMMS, structure, and having a basis weight range of about 5 gsm to about 15 gsm. Suitable materials are disclosed in U.S. Pat. No. 7,744,576, U.S. Pat. Publ. No. 2011/0268932A1, U.S. Pat. Publ. No. 2011/0319848A1, and U.S. Pat. Publ. No. 2011/0250413A1. Nonwoven materials provided from synthetic fibers may also be used, such as PE, PET, and/or PP, for example.

If the core wrap comprises a first substrate, nonwoven or material 16 and a second substrate, nonwoven, or materials 16' these may be made of the same type of material, may be made of different materials, or one of the substrates may be treated differently than the other to provide it with different properties. As the polymers used for nonwoven production are inherently hydrophobic, they may be coated with hydrophilic coatings if placed on the fluid receiving side of the absorbent core. It may be advantageous that the top side of the core wrap, i.e., the side placed closer to the wearer in the absorbent article, be more hydrophilic than the bottom side of the core wrap. A possible way to produce nonwovens with durably hydrophilic coatings is via applying a hydrophilic monomer and a radical polymerization initiator onto the nonwoven, and conducting a polymerization activated via UV light resulting in monomer chemically bound to the surface of the nonwoven. An alternative possible way to produce nonwovens with durably hydrophilic coatings is to coat the nonwoven with hydrophilic nanoparticles, e.g., as described in WO 02/064877.

Permanently hydrophilic nonwovens are also useful in some embodiments. Surface tension, as described in U.S. Pat. No. 7,744,576 (Busam et al.), can be used to measure how permanently a certain hydrophilicity level is achieved. Liquid strike through, as described in U.S. Pat. No. 7,744, 576, may be used to measure the hydrophilicity level. The first and/or second substrate may have a surface tension of at least 55, at least 60, or at least 65 mN/m or higher when wetted with saline solution. The substrate may also have a liquid strike through time of less than 5 seconds for a fifth gush of liquid. These values can be measured using the test methods described in U.S. Pat. No. 7,744,576B2: "Determination Of Surface Tension" and "Determination of Strike Through" respectively.

Hydrophilicity and wettability are typically defined in terms of contact angle and the strike through time of the fluids, for example, through a nonwoven fabric. This is discussed in detail in the American Chemical Society publication entitled "Contact angle, wettability and adhesion", edited by Robert F. Gould (Copyright 1964). A substrate having a lower contact angle between the water and the surface of substrate may be said to be more hydrophilic than another.

The substrates may also be air-permeable. Films useful herein may therefore comprise micro-pores. The substrate may have an air-permeability of from 40 or from 50, to 300 or to 200 m³/(m²×min), as determined by EDANA method 140-1-99 (125 Pa, 38.3 cm²). The material of the core wrap may alternatively have a lower air-permeability, e.g., being non-air-permeable, for example, to facilitate handling on a moving surface comprising vacuum.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal does not need to be continuous along the whole periphery of the core wrap but may be discontinuous along part or the whole of it, such as formed by a series of seal points spaced on a line. A seal may be formed by gluing and/or thermal bonding.

If the core wrap is formed by two substrates 16, 16', four seals may be used to enclose the absorbent material 60 within the core wrap. For example, a first substrate 16 may be placed on one side of the core (the top side as represented in the Figures) and extend around the core's longitudinal edges to at least partially wrap the opposed bottom side of the core. The second substrate 16' may be present between the wrapped flaps of the first substrate 16 and the absorbent material 60. The flaps of the first substrate 16 may be glued to the second substrate 16' to provide a strong seal. This so called C-wrap construction may provide benefits such as improved resistance to bursting in a wet loaded state compared to a sandwich seal. The front side and rear side of the core wrap may then also be sealed by gluing the first substrate and second substrate to another to provide complete encapsulation of the absorbent material across the whole of the periphery of the core. For the front side and rear side of the core, the first and second substrates may extend and may be joined together in a substantially planar direction, forming for these edges a so-called sandwich construction. In the so-called sandwich construction, the first and second substrates may also extend outwardly on all sides of the core and be sealed flat, or substantially flat, along the whole or parts of the periphery of the core typically by gluing and/or heat/pressure bonding. In an embodiment, neither the first nor the second substrates need to be shaped, so that they can be rectangularly cut for ease of production but other shapes are within the scope of the present disclosure.

The core wrap may also be formed by a single substrate which may enclose as in a parcel wrap the absorbent material and be sealed along the front side and rear side of the core and one longitudinal seal.

SAP Deposition Area

The absorbent material deposition area 8 may be defined by the periphery of the layer formed by the absorbent material 60 within the core wrap, as seen from the top side of the absorbent core. The absorbent material deposition area 8 may have various shapes, in particular, a so-called "dog bone" or "hour-glass" shape, which shows a tapering along its width towards the middle or "crotch" region of the core. In this way, the absorbent material deposition area 8 may have a relatively narrow width in an area of the core intended to be placed in the crotch region of the absorbent article, as illustrated in FIG. 1. This may provide better wearing comfort. The absorbent material deposition area 8 may thus have a width (as measured in the transversal direction) at its narrowest point, which is less than about 100 mm, 90 mm, 80 mm, 70 mm, 60 mm, or even less than about 50 mm. This narrowest width may further be at least 5 mm, or at least 10 mm, smaller than the width of the deposition area 8 at its largest point in the front and/or rear regions deposition area 8. The absorbent material deposition area 8 may also be generally rectangular, for example as shown in FIGS. 4-6, but other deposition areas, such as a "T," "Y," "hour-glass," or "dog-bone" shapes are also within the scope of the present disclosure.

The basis weight (amount deposited per unit of surface) of the SAP may also be varied along the deposition area 8 to create a profiled distribution of absorbent material, in particular SAP, in the longitudinal direction, in the transversal direction, or both directions of the core. Hence, along the longitudinal axis of the core, the basis weight of absorbent material may vary, as well as along the transversal axis, or any axis parallel to any of these axes. The basis weight of SAP in areas of relatively high basis weight may thus be at least 10%, 20%, 30%, 40%, or 50% higher than in an area of relatively low basis weight. In an embodiment, the SAP present in the absorbent material deposition area 8 at the level of the crotch point C may have more SAP per unit of surface deposited as compared to another area of the absorbent material deposition area 8.

The absorbent material may be deposited using known techniques, which may allow relatively precise deposition of SAP at relatively high speed. In particular, the SAP printing technology as disclosed in U.S. Pat. Publ. No. 2008/0312617 and U.S. Pat. Publ. No. 2010/0051166A1 (both to Hundorf et al.) may be used. This technique uses a printing roll to deposit SAP onto a substrate disposed on a grid of a support which may include a plurality of cross bars extending substantially parallel to and spaced from one another so as to form channels extending between the plurality of cross-bars. This technology allows high-speed and precise deposition of SAP on a substrate. The channels of the absorbent core may be formed for example by modifying the pattern of the grid and receiving drums so that no SAP is applied in areas corresponding to the channels. EP application number 11169396.6 discloses this modification in more details.

Channels in the Absorbent Core

The absorbent material deposition area 8 may comprise at least one channel 26, which is at least partially oriented in the longitudinal direction of the absorbent article 80 (i.e., has a longitudinal vector component). Other channels may be at least partially oriented in the lateral direction (i.e., has a lateral vector component) or in any other direction. If the following, the plural form "channels" will be used to mean "at least one channel". The channels may have a length L' projected on the longitudinal axis 80 of the absorbent article that is at least 10% of the length L of the absorbent article. The channels may also be circular, oblong, or be in the shape of a variety of other closed polygons. The channels may be formed in various ways. For example, the channels may be formed by zones within the absorbent material deposition area 8 which may be substantially free of, or free of, absorbent material, in particular, SAP. In addition or alternatively, the channel(s) may also be formed by continuously or discontinuously bonding the top side of the core wrap to the bottom side of the core wrap through the absorbent material deposition area 8. The channels may be continuous but it is also envisioned that the channels may be intermittent. The liquid management system 50, or another layer of the absorbent article, may also comprise channels, which may or not correspond to the channels of the absorbent core, as described in more detail below.

In some embodiments, the channels may be present at least at the same longitudinal level as the crotch point C or the lateral axis 90 in the absorbent article, as represented in FIG. 1 with the two longitudinally extending channels 26, 26'. The channels may also extend from the crotch region 7 or may be present in the front waist region 5 and/or in the rear waist region 6 of the absorbent article.

The absorbent core 28 may also comprise more than two channels, for example, at least 3, at least 4, at least 5, or at least 6 or more. Shorter channels may also be present, for example in the rear waist region 6 or the front waist region 5 of the core as represented by the pair of channels 27, 27' in FIG. 1 towards the front of the absorbent article. The channels may comprise one or more pairs of channels symmetrically arranged, or otherwise arranged relative to the longitudinal axis 80.

The channels may be particularly useful in the absorbent core when the absorbent material deposition area is rectangular, as the channels may improve the flexibility of the core to an extent that there is less advantage in using a non-rectangular (shaped) core. Of course channels may also be present in a layer of SAP having a shaped deposition area.

The channels may extend substantially longitudinally, which means that each channel extends more in the longitudinal direction than in the transverse direction, or at least twice as much in the longitudinal direction than in the transverse direction (as measured after projection on the respective axis). In other embodiments, the channels may extend substantially laterally, which means that each channel extends more in the lateral direction than in the longitudinal direction, or at least twice as much in the transverse direction than in the longitudinal direction (as measured after projection on the respective axis).

The channels may be completely oriented longitudinally and parallel to the longitudinal axis or completely oriented transversely and parallel to the lateral axis, but also may be curved. In various embodiments, some or all of the channels, in particular the channels present in the crotch region 7, may be concave towards the longitudinal axis 80, as, for example, represented in FIG. 1 for the pair of channels 26, 26', such that they bend towards the longitudinal axis 80. The channels 26, 26' may also be convex, such they bend away from the longitudinal axis 80, or have any other suitable arrangement. The radius of curvature may typically be at least equal (and may be at least 1.5 or at least 2.0 times this average transverse dimension) to the average transverse dimension of the absorbent layer; and also straight but under an angle of (e.g., from 5°) up to 30°, up to 20°, up to 10° with a line parallel to the longitudinal axis. The radius of curvature may be constant for a channel, or may vary along its length. This may also include channels with an angle therein, provided the angle between two parts of a channel is at least 120°, at least 150°; and in any of these cases, provided the longitudinal extension of the channel is more than the transverse extension. The channels may also be branched. For example, a central channel superposed with the longitudinal axis in the crotch region 7 which branches towards the rear waist edge 12 and/or towards the front waist edge 10 of the absorbent article.

In some embodiments, there may be a channel coincides with the longitudinal axis 80 of the absorbent article or the core, while in other embodiments there may not be a channel that coincides with the longitudinal axis 80. When present as symmetrical pairs relative to the longitudinal axis 80, the channels may be spaced apart from one another over their whole longitudinal dimension. The smallest spacing distance may be at least 5 mm, at least 10 mm, or at least 15 mm, for example.

Furthermore, in order to reduce the risk of fluid leakages, the longitudinal main channels may not extend up to any of the edges of the absorbent material deposition area 8, and may therefore be fully encompassed within the absorbent material deposition area 8 of the core. The smallest distance between a channel and the closest edge of the absorbent material deposition area 8 may be at least 5 mm.

The channels may have a width Wc1 along at least part of its length which is at least 2 mm, at least 3 mm, at least 4 mm, up to for example 20 mm, 16 mm, or 12 mm, for example. The width of the channel may be constant through substantially the whole length of the channel or may vary along its length. When the channels are formed by absorbent material-free zones within the absorbent material deposition area 8, the width of the channels is considered to be the width of the material-free zones, disregarding the possible presence of the core wrap within the channels. If the channels are not formed by absorbent material-free zones, for example mainly through bonding of the core wrap through the absorbent material zone, the width of the channels is the width of this bonding.

At least some or all of the channels may be permanent channels, meaning their integrity is at least partially maintained both in the dry state and in the wet state. Permanent channels may be obtained by provision of one or more adhesive materials, for example, the fibrous layer of adhesive material or construction glue that helps adhere a substrate with an absorbent material within the walls of the channel. Permanent channels may also be formed by bonding the upper side and lower side of the core wrap (e.g., the first substrate 16 and the second substrate 16') and/or the topsheet 24 to the backsheet 25 together through the channels. Typically, an adhesive may be used to bond both sides of the core wrap or the topsheet and the backsheet through the channels, but it is possible to bond via other known processes, such as pressure bonding, ultrasonic bonding, heat bonding, or combination thereof. The core wrap or the topsheet 24 and the backsheet 25 may be continuously bonded or intermittently bonded along the channels. The channels may advantageously remain or become visible at least through the topsheet and/or backsheet when the absorbent article is fully loaded with a fluid. This may be obtained by making the channels substantially free of SAP, so they will not swell, and sufficiently large so that they will not close when wet. Furthermore, bonding the core wrap to itself or the topsheet to the backsheet through the channels may be advantageous.

In an embodiment, referring to FIG. 1, the absorbent core 28 may comprise at least three channels or four channels (e.g., 26, 26', 27, 27'). These channels may be free of, or substantially free of (e.g., less than 10%, less than 5%, less than 3%, less than 2%, or less than 1%), superabsorbent polymers and may be at least partially oriented in the longitudinal direction and/or may be at least partially oriented in the lateral direction. In various embodiments, the longitudinal lengths of the channels 26 and 26' about the longitudinal axis 80 may be the same, substantially the same (e.g., within 2 mm or less of each other), or different and the longitudinal lengths of the channels 27 and 27' about the longitudinal axis 80 may be the same, substantially the same, or different. The longitudinal length of the channels 26 and 26' may be larger than the longitudinal length of the channels 27 and 27'. The average lateral width over the longitudinal lengths of the channels 27 and 27' may be the same, substantially the same, or may be different. Likewise, the average lateral width over the longitudinal lengths of the channels 26 and 26' may be the same, substantially the same, or may be different. The average lateral width of any of the channels 26, 26', 27, and 27' may be the same, substantially the same, or different.

In some embodiments, in addition to the first and second channels 26 and 26', an absorbent core 28 may comprise a pocket (not shown) in the crotch region 7 and/or the rear waist region 6 and one or more channels in the rear waist region 6 and/or the crotch region 7. In another embodiment, a pocket may be in the crotch region 7 and/or the front waist region 5 and the one or more channels may be in the crotch region 7 and/or the front waist region 5. The pocket and the one or more channels may be BM pockets or channels and/or urine management pockets and/or channels.

Barrier Leg Cuffs

The absorbent article may comprise a pair of barrier leg cuffs 34. Each barrier leg cuff may be formed by a piece of material which is bonded to the absorbent article so it can extend upwards from the inner surface of the absorbent article and provide improved containment of liquids and other body exudates approximately at the junction of the torso and legs of the wearer. The barrier leg cuffs 34 are delimited by a proximal edge 64 joined directly or indirectly to the topsheet 24 and/or the backsheet 25 and a free terminal edge 66, which is intended to contact and form a seal with the wearer's skin. The barrier leg cuffs 34 extend at least partially between the front waist edge 10 and the rear waist edge 12 of the absorbent article on opposite sides of the longitudinal axis 80 and are at least present at the level of the crotch point (C) or crotch region. The barrier leg cuffs 34 may be joined at the proximal edge 64 with the chassis of the absorbent article by a bond 65 which may be made by gluing, fusion bonding, or combination of other suitable bonding processes. The bond 65 at the proximal edge 64 may be continuous or intermittent. The bond 65 closest to the raised section of the leg cuffs 34 delimits the proximal edge 64 of the standing up section of the leg cuffs 34.

The barrier leg cuffs 34 may be integral with the topsheet 24 or the backsheet 25 or may be a separate material joined to the absorbent article's chassis. The material of the barrier leg cuffs 34 may extend through the whole length of the diapers but may be "tack bonded" to the topsheet 24 towards the front waist edge 10 and rear waist edge 12 of the absorbent article so that in these sections the barrier leg cuff material remains flush with the topsheet 24.

Each barrier leg cuff 34 may comprise one, two or more elastic strands or strips of film 35 close to this free terminal edge 66 to provide a better seal.

In addition to the barrier leg cuffs 34, the absorbent article may comprise gasketing cuffs 32, which are joined to the chassis of the absorbent article, in particular to the topsheet 24 and/or the backsheet 25 and are placed externally relative to the barrier leg cuffs 34. The gasketing cuffs 32 may provide a better seal around the thighs of the wearer. Each gasketing leg cuff may comprise one or more elastic strings or elastic elements in the chassis of the absorbent article between the topsheet 24 and backsheet 25 in the area of the leg openings. All or a portion of the barrier leg and/or gasketing cuffs may be treated with a lotion or skin care composition. The barrier leg cuffs may be constructed in a number of different configurations, including those described in U.S. Pat. App. Publ. No. 2012/0277713.

Fastening System

The absorbent article may include a fastening system. The fastening system may be used to provide lateral tensions about the circumference of the absorbent article to hold the absorbent article on the wearer as is typical for taped diapers. This fastening system may not be necessary for training pant or pant-style articles since the waist region of these articles is already bonded. The fastening system may comprise a fastener such as tape tabs, hook and loop fastening components, interlocking fasteners such as tabs & slots, buckles, buttons, snaps, and/or hermaphroditic fastening components, although any other suitable fastening mechanisms are also within the scope of the present disclosure. A landing zone 44 is normally provided on the garment-facing surface of the front waist region 5 for the fastener to be releasably attached thereto.

The fastening system may also include primary and secondary fastening systems, as disclosed in U.S. Pat. No. 4,699,622 to reduce shifting of overlapped portions or to improve fit as disclosed in U.S. Pat. Nos. 5,242,436, 5,499, 978, 5,507,736, and 5,591,152.

Front and Rear Ears

In an embodiment, the absorbent article may comprise front ears 46 and rear ears 40. The ears may be an integral part of the chassis, such as formed from the topsheet 24 and/or backsheet 25 as side panel. Alternatively, as represented on FIG. 1, the ears (46, 40) may be separate elements attached by gluing, heat embossing, and/or pressure bonding. The rear ears 40 may be stretchable to facilitate the attachment of the tabs 42 to the landing zone 44 and maintain the taped diapers in place around the wearer's waist. The rear ears 40 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

Elastic Waist Feature

The absorbent article may also comprise at least one elastic waist feature (not represented) that helps to provide improved fit and containment. The elastic waist feature is generally intended to elastically expand and contract to dynamically fit the wearer's waist. The elastic waist feature may extend at least longitudinally outwardly from at least one waist edge of the absorbent core 28 and generally forms at least a portion of the end edge of the absorbent article. Disposable diapers may be constructed so as to have two elastic waist features, one positioned in the front waist region and one positioned in the rear waist region. The elastic waist feature may be constructed in a number of different configurations including those described in U.S. Pat. Nos. 4,515,595; 4,710,189; 5,151,092; 5,221,274; U.S. Pat. Appl. Publ. No. 2012/0330262; U.S. Pat. App. Publ. No. 2012/0330263; and U.S. Pat. App. Pub. No. 2012/0330264.

Relations Between the Layers

Typically, adjacent layers and components may be joined together using conventional bonding methods, such as adhesive coating via slot coating or spraying on the whole or part of the surface of the layer, thermo-bonding, pressure bonding, or combinations thereof. Bonding between the layers of the absorbent article may or may not be present. Bonding is not represented in the Figures (except for the bonding between the raised elements of the leg cuffs 34 with the topsheet 24) for clarity and readability. Adhesives may be used to improve the adhesion of the different layers between the backsheet 25 and the core wrap. The glue may be any suitable hotmelt glue known in the art.

If an acquisition layer 52 is present in the LMS 50, it may be desired that this acquisition layer is larger than or least as large as the distribution layer 54 in the longitudinal and/or transversal dimension. Thus, the distribution layer 54 may be deposited on the acquisition layer 52. This simplifies handling, in particular if the acquisition layer is a nonwoven which may be unrolled from a roll of stock material. The distribution layer 54 may also be deposited directly on the absorbent core's upper side of the core wrap or another layer of the absorbent article. Also, having an acquisition layer 52 that is larger than the distribution layer allows for direct gluing of the acquisition layer to the storage core (at the larger areas). This may provide increased patch integrity and better liquid communication.

The absorbent core, and in particular its absorbent material deposition area 8, may be at least as large and long and at least partially larger and/or longer than the liquid management system. This is because the absorbent material in the core may more effectively retain fluid and provide dryness benefits across a larger area than the LMS 50. The absorbent article may have a rectangular SAP layer and a non-rectangular (shaped) LMS 50. The absorbent article may also have a rectangular (non-shaped) LMS 50 and a rectangular layer of SAP.

Liquid Management System

The LMS 50 of the present disclosure may sometimes be referred to as acquisition-distribution system ("ADS") or an acquisition system. One function of the LMS 50 is to quickly acquire the fluid and distribute it to the absorbent core in an efficient manner. The LMS 50 may comprise one, two or more layers, which may form a unitary layer or may remain as discrete layers which may be attached to each other. In an embodiment, the LMS 50 may comprise two layers: a distribution layer 54 and an acquisition layer 52 disposed between the absorbent core and the topsheet, but the present disclosure is not limited to this embodiment.

The LMS 50 may comprise SAP as this may slow the acquisition and distribution of the fluid. In other embodiments, the LMS may be substantially free (e.g., 80%, 85%, 90%, 95%, or 99% free of) or completely free of SAP. The LMS may also comprise one or more of a variety of other suitable types of materials, such as opened-cell foam, airlaid fibers, or carded, resin bonded nonwoven materials, for example. Suitable example LMSs are described in WO 2000/59430 (Daley), WO 95/10996 (Richards), U.S. Pat. No. 5,700,254 (McDowall), and WO 02/067809 (Graef), for example. Any of the example LMSs 50 disclosed herein may be positioned in an absorbent article: (1) intermediate a liquid pervious material or topsheet or secondary topsheet and an absorbent core; (2) intermediate an absorbent core and a liquid impervious material or backsheet; (3) intermediate an absorbent core and a liquid distribution layer; (4) intermediate a liquid distribution layer and a liquid impervious material or backsheet, or may be otherwise located within the absorbent article. In an embodiment, more than one LMS 50 may be provided in an absorbent article. The one or more LMSs 50 may be provided above and/or below one or more absorbent cores.

Distribution Layer

In certain embodiments, the LMS 50 may comprise a distribution layer 54. The distribution layer 54 may comprise at least 50% by weight of cross-linked cellulose fibers, for example. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf). The cross-linked cellulosic fibers provide higher resilience and therefore higher resistance to the first absorbent layer against the compression in the product packaging or in use conditions, e.g., under baby weight. This provides the core with a higher void volume, permeability, and liquid absorption, and hence reduced leakage and improved dryness.

Example chemically cross-linked cellulosic fibers suitable for a distribution layer are disclosed in U.S. Pat. Nos. 5,549,791, 5,137,537, WO 9534329, or U.S. Pat. App. Publ. No. 2007/118087. Example cross-linking agents include polycarboxylic acids such as citric acid and/or polyacrylic acids such as acrylic acid and maleic acid copolymers.

The distribution layer 54 comprising cross-linked cellulose fibers of the present disclosure may comprise other fibers, but this layer may advantageously comprise at least 50%, or 60%, or 70%, or 80%, or 90%, or even up to 100%, by weight of the layer, of cross-linked cellulose fibers (including the cross-linking agents). Examples of such mixed layer of cross-linked cellulose fibers may comprise about 70% by weight of chemically cross-linked cellulose fibers, about 10% by weight polyester (PET) fibers, and about 20% by weight untreated pulp fibers. In another example, the layer of cross-linked cellulose fibers may comprise about 70% by weight chemically cross-linked cellulose fibers, about 20% by weight lyocell fibers, and about 10% by weight PET fibers. In another example, the layer may comprise about 68% by weight chemically cross-linked cellulose fibers, about 16% by weight untreated pulp fibers, and about 16% by weight PET fibers. In another example, the layer of cross-linked cellulose fibers may comprise from about 90-100% by weight chemically cross-linked cellulose fibers.

The distribution layer 54 may be a material having a water retention value of from 25 to 60 or from 30 to 45, measured as indicated in the procedure disclosed in U.S. Pat. No. 5,137,537.

The distribution layer may typically have an average basis weight of from 30 to 400 g/m$^2$ or from 100 to 300 g/m$^2$, specifically reciting all 1.0 g/m$^2$ increments within the above-specified ranges and any ranges formed therein or thereby. The density of the distribution layer may vary depending on the compression of the absorbent article, but may be between 0.03 to 0.15 g/cm3 or 0.08 to 0.10 g/cm3, specifically reciting all 1.0 g/cm3 increments within the above-specified ranges and any ranges formed therein or thereby, measured at 0.30 psi (2.07 kPa).

Acquisition Layer

In certain embodiments, the LMS 50 may alternatively or additionally comprise an acquisition layer 52. In an embodiment, the acquisition layer 52 may be disposed, for example, between the distribution layer 54 and the topsheet 24. The acquisition layer 52 may be or may comprise a non-woven material, such as an SMS or SMMS material, comprising a spunbonded, a melt-blown and a further spunbonded layer or alternatively a carded chemical-bonded nonwoven. In some embodiments, the acquisition layer 52 may comprise air or wet-laid cellulosic, cross-linked cellulosic, or synthetic fibers, or blends thereof. In certain embodiments, the acquisition layer 52 may comprise a roll-stock web of synthetic fibers (which may be processed to increase void space, such as by solid state formation), or a combination of synthetic and cellulosic fibers, bonded together to form a highloft material. Alternatively, the acquisition layer 52 may comprise absorbent open cell foam. The nonwoven material may be latex bonded. Example acquisition layers are disclosed in U.S. Pat. No. 7,786,341. Carded, resin-bonded nonwovens may be used, in particular where the fibers used are solid round or round hollow PET staple fibers (50/50 or 40/60 mix of 6 denier and 9 denier fibers). An example binder is a butadiene/styrene latex. Nonwovens have the advantage that they can be manufactured outside the converting line and stored and used as a roll of material. The acquisition layer 52 may be stabilized by a latex binder, for example a styrene-butadiene latex binder (SB latex).

A further acquisition layer may be used in addition to a first acquisition layer described above. For example, a tissue, nonwoven, or other layer may be placed between the first acquisition layer and the distribution layer. The tissue may have enhanced capillarity distribution properties compared to the acquisition layer described above. The tissue, nonwoven, or other layer and the first acquisition layer may be of the same size or may be of a different size. For example, the tissue, nonwoven, or other layer may extend further in the rear of the absorbent article than the first acquisition layer. An example of hydrophilic tissue is a 13-15 gsm high wet strength made of cellulose fibers from supplier Havix.

The composition used to form fibers for the base substrate of the acquisition layer 52 may comprise thermoplastic polymeric and non-thermoplastic polymeric materials. The thermoplastic polymeric material must have rheological characteristics suitable for melt spinning. The molecular weight of the polymer must be sufficient to enable entanglement between polymer molecules and yet low enough to be melt spinnable. For melt spinning, thermoplastic polymers have molecular weights below about 1,000,000 g/mol; from about 5,000 g/mol to about 750,000 g/mol; from about 10,000 g/mol to about 500,000 g/mol; and from about 50,000 g/mol to about 400,000 g/mol. Unless specified elsewhere, the molecular weight indicated is the number average molecular weight.

The thermoplastic polymeric materials are able to solidify relatively rapidly, preferably under extensional flow, and form a thermally stable fiber structure, as typically encountered in known processes such as a spin draw process for staple fibers or a spunbond continuous fiber process. Polymeric materials may comprise, but are not limited to, polypropylene and polypropylene copolymers, polyethylene and polyethylene copolymers, polyester and polyester copolymers, polyamide, polyimide, polylactic acid, polyhydroxyalkonoate, polyvinyl alcohol, ethylene vinyl alcohol, polyacrylates, and copolymers thereof and mixtures thereof. Other suitable polymeric materials include thermoplastic starch compositions as described in detail in U.S. Pat. App. Publ. No. 2003/0109605A1 and 2003/0091803. Other suitable polymeric materials include ethylene acrylic acid, polyolefin carboxylic acid copolymers, and combinations thereof. The polymers described in U.S. Pat. Nos. 6,746,766, 6,818,295, and 6,946,506 and U.S. Pat. App. Ser. No. 03/0092343. Common thermoplastic polymer fiber grade materials may be used, such as polyester based resins, polypropylene based resins, polylactic acid based resin, polyhydroxyalkonoate based resin, and polyethylene based resin and combination thereof. Some embodiments use polyester and polypropylene based resins.

Nonlimiting examples of thermoplastic polymers suitable for use in the present disclosure include aliphatic polyester-amides; aliphatic polyesters; aromatic polyesters including polyethylene terephthalates (PET) and copolymer (coPET), polybutylene terephthalates and copolymers; polytrimethylene terephthalates and copolymers; polypropylene terephthalates and copolymers; polypropylene and propylene copolymers; polyethylene and polyethylene copolymers; aliphatic/aromatic copolyesters; polycaprolactones; poly(hydroxyalkanoates) including poly(hydroxybutyrate-co-hydroxyvalerate), poly(hydroxybutyrate-co-hexanoate), or other higher poly(hydroxybutyrate-co-alkanoates) as referenced in U.S. Pat. No. 5,498,692 to Noda; polyesters and polyurethanes derived from aliphatic polyols (i.e., dialkanoyl polymers); polyamides; polyethylene/vinyl alcohol copolymers; lactic acid polymers including lactic acid homopolymers and lactic acid copolymers; lactide polymers including lactide homopolymers and lactide copolymers; glycolide polymers including glycolide homopolymers and glycolide copolymers; and mixtures thereof. Additional examples include aliphatic polyesteramides, aliphatic polyesters, aliphatic/aromatic copolyesters, lactic acid polymers, and lactide polymers.

Suitable lactic acid and lactide polymers include those homopolymers and copolymers of lactic acid and/or lactide which have a weight average molecular weight generally ranging from about 10,000 g/mol to about 600,000 g/mol; from about 30,000 g/mol to about 400,000 g/mol; or from about 50,000 g/mol to about 200,000 g/mol. An example of commercially available polylactic acid polymers includes a variety of polylactic acids that are available from the Chronopol Incorporation located in Golden, Colorado, and the polylactides sold under the tradename EcoPLA®. Examples of suitable commercially available polylactic acid are NATUREWORKS from Cargill Dow and LACEA from Mitsui Chemical. Homopolymers or copolymers of poly lactic acid having a melting temperature from about 160° to about 175° C. may be used. Modified poly lactic acid and different stereo configurations may also be used, such as poly L-lactic acid and poly D,L-lactic acid with D-isomer levels up to 75%. Optional racemic combinations of D and L isomers to produce high melting temperature PLA polymers may be used. These high melting temperature PL polymers are special PLA copolymers (with the understanding that the D-isomer and L-isomer are treated as different stereo monomers) with melting temperatures above 180° C. These high melting temperatures are achieved by special control of the crystallite dimensions to increase the average melting temperature.

Depending upon the specific polymer used, the process, and the final use of the fiber, more than one polymer may be desired. The polymers of the present disclosure are present in an amount to improve the mechanical properties of the fiber, the opacity of the fiber, optimize the fluid interaction with the fiber, improve the processability of the melt, and improve attenuation of the fiber. The selection and amount of the polymer will also determine if the fiber is thermally bondable and affect the softness and texture of the final product. The fibers of the present disclosure may comprise a single polymer, a blend of polymers, or be multicomponent fibers comprising more than one polymer. The fibers in the present disclosure are thermally bondable.

Multiconstituent blends may be desired. For example, blends of polyethylene and polypropylene (referred to hereafter as polymer alloys) can be mixed and spun using this technique. Another example would be blends of polyesters with different viscosities or monomer content. Multicomponent fibers can also be produced that contain differentiable chemical species in each component. Non-limiting examples would include a mixture of 25 melt flow rate (MFR) polypropylene with 50MFR polypropylene and 25MFR homopolymer polypropylene with 25MFR copolymer of polypropylene with ethylene as a comonomer.

The polymeric materials may have melting temperatures above 110° C., above 130° C., above 145° C., above 160° C. or above 200° C. Polymers with high glass transition temperatures may be desired. Glass transition temperatures in the end-use fiber form may be used that are above −10° C., which are above 0° C., which are above 20° C., or that are above 50° C. This combination of properties produces fibers that are stable at elevated temperatures. Examples of materials of this type are polypropylene, polylactic acid based polymers, and polyester terephthalate (PET) based polymer systems.

Channels in Liquid Management System

The LMS 50 of the absorbent article 20 may comprise channels that may generally enable better conformation of the absorbent article to the wearer's anatomy, leading to increased freedom-of-movement and reduced gapping. One or more of the channels of the LMS 50 may be configured to work in concert with various channels in the absorbent core 28, as discussed above. Furthermore, channels in the LMS 50 may also provide increased void space to hold and distribute urine, feces or other body exudates within the absorbent article, leading to reduced leakage and skin contact. In some embodiments, channels in the LMS 50 may also provide internal serviceable indicia, especially when highlighted via physical differences in texture, color and/or pattern, to facilitate achieving the correct alignment of the absorbent article on a wearer. Thus, such physical differences may be, for example, visually and/or tactilely noticeable.

Similar to the channels in the absorbent core 28, a channel in the LMS 50 may be any region in a layer, or extending through more than one layer, that has a substantially lower basis weight or thickness than the surrounding material, as set forth in the definition of "channel" above. The channels in the LMS 50 may also serve to reduce the tension forces to enable controlled bending and maintain the LMS 50 in close proximity to the absorbent core 28. Thus, the presence of channels in the LMS 50, which may or may not be aligned with any channels in an underlying absorbent core 28, may generally function as hinges to allow for a more flexible composite structure. In some cases, for example, the channels of the LMS 50 allow for the LMS 50 to move toward the absorbent core 28 in a controlled bending arrangement, thereby limiting the separation between the LMS 50 and the absorbent core 28. Moreover, in certain embodiments, a channel in the LMS 50 may assist in the routing of fluid or other bodily exudates from one region of the absorbent article 20 to another region of the absorbent article 20. Such routing may desirably improve the overall distribution of fluid through the absorbent article 20 and may lead to increase in comfort, wearability, or longevity of the article.

For multi-layered LMSs, the channels may be present in one or more layers of the LMS 50 and may vary in their dimensions in all three planes of reference. In an embodiment, the width of a given channel in the LMS 50 may vary in the longitudinal direction (i.e., in a direction substantially parallel to the longitudinal axis of the absorbent article). A channel may also have a different width, length, and/or volume in front of a lateral axis or lateral separation element of the absorbent article than behind the lateral axis or lateral separation element. The channels of the LMS 50 may have a range of widths, lengths, shapes, volumes, and patterns, similar to the channels described above with regard to the absorbent core 28.

In certain embodiments, a channel in the LMS 50 of the back portion of an absorbent article may be referred to as a bowel movement "BM" channel or BM pocket and may be generally aligned with and overlapping the longitudinal centerline in the back portion of the absorbent article or may be otherwise located. A portion of the channel may be positioned in the LMS 50 such that is generally aligns with the wearer's ischium and may have a width in the range of about 10 mm to about 30 mm, for example. Rearward of this location, the channel width may or may not increase gradually or abruptly to about 25 mm to about 150 mm, for example. In an embodiment, the width of the channel may decrease again as it approaches the rear waist region of the absorbent article. The volume of the channel may be in the range of about 10 cm$^3$ to about 200 cm$^3$, for example. The ratio of the maximum channel width to the width at the wearer's ischium may range from about 1.5 to about 15. In an embodiment, at least about 60%, at least about 70%, at least about 75%, at least about 80%, or at least about 85% of the total volume of all the channels in the LMS may lie rearward of the lateral centerline. In an embodiment, at least about 60% to about 85% of the total volume of all the channels in the LMS may lie rearward of the lateral centerline.

One or more channels in the LMS 50 may at least partially overlap, or fully overlap, a channel in the absorbent core 28, creating a deeper recess in the overlapping regions. For embodiments where the LMS 50 includes more than one layer, the layer closest to the absorbent core 28 may include a channel. One or more layers in the structure, such as the topsheet 24, an acquisition layer 52, distribution layer 54, or other layers, may be bonded to an element of the absorbent core 28 in this region to increase the depth of the combined channel. In an embodiment, the channel in the acquisition layer 52 of the LMS 50 and the channel in the absorbent core 28 are coincident such that the channels are completely overlapping. In another embodiment, channels in the LMS and storage layers have no overlapping area. Other embodiments have a vertical overlap between the channels in the two layers that encompass the intervening range such that they partially overlap. Example channel arrangements are described in more detail below with regard to FIGS. 11-26.

In embodiments where the topsheet 24 includes apertures, the apertures may be fully or partially aligned or overlapping with at least one channel in the LMS 50, whereas in other embodiments, the apertures may not align with any channel in the LMS 50. In some embodiments, at least one layer on or proximate to the garment-facing side and/or the wearer-side of the absorbent article 20 may include a pattern, image, color, or tint resulting in an increased visual distinctiveness of the channel of the LMS 50 and serve as an internal serviceable indicia to facilitate more accurate alignment of the absorbent article on the wearer during the application process.

Referring again to FIGS. 1-5, the LMS 50 in the illustrated example embodiment is shown defining two channels 49, 49'. The channels 49, 49' are at least partially oriented in the longitudinal direction of the absorbent article 80 (i.e., has a longitudinal vector component). Other channels in the LMS may be at least partially oriented in the lateral direction (i.e., has a lateral vector component) or in any other direction and the channels in the LMS 50 may be continuous or intermittent. Some channels in the LMS may be round, oblong, square, rectangular, triangular or any other suitable shape. The channels may have a length projected on the longitudinal axis 80 of the absorbent article that is at least 10% of the length L of the absorbent article. The channels may be formed in various ways. For example, the channels may be formed by zones within the LMS 50 which may be substantially free of, or free of, acquisition or distribution material.

In some embodiments, the channels of the LMS 50 may be present at least at the same longitudinal level as the crotch point C or the lateral axis 90 in the absorbent article, as represented in FIG. 1 with the two longitudinally extending channels 49, 49'. The channels may also extend from the crotch region 7 or may be present in the front waist region 5 and/or in the rear waist region 6 of the absorbent article. In FIG. 1, the channels 49, 49' are generally coincident with channels 26, 26', with channels 26, 26' having a longer length in the longitudinal direction towards the front waist edge 10 of the absorbent article 20.

The LMS 50 may define any suitable number of channels, such as at least one, more than two channels, at least three, at least four, at least five, or at least six or more. Shorter channels may also be present, for example in the rear waist region 6 or the front waist region 5 of the LMS 50. The channels of the LMS 50 may comprise one or more pairs of channels symmetrically arranged, or otherwise arranged relative to the longitudinal axis 80 and/or the lateral axis 90, or other transverse axis.

The channels of the LMS 50 may extend substantially longitudinally, which means that each channel extends more in the longitudinal direction than in the transverse direction, or at least twice as much in the longitudinal direction than in the transverse direction (as measured after projection on the respective axis). In other embodiments, the channels of the LMS 50 may extend substantially laterally, which means that each channel extends more in the lateral direction than in the longitudinal direction, or at least twice as much in the transverse direction than in the longitudinal direction (as measured after projection on the respective axis).

Similar to the channels in the absorbent core, the channels of the LMS 50 may be completely oriented longitudinally and parallel to the longitudinal axis or completely oriented transversely and parallel to the lateral axis, but also may be curved or have a combination of curved and linear components. In various embodiments, some or all the channels, in particular the channels of the LMS 50 present in the crotch region 7, may be concave with respect to the longitudinal axis 80, as, for example, represented in FIG. 1 for the pair of channels 49, 49', such that they bend towards the longitudinal axis 80. The channels 49, 49' may also be convex, such they bend away from the longitudinal axis 80, or have any other suitable arrangement. The channels 49, 49 may generally align with the channels 26, 26' in the absorbent core, although this disclosure is not so limited. The radius of curvature may typically be at least equal (and may be at least 1.5 or at least 2.0 times this average transverse dimension) to the average transverse dimension of the absorbent layer; and also straight but under an angle of (e.g., from 5°) up to 30°, up to 20°, up to 10° with a line parallel to the longitudinal axis. The radius of curvature may be constant for a channel, or may vary along its length. This may also include channels with an angle therein, provided the angle between two parts of a channel is at least 120°, at least 150°; and in any of these cases, provided the longitudinal extension of the channel is more than the transverse extension.

The channels of the LMS 50 may also be branched. For example, a central channel superposed with the longitudinal axis in the crotch region 7 which branches towards the rear waist edge 12 and/or towards the front waist edge 10 of the absorbent article. In some embodiments, there is no channel in the LMS 50 that coincides with the longitudinal axis 80 of the absorbent article. When present as symmetrical pairs relative to the longitudinal axis 80, the channels may be spaced apart from one another over their whole longitudinal dimension. The smallest spacing distance may be at least 5 mm, at least 10 mm, or at least 15 mm, for example.

Furthermore, in order to reduce the risk of fluid leakages, the channels of the LMS 50 may therefore be fully encompassed within the LMS 50. The smallest distance between a channel and the closest edge of the LMS 50 may be at least 5 mm.

The channels of the LMS 50 may have a width Wc2 (FIG. 1) along at least part of its length which is at least 2 mm, at least 3 mm, at least 4 mm, up to for example 20 mm, 16 mm, or 12 mm, for example. The width of the channel may be constant through substantially the whole length of the channel or may vary along its length. The channels of the LMS 50 may have similar or different widths Wc2 than the widths Wc1 of channels within the absorbent core 28. In the embodiment illustrated in FIG. 1, while Wc1 is substantially equal to Wc2, the length of the channels in the absorbent core 28 may exceed the length of the channels in the LMS 50 such that the channels 26, 26' extend closer to the front waist edge 10. In other embodiments, however, the channels 49, 49' may extend closer to the front waist edge 10.

When the channels within the LMS 50 are formed by material-free zones, the width of the channels (Wc2) is considered to be the width of the material-free zone, disregarding the possible presence of the topsheet 24, or other layers, within the channels. If the channels are formed by zones of reduced basis weight, the width of the channels may be the width of the zones of reduced basis weight.

At least some or all of the channels in the LMS 50 may be permanent channels, meaning their integrity is at least partially maintained both in the dry state and in the wet state. Permanent channels may be obtained by provision of one or more adhesive materials, for example, the fibrous layer of adhesive material or construction glue that helps adhere a substrate with an absorbent material within the walls of the channel. Permanent channels may also be formed by bonding the topsheet 24 to the backsheet 25 together through a channel of the LMS 50. Typically, an adhesive may be used to bond the topsheet 24 and the backsheet 25 through the channels, but it is possible to bond via other known processes, such as pressure bonding, ultrasonic bonding, heat bonding, or combination thereof. The topsheet 24 and the backsheet 25 may be continuously bonded or intermittently bonded along or within portions of or all of the channels. The channels may remain or become visible at least through the topsheet and/or backsheet when the absorbent article is fully loaded with a fluid. In some embodiments, channels of the LMS 50 may align with channels of the absorbent core 28, such that the channels are visible through a garment-facing surface when they contain urine or feces or when a bodily exudate is at least proximate to the channels (such as when a bodily exudate is on the topsheet 24 but not yet within a channel). Such channels may provide a visual indication to a caregiver that the absorbent article should be changed. In other embodiments, a graphical indicator or merely a graphic is printed on an outer surface or other layer of the absorbent article proximate to, over, or partially over the channels to visually obscure the bodily exudates contained within the channels.

In certain embodiments, an indicator may be included on one or more of the backsheet, a backsheet film, and/or a nonwoven dusting layer, for example, to visually indicate when a change of the absorbent article is required. The indicator may be configured to switch states in the presence of urine and/or feces. The indicator may be, for example, a line or graphic that changes from white or clear to blue. The indicator may also be a word, such a "dry", that disappears once urine is present in the channels. The indicator may be the word "wet" that appears in the presence of urine. Any other suitable indicator or a plurality of indicators may also be utilized.

In an embodiment, referring to FIG. 1, the LMS 50 may comprise at least two channels (e.g., 49, 49'). These channels may be free of, or substantially free of (e.g., less than 10%, less than 5%, less than 3%, less than 2%, or less than 1%), non-woven material or cross-linked cellulose fibers and may be at least partially oriented in the longitudinal direction and/or may be at least partially oriented in the lateral direction. In various embodiments, the longitudinal lengths of the channels 49 and 49' about the longitudinal axis 80 may be the same, substantially the same (e.g., within 2 mm or less of each other), or different and the longitudinal lengths of the channels 49 and 49' about the longitudinal axis 80 may be the same, substantially the same, or different. The average lateral width over the longitudinal lengths of the channels 49 and 49' may be the same, substantially the same, or may be different.

Figure 9:
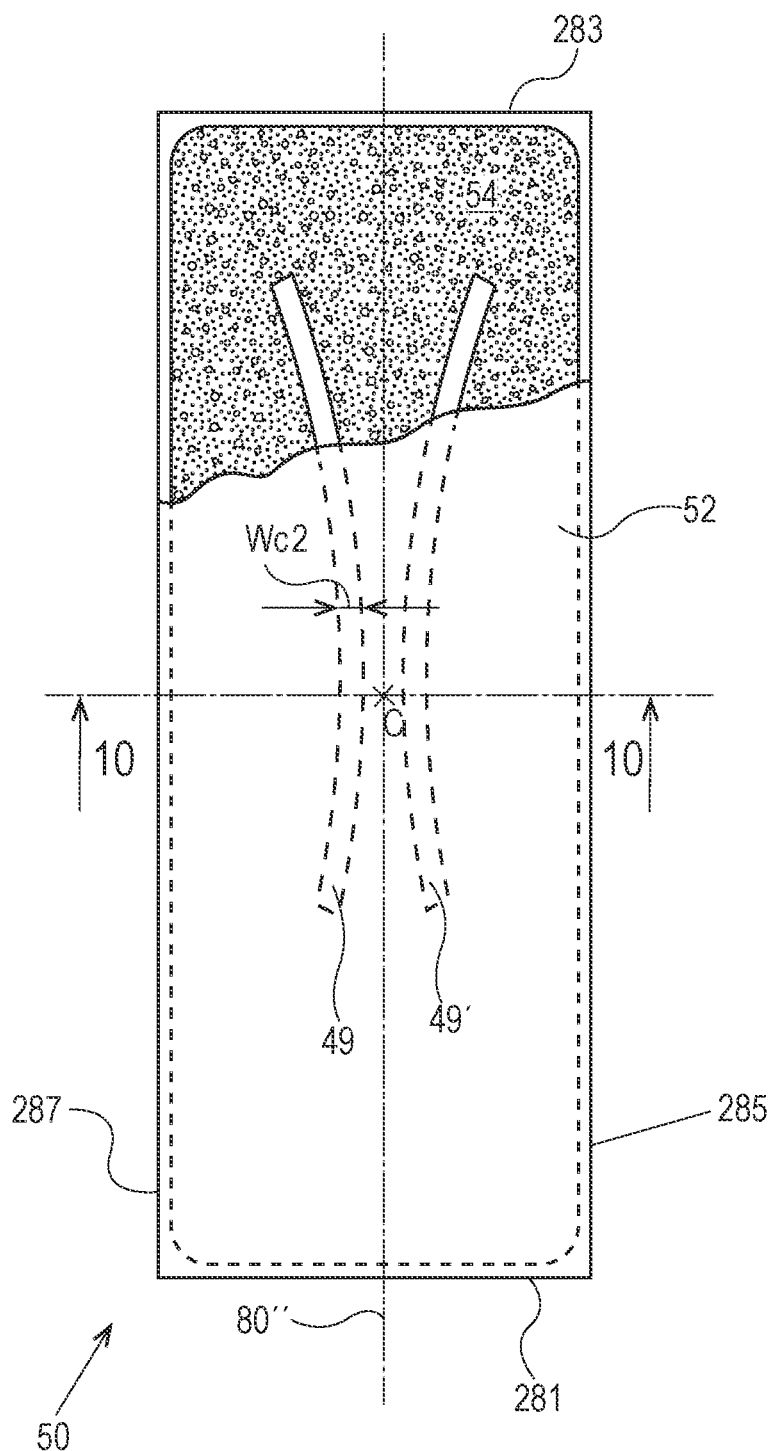
FIG. 9 is a top view of a liquid management system of the absorbent article of FIG. 4 with some layers partially removed in accordance with a non-limiting embodiment of the present disclosure.
Figure 10:
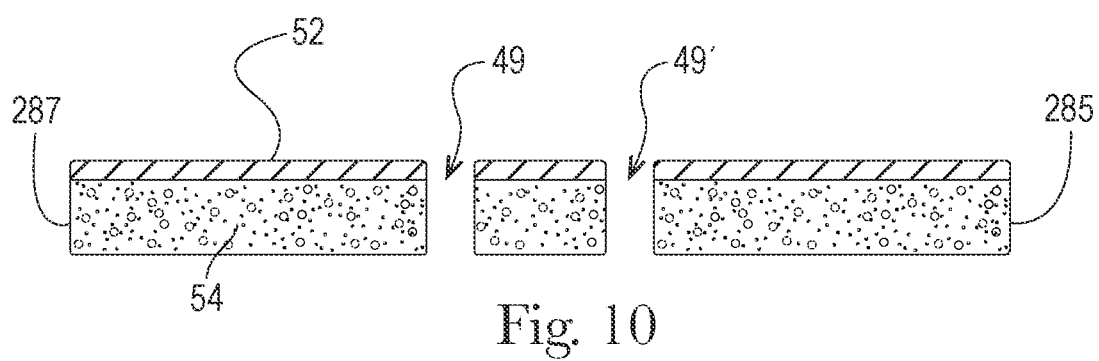
FIG. 10 is a cross-sectional view of the liquid management system taken about line 10-10 of FIG. 9 in accordance with a non-limiting embodiment of the present disclosure.

The example LMS 50 of the absorbent article of FIGS. 4-5 is shown in isolation in FIGS. 9-10 where FIG. 10 is a cross-sectional view of the LMS 50 taken about line 10-10 of FIG. 9. The LMS 50 may comprises a front side 281, a rear side 283, and two longitudinal sides 285, 287 joining the front side 281 and the rear side 283. The LMS 50 may also comprise a generally planar top side and a generally planar bottom side. The front side 281 of the LMS is the side of the LMS intended to be placed towards the front waist edge 10 of the absorbent article. The LMS 50 may have a longitudinal axis 80'' corresponding substantially to the longitudinal axis 80 of the absorbent article, as seen from the top in a planar view as in FIG. 1. The LMS 50 may comprise one or more layers. In the illustrated embodiment, the LMS 50 comprises a distribution layer 54 and an acquisition layer 52 which cooperate to define the channels 49, 49'. In other embodiments, less than all of the layers of the LMS 50 may define the channel such that at least one layer of the LMS 50 is continuous while another layer of the LMS 50 is discontinuous.

In certain embodiments, the LMS 50 may comprise a wrap or bag that is similar to the core wrap described above that is configured to hold particulates. In one example, the wrap may contain Functional Absorbent Materials ("FAM's") that generally function as a wicking/acquisition material. In a particular embodiment, the FAM may comprise an open-celled foam, in the form of a coherent web or sheet or in particulate form, prepared from High Internal Phase Emulsions (hereinafter referred to as "HIPEs"), as illustrated in (U.S. Pat. No. 5,331,015 (DesMarais et al.) issued Jul. 19, 1994, U.S. Pat. No. 5,260,345 (DesMarais et al.) issued Nov. 9, 1993, U.S. Pat. No. 5,268,224 (DesMarais et al.) issued Dec. 7, 1993, U.S. Pat. No. 5,632,737 (Stone et al.) issued May 27, 1997, U.S. Pat. No. 5,387,207 (Dyer et al.) issued Feb. 7, 1995, U.S. Pat. No. 5,786,395 (Stone et al.) Jul. 28, 1998, U.S. Pat. No. 5,795,921 (Dyer et al.)

issued Aug. 18, 1998), (U.S. Pat. No. 5,770,634 (Dyer et al.) issued Jun. 23, 1998, U.S. Pat. No. 5,753,359 (Dyer et al.) issued May 19, 1998, and U.S. Pat. No. 5,633,291 (Dyer et al.) issued May 27, 1997), (Bhumgara, Z. Filtration & Separation 1995, March, 245-251; Walsh et al. J. Aerosol Sci. 1996, 27, 5629-5630; published PCT application W/O 97/37745, published on Oct. 16, 1997, in the name of Shell Oil Co.).

While portions of the channels 26, 26' of the absorbent core 28 and the channels 49, 49' of the LMS 50 shown in FIGS. 1-10 are generally aligned, this disclosure is not so limited. In fact, as is to be appreciated, particular arrangements of the channels in an LMS 50 and/or an absorbent core 28 may vary. FIGS. 11-26 are simplified partial cross-sectional views of example absorbent articles that illustrate example configurations of the topsheet 24, the backsheet 25, the LMS 50 and the absorbent core 28. While FIGS. 11-26 illustrate a wide variety of channel arrangements, such arrangements are merely example arrangements and are not to be limiting, as a number of other channel arrangements are within the scope of the present disclosure. Further, various aspects of some of the figures may be incorporated into the arrangements of other figures without departing from the scope of the present disclosure.

Referring first to FIG. 11, an example channel arrangement is illustrated in which the LMS 50 defines a channel 49 and the absorbent core 28 does not define any channels. It is noted that while the LMS 50 is illustrated as a single-layer system in FIG. 11, among other figures, other embodiments may comprise a multi-layer LMS without departing from the scope of this disclosure.

FIG. 12 illustrates another example channel arrangement in which the channel 49 of the LMS 50 is generally aligned with the channel 26 of the absorbent core 28. While the channel 49 and the channel 26 are illustrated as having similar widths, in other embodiments the widths of the two channels may differ. In some embodiments, for example, the width of the channel 49 is wider or narrower than the width of the channel 26 along the entire aligned portion in the longitudinal direction. In other embodiments, the width of at least one of the channel 49 and the channel 26 may vary along the longitudinal direction, such that at some points along the overlapping portion, the channel 49 and the channel 26 have similar widths (as shown in FIG. 12), while at other points along the overlapping portion, the channels have different widths. For example, the channel 49 may have the same width along its entire longitudinal length while the channel 26 may have portions that are tapered or flared, or vice versa. In some embodiments, the channel 49, or at least portions of the channel 49, of the LMS 50 may not overlap the channel 26 of the absorbent core 26. In such cases, the channel width of the channel 49 may be the same or different as the channel width of the channel 26. Additionally, the relative similarities or differences of the channel widths may vary along respective longitudinal lengths of the channels 49, 26.

FIG. 13 illustrates an embodiment in which a portion of the topsheet 24 is recessed into the channel 49 defined by the LMS 50 and the channel 26 defined by the absorbent core 26. In some embodiments, the topsheet 24 is intermittently or continually bonded to the backsheet 25 along the channel to form a recess or groove that is visible from the wearer-facing side of the absorbent article. An adhesive may be used to bond the topsheet 24 and the backsheet 25 through the channels, although other known processes may be used to form the bond, such as pressure bonding, ultrasonic bonding, heat bonding, or combinations thereof.

FIG. 14 illustrates an embodiment in which the topsheet 24 comprises a contoured element 24' that generally aligns with the channel 49 defined by the LMS 50. The contoured element 24' may be any suitable three-dimensional structure, such as a groove, ridge, or other element formed into the topsheet 24. In some embodiments the contoured element 24' of the topsheet 24 has a different thickness or basis weight than other regions of the topsheet 24. In some embodiments, other layers of the absorbent article, such as the LMS 50 and/or the absorbent core 28 additionally or alternatively comprise a three-dimensional structure generally aligned with a channel in the absorbent article. By way of comparison to FIG. 13, for example, the contoured element 24' of FIG. 14 does not necessarily have to be bonded to backsheet 25 to maintain its relative placement within the channel 49. In some embodiments, the contoured element 24' may be deeper than the illustrated example such that it is recessed into both the channel 49 and the channel 26. In an embodiment, both the topsheet 24 and the backsheet 25 include countered elements that are recessed into channel 26 and channel 49 of the LMS 50 and the absorbent core 28, respectively.

FIG. 15 illustrates an embodiment in which both the topsheet 24 and the backsheet 25 are recessed into channels defined by the LMS 50 and the absorbent core 28, respectively. Similar to the embodiment illustrated in FIG. 13, the topsheet 24 may be intermittently or continually bonded to the backsheet 25 along the channel. Any suitable technique or combination of techniques may be used to bond the topsheet 24 and the backsheet 25. Furthermore, while in the illustrated embodiment, the topsheet 24 and backsheet 25 are bonded proximate to the interface between the LMS 50 and the absorbent core 28, this disclosure is not so limited. In other words, in some embodiments, the topsheet 24 may be recessed further into the channels than the backsheet 25 or the backsheet 25 may be recessed further into the channels than the topsheet 24.

Figure 17:
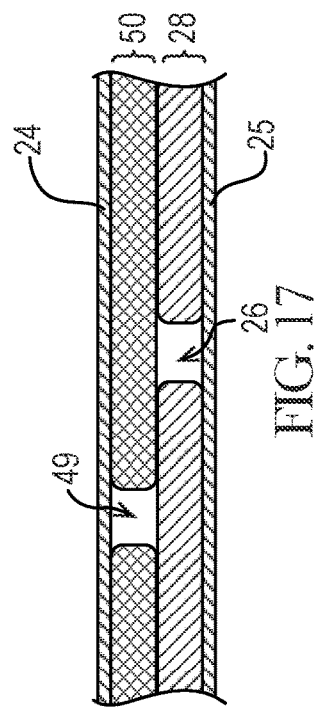
Figure 18:
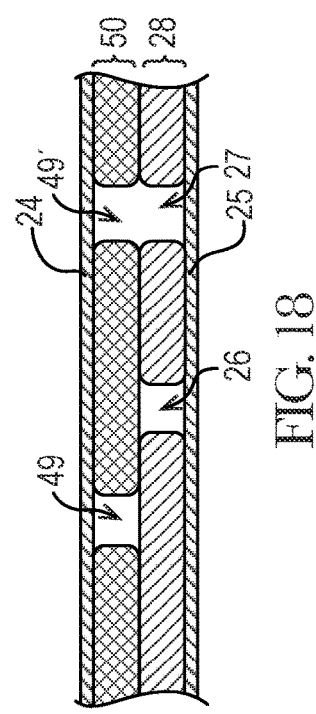

FIG. 16 illustrates an embodiment in which the channel 49 and the channel 26 are only partially aligned. In this embodiment, only a portion of the channel 49 overlaps with a portion of the channel 26. Such partially overlapping arrangement may continue along the longitudinal direction. Alternatively, the channels 49 and the channel 26 may become vertically aligned along the longitudinal direction or the channels may laterally deviate in direction such that there is no overlapping portion. An example configuration in which there is no overlapping portion between the channel 49 and the channel 26 is illustrated in FIG. 17. FIG. 18 illustrates yet another embodiment in which each of the LMS 50 and the absorbent core 28 defines two channels, 49, 49', 26, 27. As illustrated, channel 49 and channel 26 do not overlap with any other channels, while channel 49' of the LMS 50 overlaps, and in this case is completely aligned, with channel 27.

Figure 19:
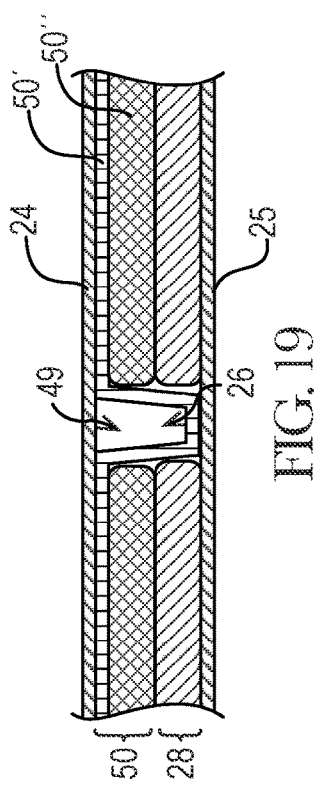
Figure 20:
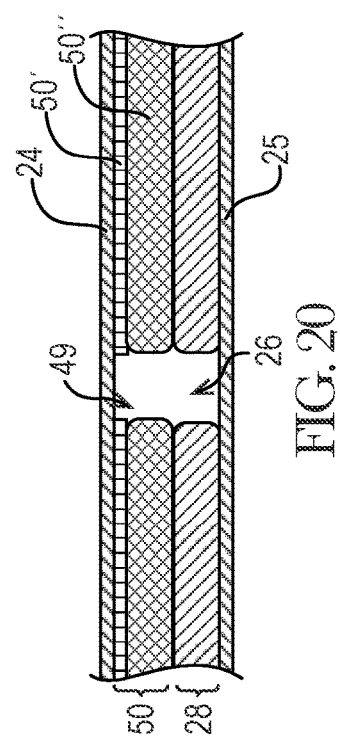

FIG. 19 illustrates an embodiment with a multi-layer LMS 50 having a first layer 50' and a second layer 50". In some embodiments, the first layer 50' comprises a nonwoven material and the second layer 50" comprises cross-linked cellulose fibers. In the illustrated arrangement, the absorbent core 28 defines a channel 26 and various layers of the LMS 50 collectively define a channel 49. The first layer 50' is recessed into both the channel 49 and the channel 26 and bonded to the backsheet 25 thereby forming a void between the first layer 50' and the topsheet 24. FIG. 20 illustrates another embodiment with an LMS 50 having a first layer 50' and a second layer 50". In the illustrated arrangement, the absorbent core 28 defines a channel 26 and an absence of both the first layer 50' and the second layer 50" LMS 50 defines a channel 49. In other embodiments, one or more layers of the LMS 50 are not recessed into the channel 49, or one or more layers of the LMS 50 are recessed into the channel 49, but not into the channel 26.

Figure 21:
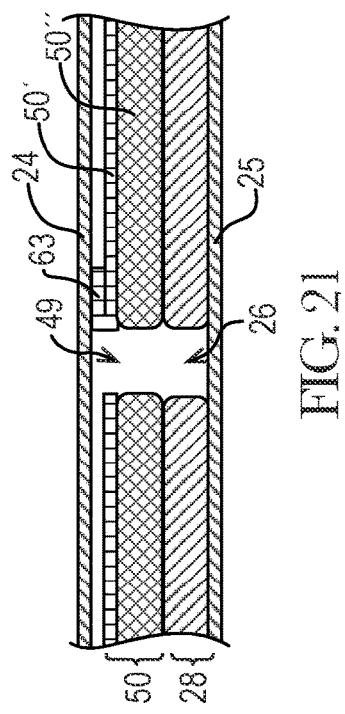

FIG. 21 illustrates an embodiment of a multi-layer LMS 50 in which the first layer 50' is cut and folded along the channel 49 to form a flap 63 that extends along the longitudinal direction of the channel 49. The flap 63 may be sandwiched between the first layer 50' and the topsheet 24 during the manufacturing of the absorbent article. Alternatively, the flap 63 may be folded downward toward the backsheet 25 such that it is received by the channel 49 and positioned along its wall. In some embodiments, flaps may be present on either lateral side of the channel 49 which may be formed by slicing the first layer 50' along the longitudinal centerline of the channel 49 and then folding the flap to expose the channel.

Figure 22:
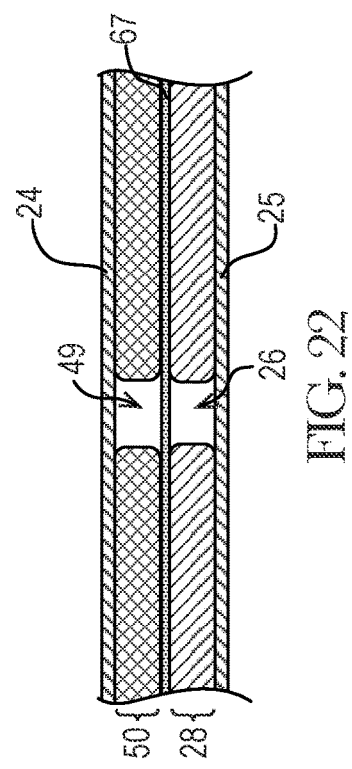
Figure 23:
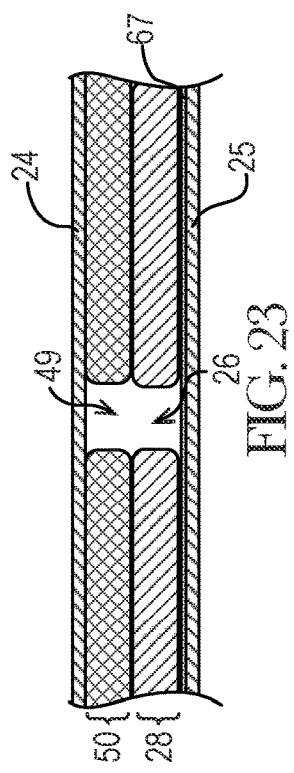

In some embodiments, it may be desirable to provide a visual indication of the channels. Such visual indication may be provided using any suitable technique. FIG. 22 illustrates an embodiment comprising a visually distinct layer 67. In some embodiments, the visually distinct layer 67 may be a layer on the garment-facing side of the LMS 50 that includes a pattern, image, color and/or tint that is different than that of other layers in the LMS 50. The visually distinct layer 67 is visible through at least one of the topsheet 24 and the backsheet 25 to provide an increased visual distinctiveness of the channel 49. The increased visual distinctiveness may serve as an internal serviceable indicia to facilitate more accurate alignment of the absorbent article on the wearer during the application process. FIG. 23 illustrates another example embodiment having the visually distinct layer 67. In the illustrated embodiment the visually distinct layer 67 is positioned between the absorbent core 28 and the backsheet 25. The visually distinct layer 67 may also be provided at other locations within the absorbent article.

Figure 24:
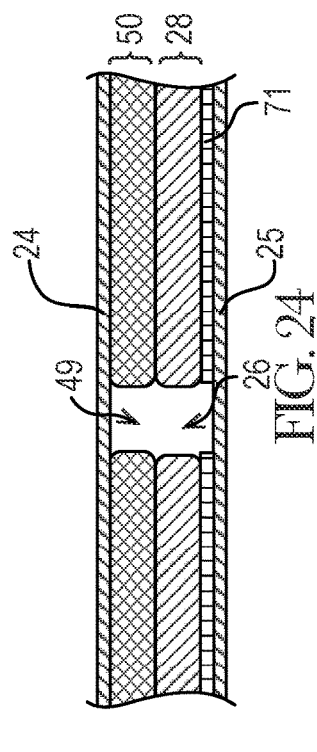
Figure 25:
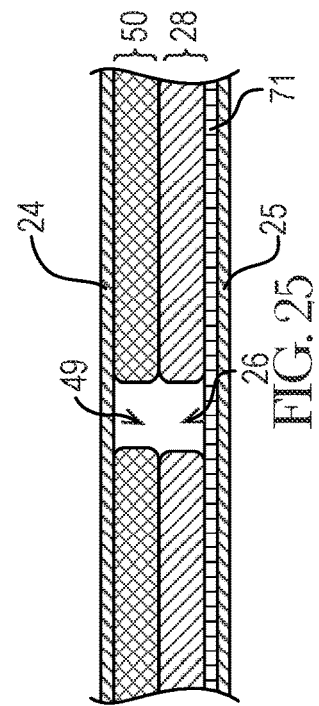
Figure 26:
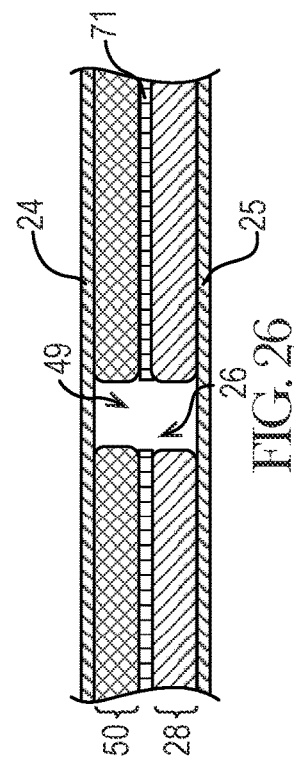

In addition to the LMS 50 and the absorbent core 28, it may be desirable to include additional layers in the absorbent article, such as a liquid distribution layer. FIGS. 24-26 illustrate embodiments comprising a liquid distribution layer 71 that comprises a liquid distribution material. The liquid distribution material may be a fibrous or foamed material, for example. The liquid distribution layer 71 may be discontinuous, as shown in FIGS. 24 and 26, or may be continuous, as shown in FIG. 25. Thus, the liquid distribution layer 71 may help to define a channel within the absorbent article or may span a channel defined by the LMS 50 and/or the absorbent core 28. Furthermore, the liquid distribution layer 71 may be positioned at any suitable layer of the absorbent article to achieve the desired liquid distribution. As shown in FIGS. 24 and 25, for example, the liquid distribution layer 71 is positioned between the absorbent core 28 and the backsheet 25. By comparison, in FIG. 26, the liquid distribution layer 71 is positioned between the LMS 50 and the absorbent core 28. In some embodiments, a liquid distribution layer may be positioned between the topsheet 24 and the LMS 50. Some embodiments may have a plurality of liquid distribution layers Separation Element In certain embodiments, a wearer-facing surface of an absorbent article may have a visual front portion and a visual back portion. The visual front portion and the visual back portion may be separated by a substantially laterally-extending separation element. The substantially laterally-extending separation element may be, for example, a graphical indicia printed on a topsheet of the absorbent article, or other layer of the absorbent article, that is visible through the topsheet. In some embodiments, the substantially laterally-extending separation element is a portion of a tinted layer that is visible through the wearer-facing surface. Additionally, the visual front portion may be visually distinct from the visual back portion based on a color difference and/or a printed pattern difference. Such visual separation between the visual front portion and the visual back portion may help for proper alignment of the absorbent article during its application.

In some embodiments, the substantially laterally-extending separation element comprises a structural separator that is located in the region of the absorbent article generally corresponding to the perineal region of the wearer (i.e., disposed between the urethra and the anus). The structural separator may, for example, limit the surface migration of urine to the back of the absorbent article and feces to the front of the absorbent article. A structural separator may include any three-dimensional feature or component that functions as a transverse barrier (TVB), such as one or more projections above the wearer-facing surface of the absorbent article, recesses below the plane of the wear-facing surface, and combinations thereof. One example includes a laterally-oriented web or sheet that is attached to the wearer-facing surface of the absorbent article and the standing barrier leg cuffs.

The structural separator may be rectangular or square when laid out flat in a relaxed, contracted state onto an even horizontal surface. The structural separator may also be trapezoid when laid out flat in a relaxed, contracted state onto an even horizontal surface. The structural separator may be hydrophobic (e.g., it may be hydrophilic and made hydrophobic with a hydrophobic surface coating, such as known in the art, for example a wax or a hydrophobic surface coating comprising one or more silicone polymers or fluorinated polymers.) In some embodiments, the structural separator may have an elastic behavior such that it can be significantly elastically extensible in a transverse direction or other direction. The structural separator may have a certain tension in use to ensure it forms an effective separator (barrier) with a Z-direction dimension, to avoid, or at least inhibit, migration of feces from the back to the front of the structural separator. Other embodiments of structural separators may include raised or thicker portions of the topsheet, elements of the acquisition system or absorbent core, separately applied elements, or holes or depressions in one or more of the absorbent core elements.

The structural separator may have any suitable structure and may be a ridge, bump, or flap, for example. The structural separator may be placed along a lateral axis of an absorbent article or may be positioned at an angle that is oblique to the lateral axis. In some embodiments, the structural separator may be positioned generally parallel to a channel within the LMS to aid in the controlling the flow of urine and/or feces into that channel.

One or more structural separators may be incorporated into absorbent articles having a variety of channel configurations, such as any of embodiments illustrated above in FIGS. 11-26.

FIGS. 27-34 are partial cross-sectional views of the absorbent articles comprising channels 49, 26 taken along a longitudinal axis that illustrate example types of structural separators 73. Similar to FIGS. 11-26, the absorbent articles of FIGS. 27-34 comprise a topsheet 24, a backsheet 25, and various configurations of the LMS 50 and the absorbent core 28 that define various channels. The illustrated absorbent articles also each comprise a structural separator 73 that is a projection above the wearer-facing surface of the absorbent article. The structural separator 73 may comprise, for example, an elastic film, a nonwoven sheet, a laminate of an elastic film and a nonwoven sheet material, a polyolefin film, or any other suitable materials. The nonwoven sheet material of the laminate can be positioned such that it is in contact with the skin of the wearer. Such a configuration of the laminate may provide more comfort to the wearer than when the elastic film is directly in contact with the skin of the wearer. Further, the structural separator 73 may be made of polyolefins known in the art, such as polyethylene and/or polypropylene, made into fibers, including bicomponent fibers that are then made into a nonwoven sheet. The nonwoven sheet material may be a necked nonwoven. The nonwoven sheet material may be a meltblown nonwoven or spunbond nonwoven or carded nonwoven. In some embodiments, it may be a laminate of spunbond or carded layer or layers and meltblown nonwoven layer(s).

Figure 27:
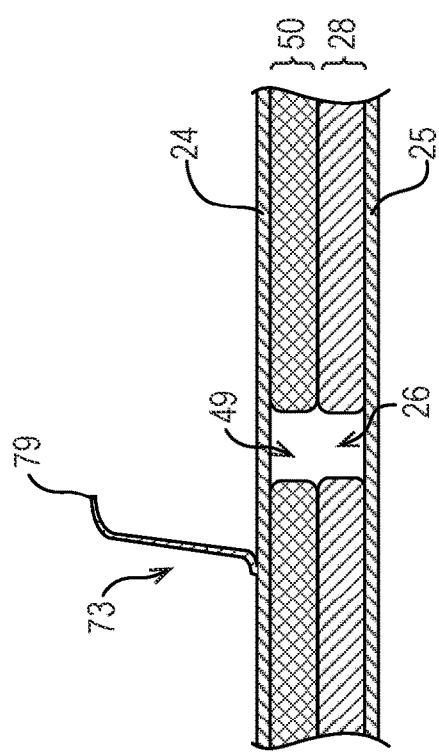
FIGS. 27-34 are partial cross-sectional views of absorbent articles comprising a structural separator and channels in a liquid management system in accordance with various non-limiting embodiments of the present disclosure.
Figure 28:
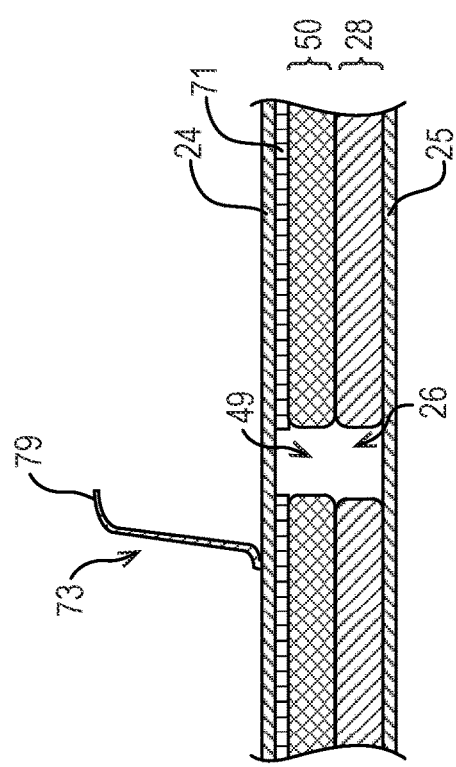
Figure 29:
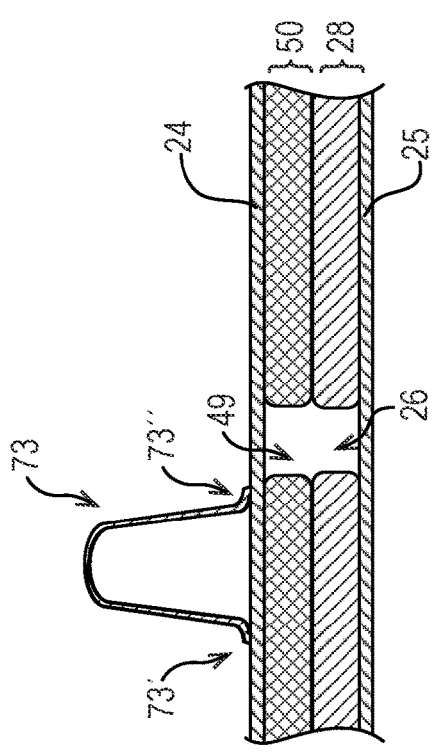
Figure 30:
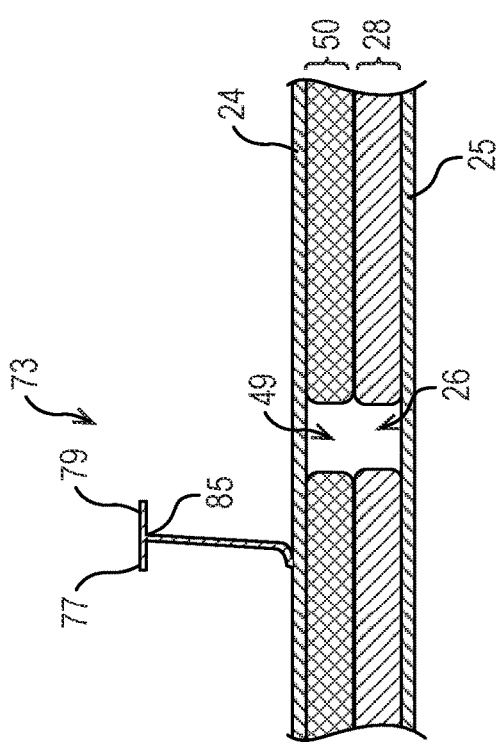

FIG. 27 illustrates an embodiment in which a structural separator 73 is bonded to a topsheet 24. The structural separator 73 is positioned between a front waist edge 10 (FIG. 1) of the absorbent article and a channel 49 defined by the LMS 50 and a channel 26 defined by the absorbent core 28. The structural separator 73 may span and may be bonded to the barrier leg cuffs 34 (FIG. 1). The structural separator 73 may limit the surface migration of urine and/or feces while helping to direct feces into the channels 49, 26. The structural separator 73 may comprise a flange 79 to help prevent, or at least inhibit, the flow of the urine and/or feces across the structural separator 73. While FIG. 27 illustrates channels on one side of the structural separator 73, other embodiments may have channels on both sides of the structural separator 73. FIG. 28 illustrates an embodiment comprising a liquid distribution layer 71 positioned between the topsheet 24 and the LMS 50. In other embodiments, the liquid distribution layer 71 may be positioned between the LMS 50 and the absorbent core 28 and/or between the absorbent core 28 and the backsheet. Additional details regarding the liquid distribution layer are described above with regard to FIGS. 24-26. FIG. 29 illustrates an example structural separator 73 that has a ridge-like formation. The structural separator 73 is bonded to the topsheet 24 at a first bond site 73' and a second bond site 73" to form a hump there between. In some embodiments, AGM, or other suitable material may be contained within the cavity defined by the topsheet 24 and the structural separator 73. FIG. 30 illustrates another embodiment of the structural separator 73. In this embodiment, the structural separator 73 comprises a first flange 77 and a second flange 79 positioned along a top edge 85 of the structural separator 73. The first and second flanges 77, 79 may serve to block, or at least inhibit, body exudates from undesirably migrating along the wearer-facing surface.

Figure 31:
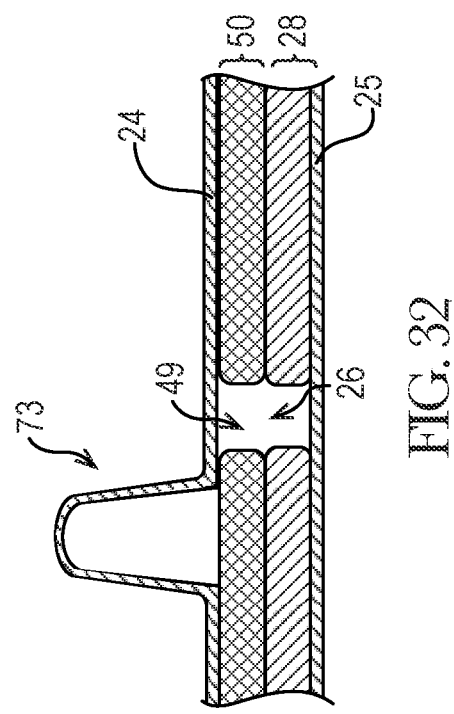
Figure 32:
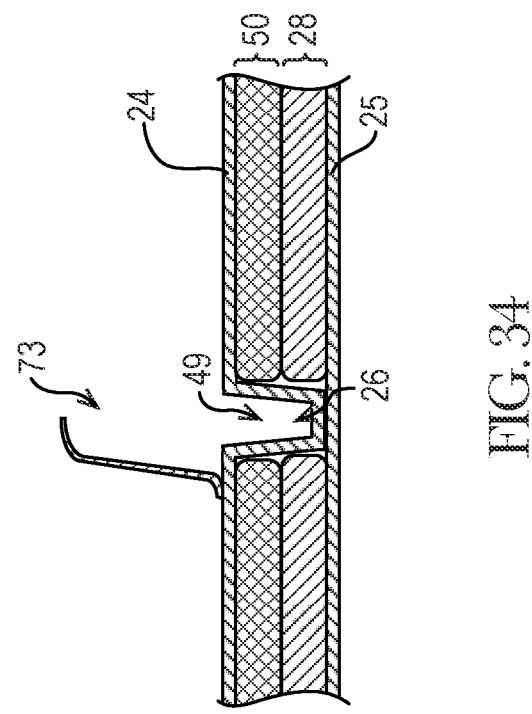
Figure 33:
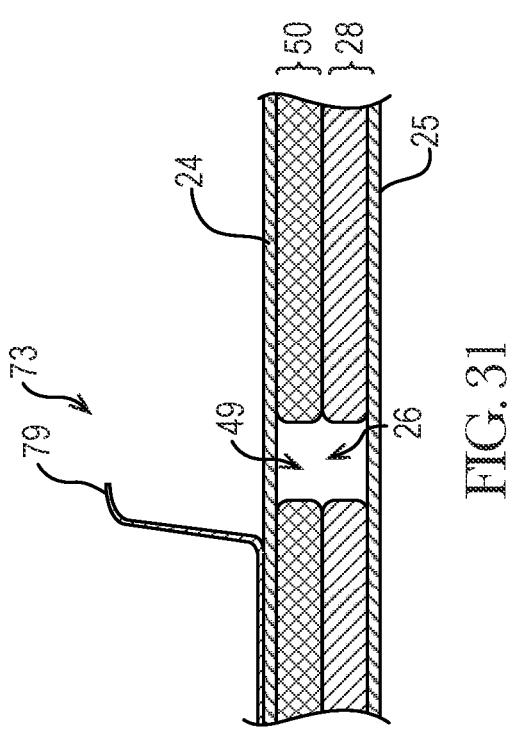
Figure 34:
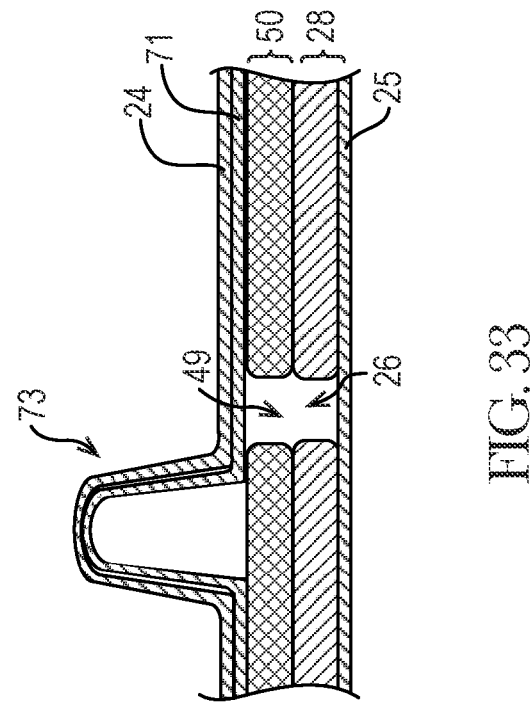

While FIGS. 27-30 illustrate the structural separator 73 as a discrete component bonded to the topsheet 24 of the absorbent article, this disclosure is not so limited. FIG. 31 illustrates an example embodiment in which the structural separator 73 is a component of a layer that is bonded to the topsheet 24 such that a first portion of the layer is bonded to the topsheet 24 and a second portion extends upwards from the topsheet 24 as a barrier. FIG. 32 illustrates an embodiment in which the topsheet 24 is formed with the structural separator 73. In this embodiment, the structural separator 73 has a ridge-like formation. In such an embodiment, the LMS 50, or portions thereof, or the core, or portions thereof may extend into the cavity defined by the ridge-like formation. In some embodiments, the structural separator 73 comprises a plurality of layers. Referring now to FIG. 33, the structural separator 73 is formed by a liquid distribution layer 71 and the topsheet 24. In other embodiments, different layers of the absorbent article may be used to form the structural separator 73, such as the topsheet 24 and at least a portion of the LMS 50, for example. As is to be appreciated, a structural separator can be used with absorbent articles having a variety of channel types. FIG. 34 illustrates an absorbent article with a portion of the topsheet 24 recessed into the channel 49 defined by the LMS 50 and the channel 26 defined by the absorbent core 28. The structural separator 73 is positioned proximate to the channel 49 to assist in the control of urine and/or feces migration. Any of the structural separators disclosed herein may be more stiff, rigid, or may have a greater thickness than, for example, the remainder of the topsheet 24, such that the structural separators may maintain their shape upon wetting or upon a force being applied thereto by a wearer.

In accordance with the present disclosure, absorbent articles may comprise one or more channels in the LMS that have different physical property values than other channels in the LMS. Example physical properties include the channel's width, length, orientation, volume, color, texture, area, or other physical properties. The absorbent article may have a visual front portion and a visual back portion that are defined by a substantially laterally-extending, or laterally-extending separation element. The substantially laterally-extending separation element may be a structure, such as structural separator 73, or may be a graphical indicia that is printed onto the topsheet or otherwise visible through a wearer-facing surface. A channel positioned in the visual front portion may have a first physical property while a channel in the visual back portion may have a second physical property. Some differences in physical properties of the channels may be visible through the wearer-facing surface to aid the caregiver in aligning the absorbent article in addition to providing desired performance characteristics.

Figure 35:
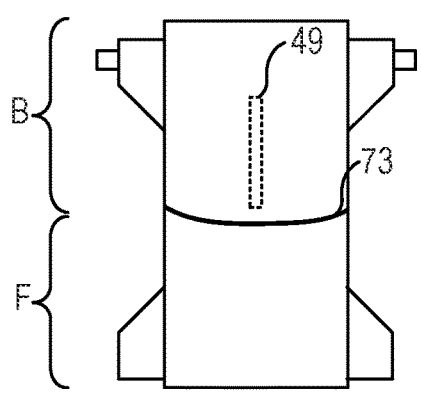
FIGS. 35-40 are top views of absorbent articles in comprising channels in a liquid management system in accordance with various non-limiting embodiments of the present disclosure.
Figure 38:
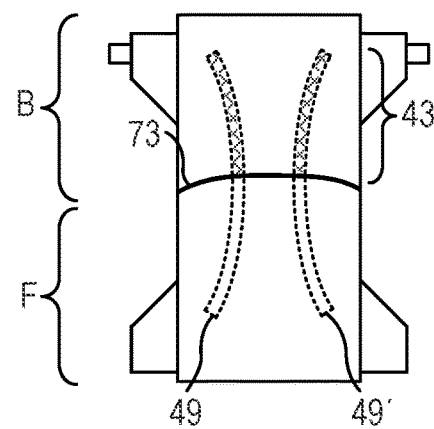
Figure 39:
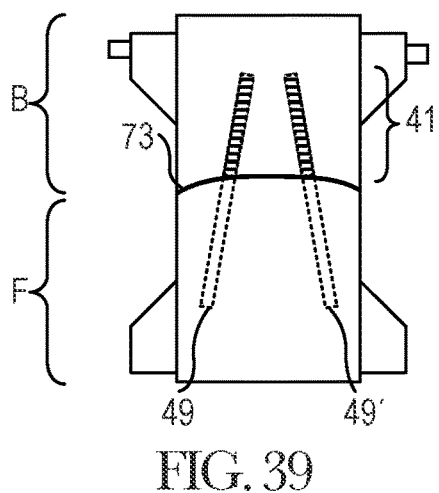
Figure 40:
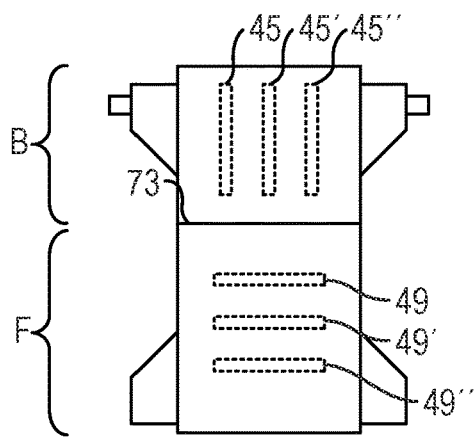

FIGS. 35-40 illustrate example differences in values of physical properties of one or more channels in the LMS located in a visual front portion (identified as "F") and the physical properties of one or more channels in the LMS located in a visual back portion (identified as "B"). While the absorbent articles illustrated in FIGS. 35-40 are diapers, it is to be appreciated that other types of absorbent articles, such as training pants, adult incontinence products, sanitary napkins, and the like, may also comprises channels in the LMS that have different physical property values in the visual front portion and the visual back portion. Furthermore, only channels in the LMS are illustrated in FIGS. 35-40 for the sake of clarity. Any channels in the absorbent core of the absorbent articles are not illustrated. The absorbent articles shown in FIGS. 35-40 have been simplified for clarity and accordingly various components, such as barrier leg cuffs, have been omitted. Also, while the substantially laterally-extending separation element is illustrated as a structural separator 73 in FIGS. 35-40, this disclosure is not so limited. Other embodiments, for example, may use a graphical indicia or other non-structural separation element to provide a visual separation between the visual front portion and the visual back portion. In some embodiments, the substantially laterally-extending separation element may be a combination of a structural element and printed indicia or tinted layers. Additionally, the substantially laterally-extending separation element may have any suitable orientation or arrangement. In FIG. 35, for example, the substantially laterally-extending separation element (illustrated as a structural separator 73) that is curved, while in other embodiments, the structural separator 73 may be straight (FIG. 40)

or may be comprised of a plurality of linear components (FIG. 37) or non-linear components, for example. Additionally, while the laterally-extending separation element is illustrated as extending across the entire lateral width of the absorbent article, it is to be understood that in some embodiments the laterally-extending separation element extends between the barrier leg cuffs.

Figure 36:
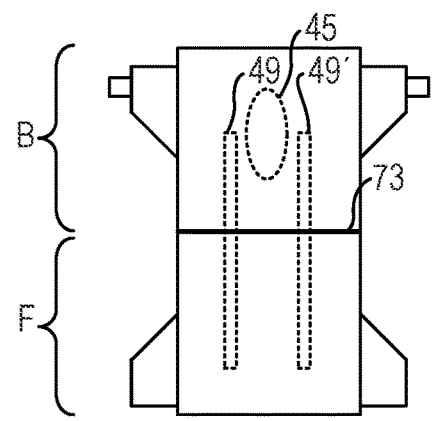

Referring first to FIG. 35, the illustrated value of the physical property of the channels in the LMS that differs in the visual front portion (F) and the visual back portion (B) is the presence/absence of the channel. As shown, a channel 49 in the LMS is located in the visual back portion (B) of the absorbent article while the visual front portion (F) does not have a channel. FIG. 36 illustrates that the number of channels in the LMS in the visual front portion (F) can differ from the number of channels in the LMS in the visual back portion (B). As shown, two channels 49, 49' are present in the visual front portion (F) and three channels 49, 49', 45 are present in the visual back portion (B). In the illustrated embodiment, channel 45 in the visual back portion (B) is sometimes called a pocket or a BM pocket. Such pocket in the LMS may generally align with a similar pocket positioned in the absorbent core. Generally, the BM pocket may be configured to host feces and limit its spreading.

Figure 37:
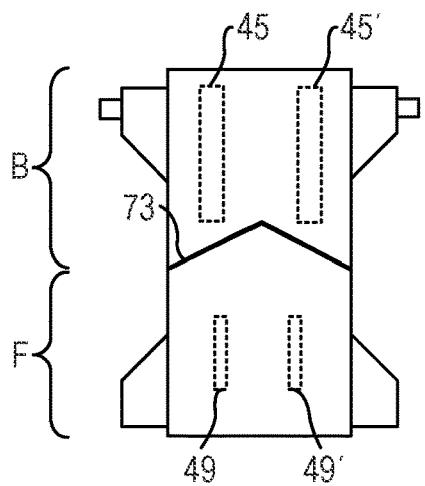

Referring now to FIG. 37, the area of the channels in the visual front portion (F) differ from the area of the channels in the visual back portion (B). As illustrated, the area of channels 49, 49' is less than the area of channels 45, 45'. In other embodiments, the area of the channels in the visual front portion (F) may be more than the area of the channels in the visual back portion. Similarly, in some embodiments, the size of the channels may vary such that the visually larger channel is positioned in one of the visual front portion (F) and the visual back portion (B). Some embodiments may have a plurality of channels in either the visual front portion, the visual back portion, or a plurality of channels in both portions. A total lateral width of the channels may be measured at a point along the longitudinal axis of the absorbent article by measuring the width of all of the channels at that point and cumulating the widths to determine a total lateral width at that point. By way of example, if an LMS defines three channels at a point along the longitudinal axis, with each channel having a width of 0.25 inches, the total lateral width would be 0.75 inches. The total lateral width of a plurality of channels at a point along the longitudinal axis in the visual front portion (F) may be different than the total lateral width of a plurality of channels at a point along the longitudinal axis in the visual back portion (B).

FIG. 38 illustrates that the color of a channel may be different in the visual front portion (F) than the visual back portion (B). As shown, channels 49, 49' span both the visual front portion (F) and the visual back portion (B). The portion of the channels 49, 49' positioned in the visual back portion (B), illustrated as portion 43, is colored. In some embodiments, the portion 43 of the channels 49, 49' are colored using a tinted layer, as illustrated in FIGS. 22 and 23, for example. FIG. 39 illustrates an embodiment in which a texture of channels in the visual front portion (F) different from the texture of the channels in the visual back portion (B). As shown, the portion 41 of the channels 49, 49' comprise a texture that is different from the texture from the portion of the channels 49, 49' in the front visual portion (F). The texture of the portion 41 may be, for example, knurled, ribbed, or dimpled.

FIG. 40 illustrates that the physical orientation of the channels present in the front visual portion (F) may differ from the physical orientation of the channels in the visual back portion (B). As shown visual front portion (F) has three channels 49, 49',49''' and visual back portion (B) comprises channels 45, 45', 45'''. While the number and area of the channels in the visual front portion (F) is the same as the number and area of the channels in the visual back portion (B), the physical orientation differ. Specifically, channels 49, 49',49''' extend in a substantially lateral direction while channels 45, 45', 45''' extend in a substantially longitudinal direction.

In other embodiments, there may be other physical differences in the visual front portion (F) and the visual back portion (B). For example, the number of layers in the visual front portion (F) may differ from the number of layers in the visual back portion (B). Thus, in the front portion a channel may be defined by two layers, while in the rear portion it is defined by three layers. The shape, curvature, or depth of the channels, and/or the number of layers defining the channels in the visual front portion (F) may differ than the channels in the visual back portion (B). For example, the visual front portion (F) may have a series of channels that generally extend in a lateral direction across the visual front portion (F) and the visual back portion (B) may have a single circular channel.

Sanitary Napkin Features

Referring to FIG. 41, an absorbent article may be a sanitary napkin 3010. The sanitary napkin 3010 may comprise a liquid permeable topsheet 3014, a liquid impermeable, or substantially liquid impermeable, backsheet 3016, and an absorbent core 3018. The absorbent core 3018 may have any or all of the features described herein with respect to the absorbent core 28 and, in some embodiments, may have a secondary topsheet 3019 (STS) instead of the liquid management system disclosed above. The STS 3019 may comprise one or more channels, as described above. In some embodiments, channels in the STS 3019 may be aligned with channels in the absorbent core 3018. The sanitary napkin 3010 may also comprise wings 3020 extending outwardly with respect to a longitudinal axis 3080 of the sanitary napkin 3010. The sanitary napkin 3010 may also comprise a lateral axis 3090. The wings 3020 may be joined to the topsheet 3014, the backsheet 3016, and/or the absorbent core 3018. The sanitary napkin 3010 may also comprise a front edge 3022, a rear edge 3024 longitudinally opposing the front edge 3022, a first side edge 3026, and a second side edge 3028 longitudinally opposing the first side edge 3026. The longitudinal axis 3080 may extend from a midpoint of the front edge 3022 to a midpoint of the rear edge 3024. The lateral axis 3090 may extend from a midpoint of the first side edge 3028 to a midpoint of the second side edge 3028. The sanitary napkin 3010 may also be provided with additional features commonly found in sanitary napkins as is known in the art.

Method of Making the Article

The absorbent articles (e.g., diapers, sanitary napkins, training pants, etc.) of the present disclosure may be made by any suitable methods known in the art. In particular, the absorbent articles may be hand-made or industrially produced at high speed. In some embodiments, the channels described herein may be created by punching, die cutting, slitting, or spreading the associated layer. In one example manufacturing process a drum is provided having a protrusion. A layer of air-laid fibers are deposited on the surface of the drum and fibers above the protrusion are removed and deposited in the surrounding area. In an embodiment, a rotating scarfing roll is used to remove the fibers. In another example embodiments, a channel in a rollstock acquisition layer material, such as a wet-laid cellulosic web or a nonwoven highloft, may be created by punching/die cutting or slitting and spreading. In an embodiment, a shape is cut to form a flap of material and the flap of material is folded back onto another portion of the web. An example embodiment utilizing flap-type construction is described above with regard to FIG. 23. If desired, the folded flap may be bonded to maintain its relative position. The shape may be, for example, a "U" shape or less than all the sides of a closed polygon shape.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it will be understood by those skilled in the art that various other changes and modifications may be made without departing from the spirit and scope of the present disclosure. It is therefore intended to cover in the appended claims all such changes and modifications that are within the scope of this disclosure.

What is claimed is:

1. An absorbent article comprising:
  a central longitudinal axis;
  a total longitudinal length extending in a direction parallel to the central longitudinal axis;
  a front waist region;
  a rear waist region;
  a crotch region positioned intermediate the front waist region and the rear waist region, wherein the front waist region, the rear waist region, and the crotch region each define ⅓ of the total longitudinal length of the absorbent article;
  a liquid permeable topsheet forming a portion of a wearer-facing surface of the absorbent article;
  a liquid impermeable backsheet;
  an absorbent core disposed at least partially intermediate the liquid permeable topsheet and the liquid impermeable backsheet and comprising an absorbent material, wherein the absorbent material is positioned within a core wrap, wherein the absorbent material comprises superabsorbent polymers, wherein the absorbent core defines a first channel therein, wherein the first channel is free of overlap with the central longitudinal axis, and wherein a first portion of the core wrap is joined to a second portion of the core wrap within the first channel; and
  a material positioned at least partially intermediate the liquid permeable topsheet and the core wrap, wherein the material defines a second channel therein, wherein the second channel is free of overlap with the central longitudinal axis, and wherein the second channel extends into the front waist region.

2. The absorbent article of claim 1, wherein a portion of the liquid permeable topsheet is recessed into the second channel.

3. The absorbent article of claim 1, wherein the core wrap comprises a first substrate and a second substrate, wherein the first portion is on the first substrate, and wherein the second portion is on the second substrate.

4. The absorbent article of claim 1, wherein at least a portion of the first channel partially overlaps at least a portion of the second channel.

5. The absorbent article of claim 4, wherein the first and second channels are positioned on a first side of the central longitudinal axis.

6. The absorbent article of claim 1, wherein the first channel comprises a first arcuate portion.

7. The absorbent article of claim 6, wherein the second channel comprises a second arcuate portion.

8. The absorbent article of claim 1, wherein the first channel comprises a first linear portion.

9. The absorbent article of claim 8, wherein the second channel comprises a second linear portion.

10. The absorbent article of claim 1, wherein the first channel is a permanent channel.

11. The absorbent article of claim 1, wherein the first portion of the core wrap is joined to the second portion of the core wrap in the first channel by an adhesive, pressure bonding, ultrasonic bonding, heat bonding, or combinations thereof.

12. The absorbent article of claim 1, wherein the first portion of the core wrap is joined intermittently to the second portion of the core wrap in the first channel.

13. An absorbent article comprising:
  a central longitudinal axis;
  a total longitudinal length extending in a direction parallel to the central longitudinal axis;
  a front waist region;
  a rear waist region;
  an elastic waist feature in the front waist region or the rear waist region;
  a crotch region positioned intermediate the front waist region and the rear waist region, wherein the front waist region, the rear waist region, and the crotch region each define ⅓ of the total longitudinal length of the absorbent article;
  a liquid permeable topsheet forming a portion of a wearer-facing surface of the absorbent article;
  a liquid impermeable backsheet film;
  an absorbent core disposed at least partially intermediate the liquid permeable topsheet and the liquid impermeable backsheet film and comprising an absorbent material, wherein the absorbent material is positioned within a core wrap, wherein the absorbent core defines a first channel therein, wherein a first portion of the core wrap is bonded to a second portion of the core wrap within the first channel, and wherein the absorbent core defines a second channel therein; and
  a material positioned at least partially intermediate the liquid permeable topsheet and the core wrap, wherein the material defines a third channel therein, wherein the third channel extends into the front waist region, and wherein the third channel is free of overlap with the central longitudinal axis.

14. The absorbent article of claim 13, wherein the first channel is positioned on a first side of the central longitudinal axis, and wherein the second channel is positioned on a second side of the central longitudinal axis.

15. The absorbent article of claim 14, wherein the material defines a fourth channel therein, and wherein the material comprises synthetic fibers.

16. The absorbent article of claim 15, wherein the third channel is positioned on the first side of the central longitudinal axis, and wherein the fourth channel is positioned on the second side of the central longitudinal axis.

17. The absorbent article of claim 16, wherein the first channel at least partially overlaps the third channel, and wherein the second channel at least partially overlaps the fourth channel.

18. The absorbent article of claim 13, wherein the first channel is a permanent channel.

19. The absorbent article of claim 13, wherein the first portion of the core wrap is joined to the second portion of the core wrap in the first channel by an adhesive, pressure bonding, ultrasonic bonding, heat bonding, or combinations thereof.

20. The absorbent article of claim 13, wherein the first portion of the core wrap is joined intermittently to the second portion of the core wrap in the first channel.

* * * * *